(12) United States Patent
Bala et al.

(10) Patent No.: US 9,034,879 B2
(45) Date of Patent: May 19, 2015

(54) HETEROCYCLIC COMPOUNDS FOR THE TREATMENT OF CF

(75) Inventors: Kamlesh Jagdis Bala, Horsham (GB); Rebecca Butler, Horsham (GB); Stephen Paul Collingwood, Haywards Heath (GB); Edward Charles Hall, Horsham (GB); Lee Edwards, Partridge Green (GB); Darren Mark Legrand, East Grinstead (GB); Katrin Spiegel, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/343,861

(22) PCT Filed: Sep. 14, 2012

(86) PCT No.: PCT/IB2012/054826
§ 371 (c)(1),
(2), (4) Date: Mar. 9, 2014

(87) PCT Pub. No.: WO2013/038386
PCT Pub. Date: Mar. 21, 2013

(65) Prior Publication Data
US 2014/0228376 A1    Aug. 14, 2014

Related U.S. Application Data

(60) Provisional application No. 61/535,560, filed on Sep. 16, 2011.

(51) Int. Cl.
*A61K 31/497* (2006.01)
*C07D 417/04* (2006.01)
*C07D 413/04* (2006.01)
*A61K 31/4439* (2006.01)
*A61K 45/06* (2006.01)

(52) U.S. Cl.
CPC .......... *A61K 31/497* (2013.01); *C07D 413/04* (2013.01); *C07D 417/04* (2013.01); *A61K 31/4439* (2013.01); *A61K 45/06* (2013.01)

(58) Field of Classification Search
CPC .......................... A61K 31/497; C07D 417/04
USPC .................................... 514/255.05; 544/405
See application file for complete search history.

(56) References Cited

U.S. PATENT DOCUMENTS

2014/0323485 A1    10/2014    Bala et al.

FOREIGN PATENT DOCUMENTS

| WO | 2009/138378 A1 | 11/2009 |
| WO | 2010/071837 A1 | 6/2010 |
| WO | 2010/123933 A1 | 10/2010 |

*Primary Examiner* — Taofiq A Solola
(74) *Attorney, Agent, or Firm* — Rona Nardone

(57) ABSTRACT

The present invention provides pyridin-oxadiazole/thiadiazole derivatives of Formula I wherein A is N or CR 4a; and (ii) or (iii) which restore or enhance the function of mutant and/or wild type CFTR to treat cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced). Pharmaceutical compositions comprising such derivatives are also encompassed.

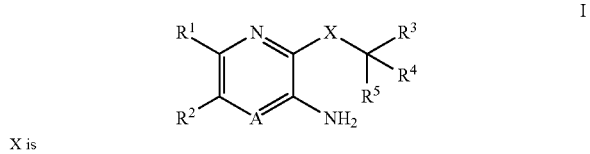

X is

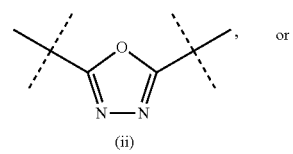

, or

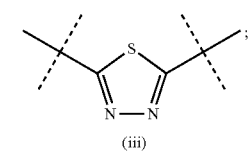

;

14 Claims, No Drawings

HETEROCYCLIC COMPOUNDS FOR THE TREATMENT OF CF

This application is a U.S. National Phase filing of International Application No. PCT/IB2012/054826 filed Sep. 9, 2012, which claims priority to U.S. Application No. 61/535,560 filed Sep. 16, 2011, the contents of which are incorporated herein by reference in their entirety.

FIELD OF THE INVENTION

This invention relates to pyridin-oxadiazole/thiadiazole derivatives, their preparation and use as pharmaceuticals.

BACKGROUND

Cystic fibrosis (CF) is a fatal genetic disease caused by mutations in the gene encoding the CF transmembrane conductance regulator (CFTR), a protein kinase A (PKA)-activated epithelial anion channel involved in salt and fluid transport in multiple organs, including the lung. Most CF mutations either reduce the number of CFTR channels at the cell surface (e.g., synthesis or processing mutations) or impair channel function (e.g., gating or conductance mutations) or both. There are currently no approved therapies that target CFTR directly. The present invention discloses compounds which restore or enhance the function of mutant and/or wild type CFTR to treat cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

DESCRIPTION OF THE INVENTION

In a first aspect, the invention provides compounds according to Formula I:

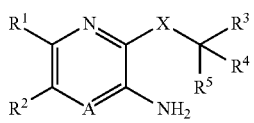

I wherein:
A is N or $CR^{4a}$;
X is

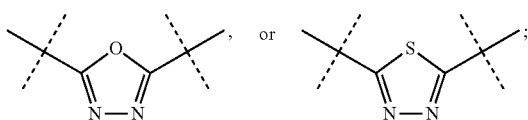

$R^1$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; halogen; $SO_2NR^8R^9$; $SO_2R^{10}$; S—$C_1$-$C_8$alkyl optionally substituted by one or more halogen atoms; S—$C_6$-$C_{14}$ aryl; —($C_0$-$C_4$ alkyl)-$C_6$-$C_{14}$ aryl; and —($C_0$-$C_4$ alkyl)-3 to 14 membered heterocyclyl; wherein the heterocyclyl contains at least one heteroatom selected from N, O and S; CN; $NR^{11}R^{12}$; $CONR^{13}R^{14}$; $NR^{13}SO_2R^{15}$; $NR^{13}(O)R^{15}$ and $CO_2R^{15}$, wherein the cycloalkyl, cycloalkenyl, aryl and heterocyclyl groups are each optionally substituted by one or more Z substituents;
$R^2$ is 1-$C_4$ haloalkyl;
$R^3$ is H or 1-$C_8$ alkyl optionally substituted by one or more halogen atoms;
$R^4$ is H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; $C_1$-$C_4$ alkoxy 1-$C_4$ alkyl; $C_1$-$C_8$ hydroxyalkyl; OH; CN; fluorine; —$(CH_2)_m$—$NR^{17}R^{18}$; —($C_0$-$C_4$ alkyl)-$C_6$-$C_{14}$ aryl; —($C_0$-$C_4$ alkyl)-3 to 14 membered heterocyclyl, wherein the heterocyclyl contains at least one heteroatom selected from N, O and S; or —($C_0$-$C_4$ alkyl)-$CO_2R^{15}$, wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents;
$R^{4a}$ is selected from H; $C_1$-$C_4$ alkyl optionally substituted by one or more halogen atoms; $C_2$-$C_8$ alkenyl; —($C_0$-$C_4$ alkyl)-$C_6$-$C_{14}$ aryl; —($C_0$-$C_4$ alkyl)-3 to 14 membered heterocyclyl; $C_1$-$C_8$ hydroxyalkyl; halogen; —$(CH_2)_m$—$NR^{17}R^{18}$; —($C_0$-$C_4$ alkyl)-$CO_2R^{15}$ and —($C_0$-$C_4$ alkyl)-$C(O)NR^{17}R^{18}$; wherein the —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents;
$R^5$ is $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; fluorine; —$(CH_2)_m$—$NR^{17}R^{18}$; $(CH_2)_m$—$OR^4$; —($C_0$-$C_4$ alkyl)-$C_6$-$C_{14}$ aryl; —($C_0$-$C_4$ alkyl)-3 to 14 membered heterocyclyl, wherein the heterocyclyl contains at least one heteroatom selected from N, O and S; or —($C_0$-$C_4$ alkyl)-$CO_2R^{15}$, wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents; or
$R^3$ and $R^4$ together form an oxo group (C=O); or
$R^3$ and $R^5$ together with the carbon atoms to which they are bound form a 3 to 8 membered cycloalkyl; or
$R^4$ and $R^5$ together with the carbon atoms to which they are bound form a 5 to 8 membered cycloalkyl or a 5 to 8 membered heterocyclyl containing one or more heteroatoms selected from N, O and S, wherein the ring system is optionally substituted by one or more Z substituents;
m is 0, 1, 2 or 3;
$R^8$, $R^{11}$, $R^{13}$ and $R^{17}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;
$R^9$, $R^{10}$, $R^{12}$, $R^{14}$, $R^{15}$, $R^{16}$ and $R^{18}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclyl, wherein the heterocyclyl contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclyl optionally substituted by one or more Z substituents;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{30}(SO_2)R^{32}$, $(SO_2)NR^{31}R^{32}$, $(SO_2)R^{32}$, $NR^{30}C(O)R^{32}$, $C(O)NR^{31}R^{32}$, $NR^{30}C(O)NR^{31}R^{32}$, $NR^{30}C(O)OR^{19}$, $NR^{31}R^{32}$, $C(O)OR^{31}$, $C(O)R^{31}$, $SR^{31}$, $OR^{31}$, oxo, CN, $NO_2$, halogen or a 3 to 14 membered heterocyclyl, wherein the heterocyclyl contains at least one heteroatom selected from N, O and S;

$R^{30}$ is H or $C_1$-$C_6$ alkyl;

$R^{31}$ and $R^{32}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl)$_2$; or $R^{31}$ and $R^{32}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy;

or a pharmaceutically acceptable salt thereof.

Various embodiments of the invention are described herein. It will be recognized that features specified in each embodiment may be combined with other specified features to provide further embodiments.

In an embodiment of the invention as described anywhere herein, wherein A is $CR^{4a}$ and $R^{4a}$ is selected from halogen, $C_1$-$C_4$ alkyl optionally substituted by one or more halogen atoms; $C_2$-$C_8$ alkenyl and —($C_0$-$C_4$ alkyl)-$C_6$-$C_{14}$ aryl; wherein the —($C_0$-$C_4$ alkyl)-$C_6$-$C_{14}$ aryl may be optionally substituted by one or more Z substituents.

In an embodiment of the invention as described anywhere herein, wherein A is $CR^{4a}$ and $R^{4a}$ is selected from halogen, $C_1$-$C_4$ alkyl optionally substituted by one or more halogen atoms; $C_2$-$C_8$ alkenyl and —($C_0$-$C_4$ alkyl)-$C_6$-$C_{14}$ aryl.

In an embodiment of the invention as described anywhere herein, wherein A is $CR^{4a}$ and $R^{4a}$ is selected from chlorine, ethyl, isopropyl, isopropenyl and phenyl; wherein the phenyl may be optionally substituted by one or more Z substituents.

In an embodiment of the invention as described anywhere herein, wherein X is

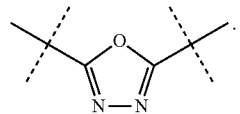

In an embodiment of the invention as described anywhere herein, wherein
$R^1$ is selected from H; $C_1$-$C_8$ alkyl optionally substituted by one or more halogen atoms; $C_3$-$C_{10}$ cycloalkyl; $C_1$-$C_8$ alkoxy optionally substituted by one or more halogen atoms; halogen; $C_6$-$C_{14}$ aryl; —($C_0$-$C_4$ alkyl)-3 to 14 membered heterocyclyl wherein the heterocyclyl contains at least one heteroatom selected from N, O and S; and $NR^{11}R^{12}$, wherein the aryl and heterocyclyl are each optionally substituted by one or more Z substituents.

In an embodiment of the invention as described anywhere herein, wherein $R^1$ is selected from H, $C_1$-$C_4$ alkyl optionally substituted by one or more halogen atoms; $C_3$-$C_{10}$ cycloalkyl; $C_1$-$C_4$ alkoxy optionally substituted by one or more halogen atoms and halogen.

In an embodiment of the invention as described anywhere herein, wherein $R^1$ is selected from $C_1$-$C_4$ alkyl optionally substituted by one or more halogen atoms; $C_3$-$C_{10}$ cycloalkyl; $C_1$-$C_4$ alkoxy optionally substituted by one or more halogen atoms and halogen.

In an embodiment of the invention as described anywhere herein, wherein
$R^1$ is selected from H, methoxy, trifluoromethyl, bromine, cyclopropyl, and methyl.

In an embodiment of the invention as described anywhere herein, wherein
$R^1$ is aryl, wherein aryl is phenyl optionally substituted by one or more Z substituents.

In an embodiment of the invention as described anywhere herein, wherein
$R^2$ is $CF_3$.

In an embodiment of the invention as described anywhere herein, wherein
$R^3$ is selected from H or $C_1$-$C_4$ alkyl optionally substituted by one and more halogen atoms.

In an embodiment of the invention as described anywhere herein, wherein $R^4$ is selected from H; $C_1$-$C_4$ alkyl optionally substituted by one or more halogen atoms; $C_1$-$C_4$ alkoxy optionally substituted by one or more halogen atoms; —$(CH_2)_m$—$NR^{17}R^{18}$ and OH; $R^{17}$ and $R^{18}$ are each independently H; $C_1$-$C_8$ alkyl optionally substituted by one or more halogen atoms.

In an embodiment of the invention as described anywhere herein, wherein $R^5$ is selected from H; $C_1$-$C_4$ alkyl optionally substituted by one or more halogen atoms; $C_1$-$C_4$ alkoxy optionally substituted by one or more halogen atoms; OH; CN; halogen; —($C_0$-$C_4$ alkyl)-$C_6$-$C_{14}$ aryl; and —($C_0$-$C_4$ alkyl)-3 to 14 membered heterocyclyl; wherein the heterocyclyl contains at least one heteroatom selected from N, O and S, wherein the aryl and heterocyclyl groups are each optionally substituted by one or more Z substituents.

In an embodiment of the invention as described anywhere herein, wherein $R^3$ and $R^5$ together with the carbon atoms to which they are bound form a 3 to 6 membered cycloalkyl.

In an embodiment of the invention as described anywhere herein, wherein $R^4$ and $R^5$ together with the carbon atoms to which they are bound form a 5 to 6 membered cycloalkyl or a 5 to 6 membered heterocyclyl containing one or more heteroatoms selected from N, O and S, wherein the heterocyclyl is optionally substituted by one or more Z substituents.

In an embodiment of the invention as described anywhere herein, wherein
$R^3$ is selected from H or $C_1$-$C_4$ alkyl optionally substituted by one and more halogen atoms;
$R^4$ is selected from H; $C_1$-$C_4$ alkyl optionally substituted by one or more halogen atoms; $C_1$-$C_4$ alkoxy optionally substituted by one or more halogen atoms; —$(CH_2)_m$—$NR^{17}R^{15}$ and OH;
$R^5$ is selected from H; $C_1$-$C_4$ alkyl optionally substituted by one or more halogen atoms; $C_1$-$C_4$ alkoxy optionally substituted by one or more halogen atoms; OH; CN; halogen; —($C_0$-$C_4$ alkyl)-$C_6$-$C_{14}$ aryl; and —($C_0$-$C_4$ alkyl)-3 to 14 membered heterocyclyl; wherein the heterocyclyl contains at least one heteroatom selected from N, O and S, wherein the aryl and heterocyclyl groups are each optionally substituted by one or more Z substituents; or
$R^3$ and $R^5$ together with the carbon atoms to which they are bound form a 3 to 6 membered cycloalkyl; or
$R^4$ and $R^5$ together with the carbon atoms to which they are bound form a 5 to 6 membered cycloalkyl or a 5 to 6 membered heterocyclyl containing one or more heteroatoms selected from N, O and S, wherein the heterocyclyl is optionally substituted by one or more Z substituents;
$R^{17}$ and $R^{18}$ are each independently H; $C_1$-$C_8$ alkyl optionally substituted by one or more halogen atoms.

In an embodiment of the invention as described anywhere herein, wherein
A is $CR^{4a}$;
X is

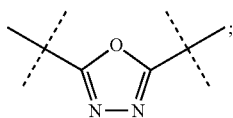

$R^1$ is selected from H; $C_1$-$C_4$ alkoxy optionally substituted by one or more halogen atoms; and $C_1$-$C_4$ alkoxy optionally substituted by one or more halogen atoms;
$R^2$ is $CF_3$,
$R^3$ is H, $CH_3$ or $CF_3$;
$R^4$ is H or Me;
$R^5$ is phenyl, —$NR^{17}R^{18}$ or OH; and
$R^{17}$ and $R^{18}$ are each independently H; $C_1$-$C_8$ alkyl optionally substituted by one or more halogen atoms.

In an embodiment of the invention as described anywhere herein, wherein
A is $CR^{4a}$;
X is

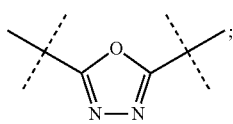

$R^1$ is selected from $C_1$-$C_4$ alkoxy optionally substituted by one or more halogen atoms; and $C_1$-$C_4$ alkoxy optionally substituted by one or more halogen atoms;
$R^2$ is $CF_3$,
$R^3$ is H, $CH_3$ or $CF_3$;
$R^4$ is H or Me;
$R^5$ is —$NR^{17}R^{18}$ or OH; and
$R^{17}$ and $R^{18}$ are each independently H; $C_1$-$C_8$ alkyl optionally substituted by one or more halogen atoms.

In an embodiment of the invention as described anywhere herein, the compounds of Formula I include compounds of Formula II:

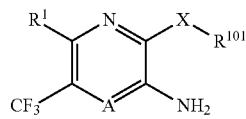

or a pharmaceutically acceptable salt thereof, wherein A, $R^1$, $R^2$, $R^3$ and $R^{4a}$ are as defined in embodiments 1-16; and $R^{101}$ is selected from the following:

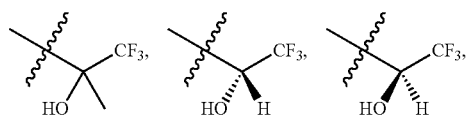

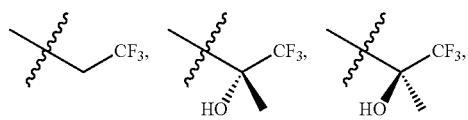

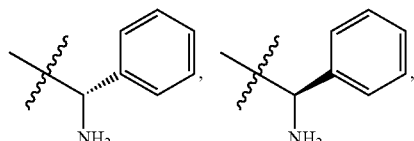

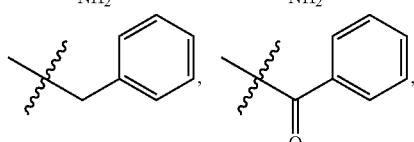

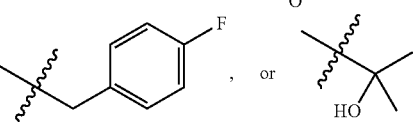

In an embodiment of the invention as described anywhere herein, wherein A is $CR^{4a}$, wherein $R^{4a}$ is H.

In an embodiment of the invention as described anywhere herein, wherein A is $CR^{4a}$; $R^1$ is $C_1$-$C_4$ alkyl optionally substituted by one or more halogen atoms;

$R^{101}$ is or

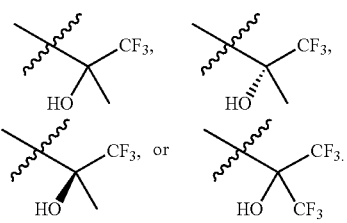

In an embodiment of the invention as described anywhere herein, wherein $R^{101}$ is

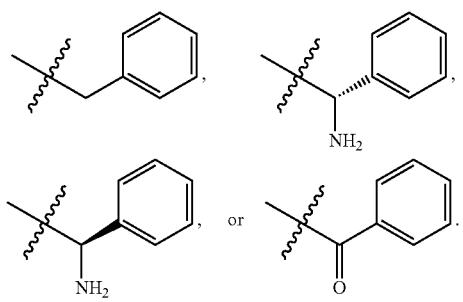

In an embodiment of the invention as described anywhere herein, A is N.

In an embodiment of the invention as described anywhere herein, A is $CR^{4a}$, wherein $R^{4a}$ is H or $C_1$-$C_4$ alkyl optionally substituted by one or more halogen atoms;

In an embodiment of the invention as described anywhere herein, A is $CR^{4a}$, wherein $R^{4a}$ is H, methyl, or ethyl.

In an embodiment of the invention as described anywhere herein, A is $CR^{4a}$, wherein $R^{4a}$ is H.

In an embodiment of the invention as described anywhere herein, X is

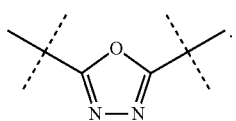

In an embodiment of the invention as described anywhere herein, X is

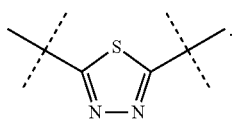

An embodiment of the invention as defined above provides compounds according to Formula I, wherein
A is $CR^{4a}$;
X is

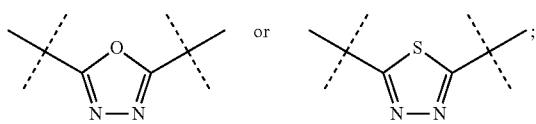

$R^1$ is halogen, $C_1$-$C_4$ alkyl optionally substituted by one or more halogen atoms, or $C_1$-$C_4$ alkoxy optionally substituted by one or more halogen atoms;
$R^2$ is $C_1$-$C_4$ haloalkyl;
$R^3$ is H or Me;
$R^{4a}$ is H;
$R^4$ is —$(CH_2)_m$—$NR^{17}R^{18}$; —$(CH_2)_m$—$OR^3$; or OH;
m is 0, 1 or 2;

$R^5$ is $C_1$-$C_4$ alkyl optionally substituted by one or more halogen atoms; $C_1$-$C_4$ alkoxy optionally substituted by one or more halogen atoms; —$(CH_2)_m$—$NR^{17}R^{18}$; —$(CH_2)_m$—$OR^4$; or —$(C_0$-$C_4$ alkyl)-$C_6$-$C_{10}$ aryl, wherein the —$(C_0$-$C_4$ alkyl)-$C_6$-$C_{10}$ aryl is optionally substituted by one or more Z substituents; or $R^4$ and $R^5$ together with the carbon atoms to which they are bound form a 5 to 6 membered heterocyclic ring system containing one or more heteroatoms selected from N, O and S, wherein the ring system is optionally substituted by one or more Z substituents; and $R^{17}$ and $R^{18}$ are each independently H; $C_1$-$C_4$ alkyl optionally substituted by one or more halogen atoms.

An embodiment of the invention as defined above provides compounds according to Formula I, wherein
A is $CR^{4a}$;
X is

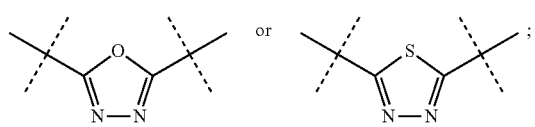

$R^1$ is $C_1$-$C_4$ alkyl optionally substituted by one or more halogen atoms;
$R^2$ is $C_1$-$C_4$ haloalkyl;
$R^3$ is H or $C_1$-$C_4$ alkyl optionally substituted by one or more halogen atoms;
$R^{4a}$ is H;
$R^4$ is —$(CH_2)_m$—$NR^{17}R^{18}$; —$(CH_2)_m$—$OR^3$; or OH;
m is 0, 1 or 2;
$R^5$ is $C_1$-$C_4$ alkyl optionally substituted by one or more halogen atoms; $C_1$-$C_4$ alkoxy optionally substituted by one or more halogen atoms; —$(CH_2)_m$—$NR^{17}R^{18}$; —$(CH_2)_m$—$OR^4$; or $C_6$-$C_{10}$ aryl, wherein the $C_6$-$C_{10}$ aryl is optionally substituted by one or more Z substituents; or $R^4$ and $R^5$ together with the carbon atoms to which they are bound form a 5 to 6 membered heterocyclic ring system containing one or more heteroatoms selected from N, O and S, wherein the ring system is optionally substituted by one or more Z substituents; and $R^{17}$ and $R^{18}$ are each independently H; $C_1$-$C_4$ alkyl optionally substituted by one or more halogen atoms.

An embodiment of the invention as defined above provides compounds according to Formula I, wherein
A is $CR^{4a}$;
X is

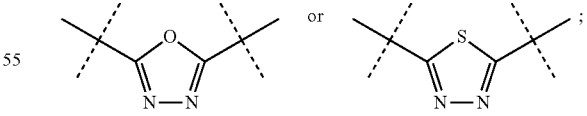

$R^1$ is $C_1$-$C_4$ alkoxy optionally substituted by one or more halogen atoms;
$R^2$ is $C_1$-$C_4$ haloalkyl;
$R^3$ is H or $C_1$-$C_4$ alkyl optionally substituted by one or more halogen atoms; $R^{4a}$ is H;
$R^4$ is —$(CH_2)_m$—$NR^{17}R^{18}$; —$(CH_2)_m$—$OR^3$; or OH;
is 0, 1 or 2;
$R^5$ is $C_1$-$C_4$ alkyl optionally substituted by one or more halogen atoms; $C_1$-$C_4$ alkoxy optionally substituted by one or more halogen atoms; or —$C_6$-$C_{10}$ aryl, wherein the $C_6$-$C_{10}$ aryl is optionally substituted by one or more Z substituents; or $R^4$ and $R^5$ together with the carbon atoms to which they are bound form a 5 to 6 membered heterocyclic ring system containing one or more heteroatoms selected from N, O and S, wherein the ring system is optionally substituted by one or more Z substituents; and $R^{17}$ and $R^{18}$ are each independently H; $C_1$-$C_4$ alkyl optionally substituted by one or more halogen atoms.

An embodiment of the invention as defined above provides compounds according to Formula I, wherein
A is $CR^{4a}$;
X is

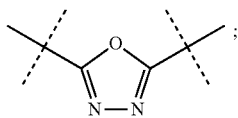

$R^1$ is $C_1$-$C_4$ alkoxy optionally substituted by one or more halogen atoms;
$R^2$ is $C_1$-$C_4$ haloalkyl;
$R^3$ is H, methyl or trifluoromethyl;
$R^{4a}$ is H;
$R^4$ is —$NR^{17}R^{18}$; or OH;
$R^5$ is $C_1$-$C_4$ alkyl optionally substituted by one or more halogen atoms; phenyl, wherein the phenyl is optionally substituted by one or more Z substituents; and
$R^{17}$ and $R^{18}$ are each independently H; $C_1$-$C_4$ alkyl optionally substituted by one or more halogen atoms.

An embodiment of the invention as defined above provides compounds according to Formula I, wherein
A is $CR^{4a}$;
X is

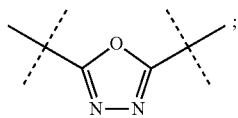

$R^1$ is $C_1$-$C_4$ alkyl optionally substituted by one or more halogen atoms;
$R^2$ is $C_1$-$C_4$ haloalkyl;
$R^3$ is H, methyl or trifluoromethyl;
$R^{4a}$ is H;
$R^4$ is —$NR^{17}R^{18}$; or OH;
$R^5$ is $C_1$-$C_4$ alkyl optionally substituted by one or more halogen atoms; phenyl, wherein the phenyl is optionally substituted by one or more Z substituents; and
$R^{17}$ and $R^{18}$ are each independently H; $C_1$-$C_4$ alkyl optionally substituted by one or more halogen atoms.

An embodiment of the invention as defined above provides compounds according to Formula I, wherein
A is $CR^{4a}$;
X is

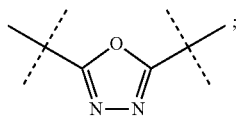

$R^1$ is $C_1$-$C_4$ alkoxy optionally substituted by one or more halogen atoms;
$R^2$ is $C_1$-$C_4$ haloalkyl;
$R^3$ is H, methyl or trifluoromethyl;
$R^{4a}$ is H;
$R^4$ is —$NR^{17}R^{18}$; or OH;
$R^5$ is $C_1$-$C_4$ alkyl optionally substituted by one or more halogen atoms; and
$R^{17}$ and $R^{18}$ are each independently H; $C_1$-$C_4$ alkyl optionally substituted by one or more halogen atoms.

Another embodiment of the invention as defined above provides compounds with substantially pure enantiomers with the R configuration.

Another embodiment of the invention as defined above provides compounds with substantially pure enantiomers with the S configuration.

Certain compounds of Formula I include compounds of Formula II:

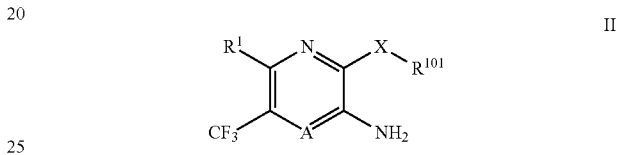

II or a pharmaceutically acceptable salt thereof, wherein A, $R^1$, $R^2$, $R^3$ and $R^{4a}$ have the definitions of Formula I; and $R^{101}$ is selected from the following:

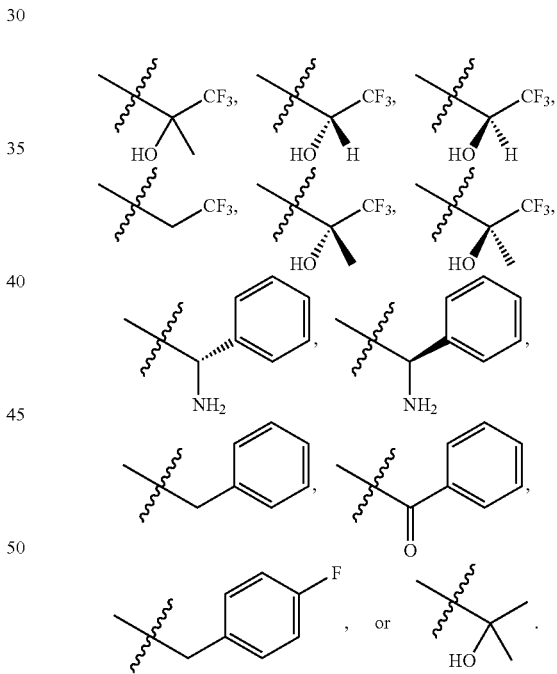

In a further embodiment of Formula II of the invention herein, A is $CR^{4a}$, wherein $R^{4a}$ is H.

In a further embodiment of Formula II of the invention herein, $R^1$ is selected from H; $C_1$-$C_4$ alkyl optionally substituted by one or more halogen atoms; $C_1$-$C_4$ alkoxy optionally substituted by one or more halogen atoms; halogen; $C_6$-$C_{14}$ aryl; —($C_0$-$C_4$ alkyl)-3 to 14 membered heterocyclyl, wherein the heterocyclyl contains at least one heteroatom selected from N, O and S; and $NR^{11}R^{12}$, wherein the aryl and heterocyclyls are each optionally substituted by one or more Z substituents.

In a further embodiment of Formula II of the invention wherein, $R^1$ is $C_1$-$C_4$ alkyl optional substituted by one or more halogen atoms, $C_1$-$C_4$ alkoxy optionally substituted by one or more halogen atoms; halogen; $C_6$ aryl; or 6 membered heterocyclyl, wherein the heterocyclyl contains at least one heteroatom selected from N, O and S, wherein the aryl and heterocyclyls are each optionally substituted by one or more Z substituents.

In a further embodiment of Formula II of the invention wherein, $R^1$ is $C_1$-$C_4$ alkyl optional substituted by one or more halogen atoms, $C_1$-$C_4$ alkoxy optionally substituted by one or more halogen atoms; or halogen.

In a further embodiment of Formula II of the invention herein, $R^3$ is H or methyl.

In a further embodiment of Formula II of the invention herein, $R^{4a}$ is H

In an embodiment of Formula II of the invention as described anywhere herein, X is

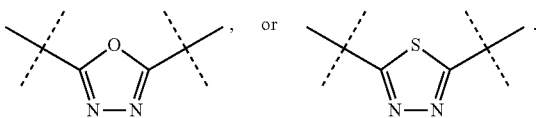, or

In an embodiment of Formula II of the invention as described anywhere herein, X is

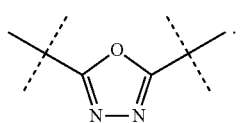

In an embodiment of Formula II of the invention as described anywhere herein, X is

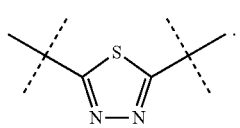

An embodiment of the invention as defined above provides compounds according to Formula II, wherein
A is $CR^{4a}$;
$R^1$ is halogen;
$R^{4a}$ is H;
$R^{101}$ is

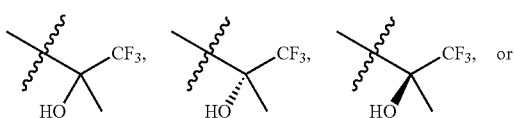

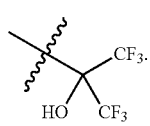

An embodiment of the invention as defined above provides compounds according to Formula II, wherein
A is $CR^{4a}$;
$R^1$ is $C_1$-$C_4$ alkyl optionally substituted by one or more halogen atoms;
$R^{4a}$ is H;
$R^{101}$ is

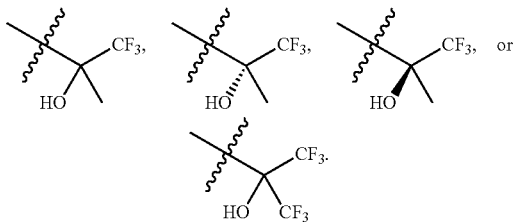

An embodiment of the invention as defined above provides compounds according to Formula II, wherein
$CR^{4a}$;
$R^1$ is $C_1$-$C_4$ alkoxy optionally substituted by one or more halogen atoms;
$R^{4a}$ is H;
$R^{101}$ is

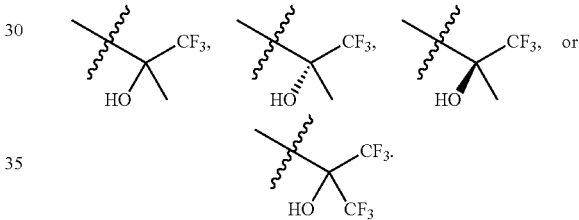

An embodiment of the invention as defined above provides compounds according to Formula II, wherein
A is $CR^{4a}$;
$R^1$ is halogen, $C_1$-$C_4$ alkyl optionally substituted by one or more halogen atoms, or $C_1$-$C_4$ alkoxy optionally substituted by one or more halogen atoms;
$R^{4a}$ is H;
$R^{101}$ is

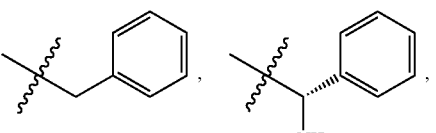

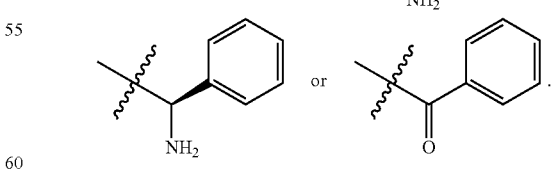

An embodiment of the invention as defined above provides compounds according to Formula II, wherein
A is $CR^{4a}$;
$R^1$ is halogen, $C_1$-$C_4$ alkyl optionally substituted by one or more halogen atoms, or $C_1$-$C_4$ alkoxy optionally substituted by one or more halogen atoms;

$R^{4a}$ is H;
$R^{101}$ is

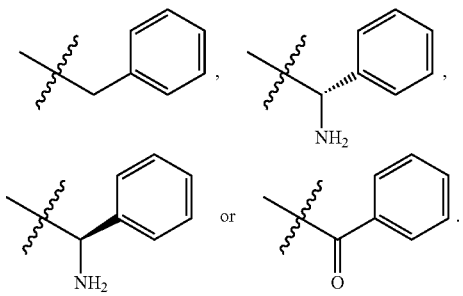

An embodiment of the invention as defined above provides compounds according to Formula II, wherein
A is $CR^{4a}$;
$R^1$ is halogen, $C_1$-$C_4$ alkyl optionally substituted by one or more halogen atoms, or $C_1$-$C_4$ alkoxy optionally substituted by one or more halogen atoms;
$R^{4a}$ is H;
$R^{101}$ is

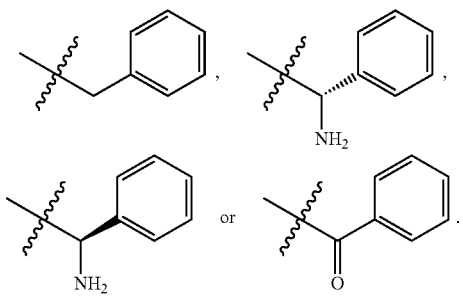

Another embodiment of the invention as defined above provides compounds according to Formula I and Formula II, or a pharmaceutically acceptable salt thereof, represented by
2-(5-(3-Amino-6-methoxy-5-(trifluoromethyl)pyridin-2-yl)-1,3,4-oxadiazol-2-yl)-1,1,1-trifluoropropan-2-ol (racemic);
(R)-2-(5-(3-amino-6-methoxy-5-(trifluoromethyl)pyridin-2-yl)-1,3,4-oxadiazol-2-yl)-1,1,1-trifluoropropan-2-ol;
(S)-2-(5-(3-amino-6-methoxy-5-(trifluoromethyl)pyridin-2-yl)-1,3,4-oxadiazol-2-yl)-1,1,1-trifluoropropan-2-ol;
3-(5-Benzyl-1,3,4-oxadiazol-2-yl)-5-bromo-6-(trifluoromethyl)pyrazin-2-amine;
(5-(3-Amino-6-bromo-5-(trifluoromethyl)pyrazin-2-yl)-1,3,4-oxadiazol-2-yl)(phenyl)methanone;
2-(5-(3-Amino-5,6-bis(trifluoromethyl)pyrazin-2-yl)-1,3,4-oxadiazol-2-yl)-1,1,1-trifluoropropan-2-ol;
2-(5-(3-Amino-5,6-bis(trifluoromethyl)pyrazin-2-yl)-1,3,4-oxadiazol-2-yl)-1,1,1-trifluoropropan-2-ol (racemic);
(R)-2-(5-(3-Amino-5,6-bis(trifluoromethyl)pyrazin-2-yl)-1,3,4-oxadiazol-2-yl)-1,1,1-trifluoropropan-2-ol;
(S)-2-(5-(3-Amino-5,6-bis(trifluoromethyl)pyrazin-2-yl)-1,3,4-oxadiazol-2-yl)-1,1,1-trifluoropropan-2-ol;
2-(5-Benzyl-1,3,4-oxadiazol-2-yl)-6-bromo-5-(trifluoromethyl)pyridin-3-amine;
2-(5-Benzyl-[1,3,4]oxadiazol-2-yl)-5-trifluoromethyl-pyridin-3-yl-amine;
2-[5-(4-Fluoro-benzyl)-[1,3,4]oxadiazol-2-yl]-5-trifluoromethyl-pyridin-3-yl-amine;
6-Bromo-2-[5-(4-fluoro-benzyl)-[1,3,4]oxadiazol-2-yl]-5-trifluoromethyl-pyridin-3-ylamine;
6-Bromo-2-[5-(2,2,2-trifluoro-ethyl)-[1,3,4]oxadiazol-2-yl]-5-trifluoromethyl-pyridin-3-ylamine;
2-(5-(3-Amino-6-cyclopropyl-5-(trifluoromethyl)pyridin-2-yl)-1,3,4-oxadiazol-2-yl)-1,1,1-trifluoropropan-2-ol;
2-(5-(3-amino-6-methyl-5-(trifluoromethyl)pyridin-2-yl)-1,3,4-oxadiazol-2-yl)-1,1,1-trifluoropropan-2-ol;
2-(5-(3-amino-6-bromo-5-(trifluoromethyl)pyridin-2-yl)-1,3,4-oxadiazol-2-yl)-1,1,1-trifluoropropan-2-ol;
2-(5-(3-Amino-5-(trifluoromethyl)pyridin-2-yl)-1,3,4-oxadiazol-2-yl)-1,1,1-trifluoropropan-2-ol;
(2-(5-(3-amino-5-(trifluoromethyl)pyridin-2-yl)-1,3,4-oxadiazol-2-yl)-1,1,1-trifluoropropan-2-ol (racemic).
(R)-2-(5-(3-amino-5-(trifluoromethyl)pyridin-2-yl)-1,3,4-oxadiazol-2-yl)-1,1,1-trifluoropropan-2-ol;
(S)-2-(5-(3-amino-5-(trifluoromethyl)pyridin-2-yl)-1,3,4-oxadiazol-2-yl)-1,1,1-trifluoropropan-2-ol;
2-(5-(3-Amino-6-bromo-5-(trifluoromethyl)pyridin-2-yl)-1,3,4-oxadiazol-2-yl)propan-2-ol;
(R)-2-(5-(amino(phenyl)methyl)-1,3,4-oxadiazol-2-yl)-6-bromo-5-(trifluoro methyl)pyridin-3-amine; and
2-(5-(3-Amino-5-(trifluoromethyl)pyridin-2-yl)-1,3,4-thiadiazol-2-yl)-1,1,1-trifluoro propan-2-ol.
(R)-2-[5-(3-Amino-4-chloro-6-methoxy-5-trifluoromethyl-pyridin-2-yl)-[1,3,4]oxadiazol-2-yl]-1,1,1-trifluoro-propan-2-ol;
(S)-2-(5-(3-Amino-4-chloro-6-methoxy-5-(trifluoromethyl)pyridin-2-yl)-1,3,4-oxadiazol-2-yl)-1,1,1-trifluoropropan-2-ol;
(S)-2-[5-(3-Amino-4-ethyl-6-methoxy-5-trifluoromethyl-pyridin-2-yl)-[1,3,4]oxadiazol-2-yl]-1,1,1-trifluoro-propan-2-ol;
(S)-2-[5-(3-Amino-4-isopropenyl-6-methoxy-5-trifluoromethyl-pyridin-2-yl)-[1,3,4]oxadiazol-2-yl]-1,1,1-trifluoro-propan-2-ol;
(S)-2-[5-(3-Amino-4-isopropyl-6-methoxy-5-trifluoromethyl-pyridin-2-yl)-[1,3,4]oxadiazol-2-yl]-1,1,1-trifluoro-propan-2-ol; and
(S)-2-[5-(3-Amino-6-methoxy-4-phenyl-5-trifluoromethyl-pyridin-2-yl)-[1,3,4]oxadiazol-2-yl]-1,1,1-trifluoro-propan-2-ol.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Especially preferred specific compounds of formula (I) or formula II are those described hereinafter in the Examples.

DEFINITIONS

Terms used in the specification have the following meanings:

"Optionally substituted" means the group referred to can be substituted at one or more positions by any one or any combination of the radicals listed thereafter.

"Optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_8$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-Alkyl" will represent methyl, ethyl, propyl, isopropyl, butyl, isobutyl, sec-butyl and tert-butyl.

"$C_1$-$C_8$-Alkoxy", as used herein, denotes straight chain or branched alkoxy having 1-8 carbon atoms. If a different number of carbon atoms is specified, such as $C_6$ or $C_3$, then the definition is to be amended accordingly, such as "$C_1$-$C_4$-Alkoxy" will represent methoxy, ethoxy, propoxy, isopropoxy, butoxy, isobutoxy, sec-butoxy and tert-butoxy.

"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $(CF_3)_2CH-$, $CH_3-CF_2-$, $CF_3CF_2-$, $CF_3$, $CF_2H-$, $CF_3CF_2CHCF_3$ or $CF_3CF_2CF_2CF_2-$.

"$C_1$-$C_8$-hydroxyalkyl", as used herein, denotes straight chain or branched alkyl having 1-8 carbon atoms with at least one hydrogen substituted with a hydroxy group. If a different number of carbon atoms is specified, such as $C_6$ or $C_3$, then the definition is to be amended accordingly, such as "$C_1$-$C_4$-hydroxyalkyl" will represent methyl, ethyl, propyl, isopropyl, butyl, isobutyl, sec-butyl and tert-butyl that have at least one hydrogen substituted with a hydroxy group.

The term '$C_{2-8}$ alkenyl' as used herein refers to a linear or branched saturated hydrocarbon group containing from 2 to 8 carbon atoms that contains at least one carbon to carbon double bond. Examples of such groups include ethenyl, propenyl, butenyl and pentenyl. Unless a particular structure is specified, the terms butenyl and pentenyl etc. include all possible E and Z isomers.

The term '$C_{3-8}$ cycloalkyl' as used herein refers to a saturated monocyclic hydrocarbon ring of 3 to 6 carbon atoms. Examples of such groups include cyclopropyl, cyclobutyl, cyclopentyl and cyclohexyl.

The term "alkylene" denotes a straight chain or branched saturated hydrocarbon chain containing between 1 and 8 carbon atoms. If a different number of carbon atoms is specified, such as $C_6$ or $C_3$, then the definition is to be amended accordingly. "Amino-$C_1$-$C_8$-alkyl" and "amino-$C_1$-$C_8$-alkoxy" denote amino attached by a nitrogen atom to $C_1$-$C_8$-alkyl, e.g., $NH_2-(C_1-C_8)-$, or to $C_1$-$C_8$-alkoxy, e.g., $NH_2-(C_1-C_8)-O-$. If a different number of carbon atoms is specified, such as $C_6$ or $C_3$, then the definition is to be amended accordingly.

"$C_1$-$C_8$-Alkylamino" and "di($C_1$-$C_8$-alkyl)amino" denote $C_1$-$C_8$-alkyl, as hereinbefore defined, attached by a carbon atom to an amino group. The $C_1$-$C_8$-alkyl groups in di($C_1$-$C_8$-alkyl)amino may be the same or different. If a different number of carbon atoms is specified, such as $C_6$ or $C_3$, then the definition is to be amended accordingly.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl. If a different number of carbon atoms is specified, such as $C_6$ or $C_3$, then the definition is to be amended accordingly.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined, attached by a carbon atom to a carbonyl group. If a different number of carbon atoms is specified, such as $C_6$ or $C_3$, then the definition is to be amended accordingly.

"$C_3$-$C_8$-Cycloalkylcarbonyl", as used herein, denotes $C_3$-$C_8$-cycloalkyl, as hereinbefore defined, attached by a carbon atom to a carbonyl group. If a different number of carbon atoms is specified, such as $C_6$ or $C_3$, then the definition is to be amended accordingly.

"$C_7$-$C_{14}$-Aralkyl", as used herein, denotes alkyl, e.g., $C_1$-$C_4$-alkyl, as hereinbefore defined, substituted by a $C_6$-$C_{10}$-aromatic carbocyclic group, as herein defined. If a different number of carbon atoms is specified, such as $C_6$ or $C_3$, then the definition is to be amended accordingly.

"$C_3$-$C_{15}$-Cycloalkyl", as used herein, denotes a cycloalkyl having 3- to 15-ring carbon atoms that is saturated or partially saturated, such as a $C_3$-$C_8$-cycloalkyl. Examples of $C_3$-$C_{15}$-cycloalkyls include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl. If a different number of carbon atoms is specified, such as $C_6$, then the definition is to be amended accordingly.

"aryl" or "$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_{10}$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclyl includes single ring groups, fused ring groups and bridged groups. Examples of such heterocyclyls include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahyrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane or thiazole.

A second aspect of the invention provides a compound of Formula I or II as defined anywhere herein for use as a pharmaceutical.

A further aspect of the invention provides a compound of Formula I or II for use in the treatment of an inflammatory or allergic condition, particularly an inflammatory or obstructive airways disease or mucosal hydration. Such conditions include, for example, cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

A still further aspect of the present invention provides for the use of a compound of formula (I) or (II), as defined in any of the aforementioned embodiments, in free or pharmaceutically acceptable salt form, for the manufacture of a medicament for the treatment of an inflammatory or allergic condition, particularly an inflammatory or obstructive airways disease or mucosal hydration.

An embodiment of the present invention provides for the use of a compound of formula (I) or (II), as defined in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

An embodiment of the present invention provides for the use of a compound of formula (I) or (II), as defined in any of the aforementioned embodiments, in free or pharmaceutically acceptable salt form, for the manufacture of a medicament for the treatment of an inflammatory or allergic condition which is cystic fibrosis.

An embodiment of the present invention provides method for the prevention or treatment of a CFTR mediated condition or disease comprising administering an effective amount of at least one compound as described herein to a subject in need of such treatment. Such CFTR mediated condition or disease are selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, and sulfosalicylic acid.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates, or include other solvents used for their crystallization.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans- configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Compounds of the present invention are either obtained in the free form, or as a salt thereof.

When both a basic group and an acid group are present in the same molecule, the compounds of the present invention may also form internal salts, e.g., zwitterionic molecules.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}F$, $^{32}F$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I) or (II). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) or (II) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) or formula (II) that contain groups capable of acting as donors and/or acceptors for hydrogen bonds may be capable of forming co-crystals with suitable co-crystal formers. These co-crystals may be prepared from compounds of formula (I) or formula (II) by known co-crystal forming procedures. Such procedures include grinding, heating, co-subliming, co-melting, or contacting in solution compounds of formula (I) or formula (II) with the co-crystal former under crystallization conditions and isolating co-crystals thereby formed. Suitable co-crystal formers include those described in WO 2004/078163. Hence the invention further provides co-crystals comprising a compound of formula (I) or formula (II).

Synthesis

Generally, compounds according to Formula I or (II) can be synthesized by the routes described in Scheme 1, to 18 and the Examples.

When A is CR4a and R4a is alkyl, aryl or heteroaryl, compounds may be synthesized according to general scheme 1

Scheme 1

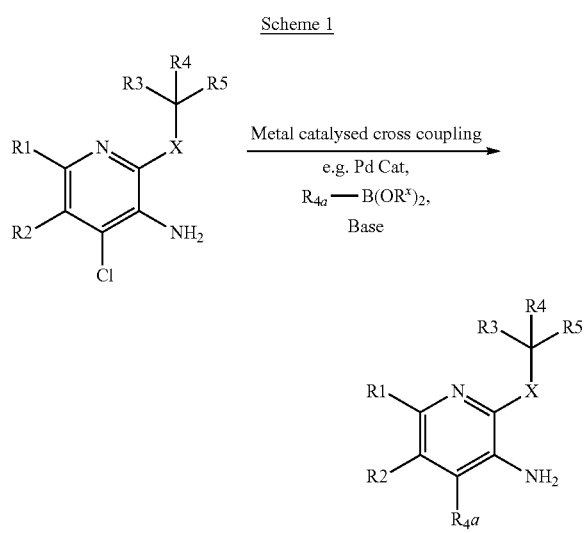

When R1 is alkyl or aryl and A is N or CH, compounds may be synthesized according to scheme 2. $B(OR^x)_2$ refers to a boronic acid or boronate ester coupling agent.

Scheme 2

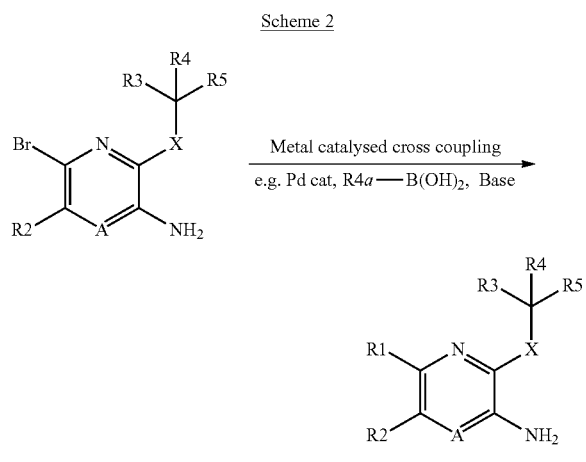

When R1 is alkyl amino, A is N or CH, compounds may be synthesized according to scheme 3.

Scheme 3

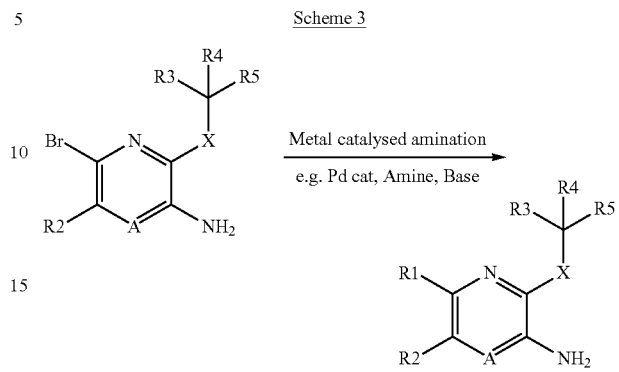

Buchwald conditions are suitable for the metal catalysed amination and are known to skilled artisans.

When R1 is carboxamide and A is CH, compounds may be synthesized according to scheme 4.

Scheme 4

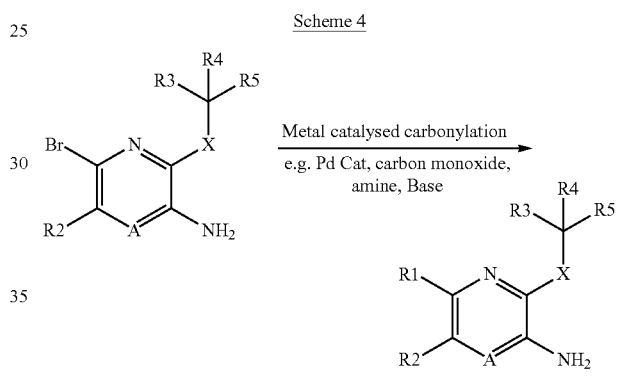

Alternative reagents to carbon monoxide gas such as $Mo(CO)_9$ may also work.

In schemes 1-4, a suitable palladium catalyst such as [1,1'-bis(di-tertbutylphospino)ferrocene]dichloropalladium(II) may be used. A person skilled in the art would understand that other palladium catalysts may also work.

When X is oxadiazole, compounds may be synthesized according to the general scheme 5 below.

Scheme 5

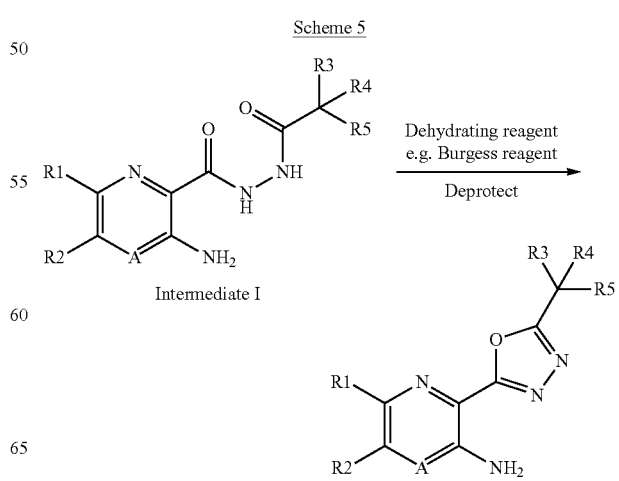

A suitable dehydrating agent is the Burgess reagent or triphenylphosphine/hexachloroethane. A person skilled in the art would understand that other dehydrating agents may also work.

When X is thiadiazole compounds may be synthesized according to the general scheme 6 shown below.

Scheme 6

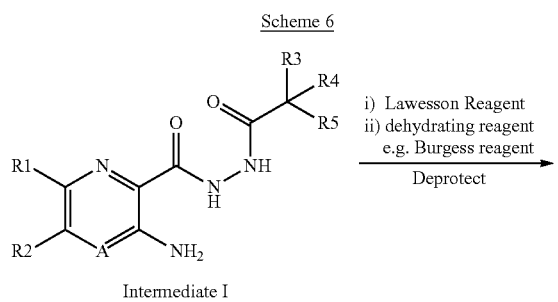

Intermediate I

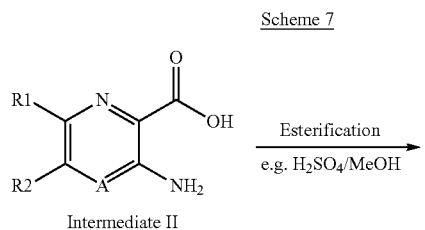

Intermediate I may be synthesized by the method shown in scheme 7 or scheme 8

Scheme 7

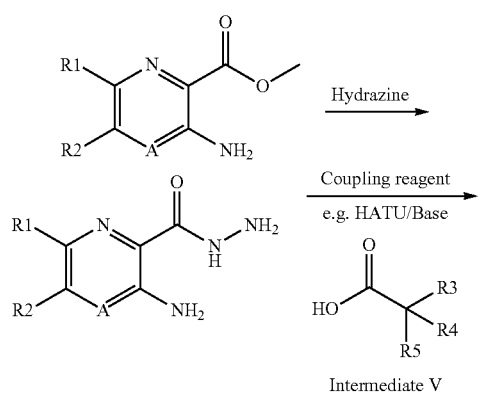

Intermediate V

-continued

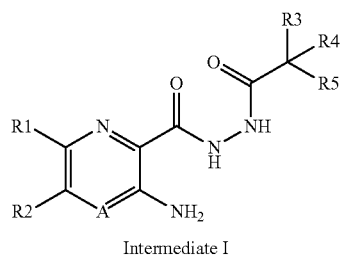

Intermediate I

Or alternatively

Scheme 8

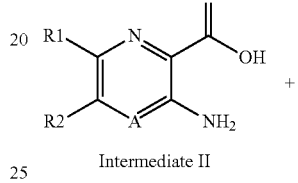

Intermediate II

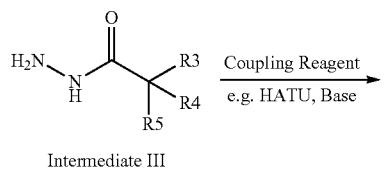

Intermediate III

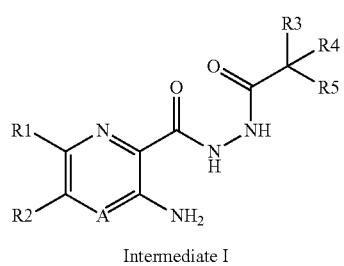

Intermediate I

The carboxylic acid, intermediate V, is either available commercially, or has a published synthesis.

Intermediate III can be synthesized according to the general scheme 9

Scheme 9

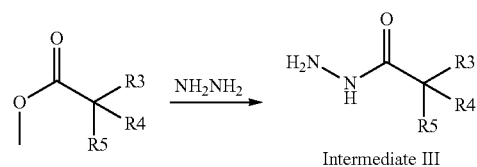

Intermediate III

The carboxylate ester is obtained by esterification of intermediate V using methods known to a person skilled in the art.

When R1 is halogen and A is CH, Intermediate II can be synthesized according to the general scheme 10

Scheme 10

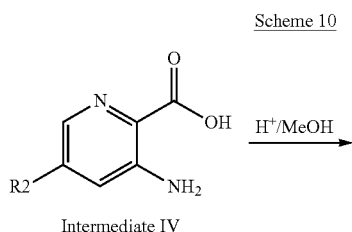

Intermediate IV

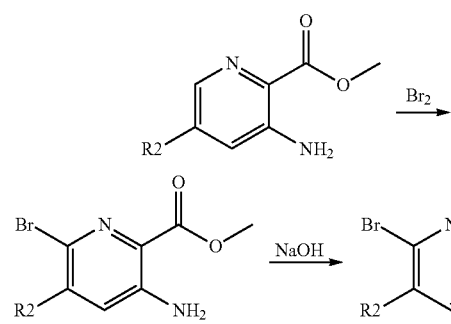

When R1 is halogen, A is CR4a and R4a is halogen, intermediate II can be synthesized according to scheme 11.

Scheme 11

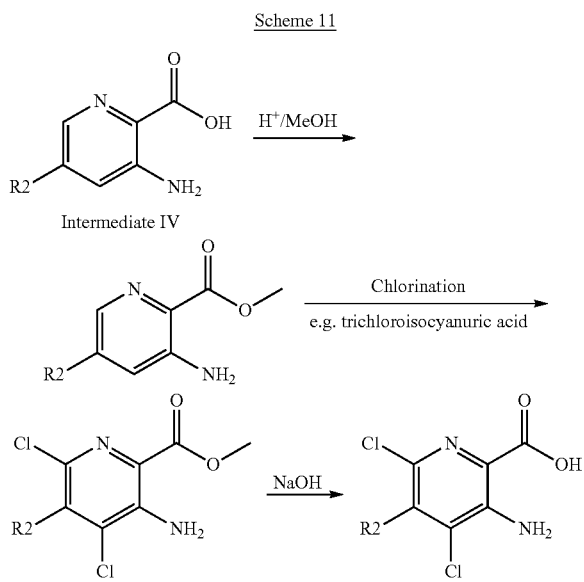

When R1 is methoxy and A is CH, Intermediate II can be synthesized according to the general scheme 12.

Scheme 12

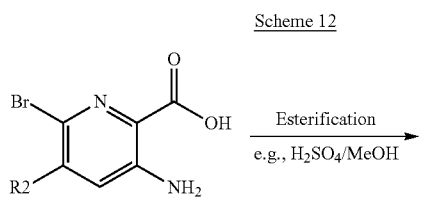

-continued

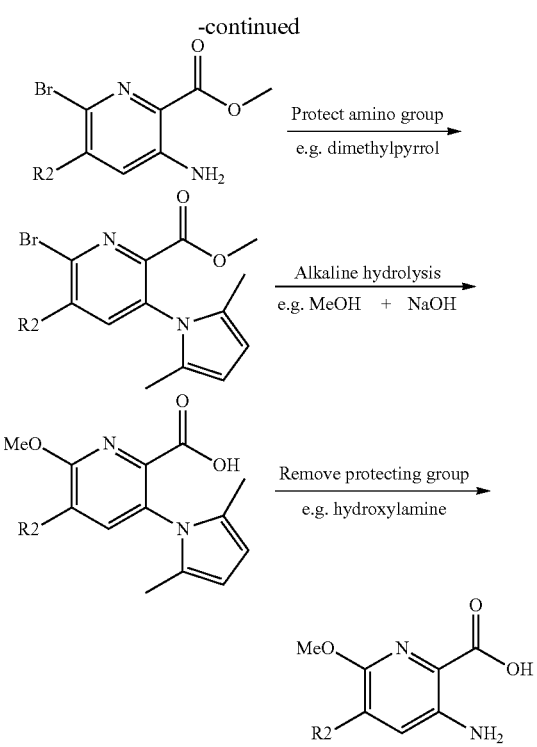

When R1 is alkyloxy and A is CH, Intermediate II can be synthesized according to the general scheme 13.

Scheme 13

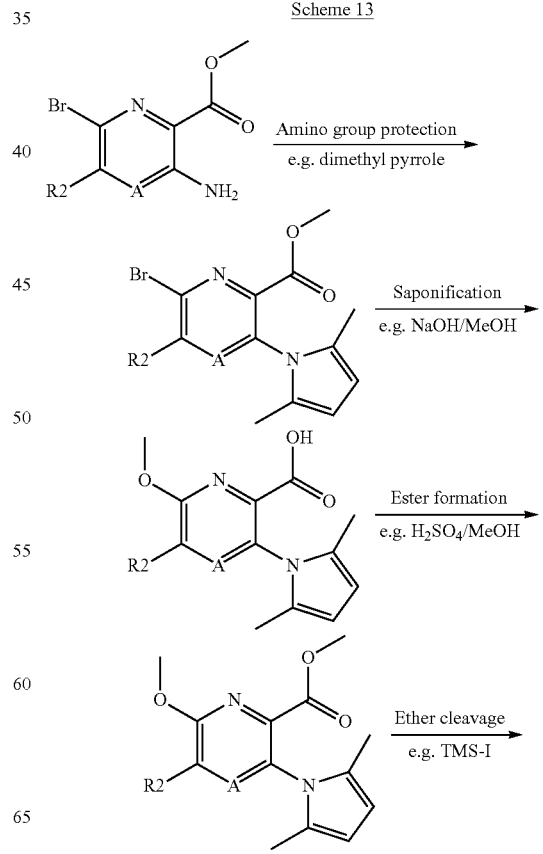

-continued

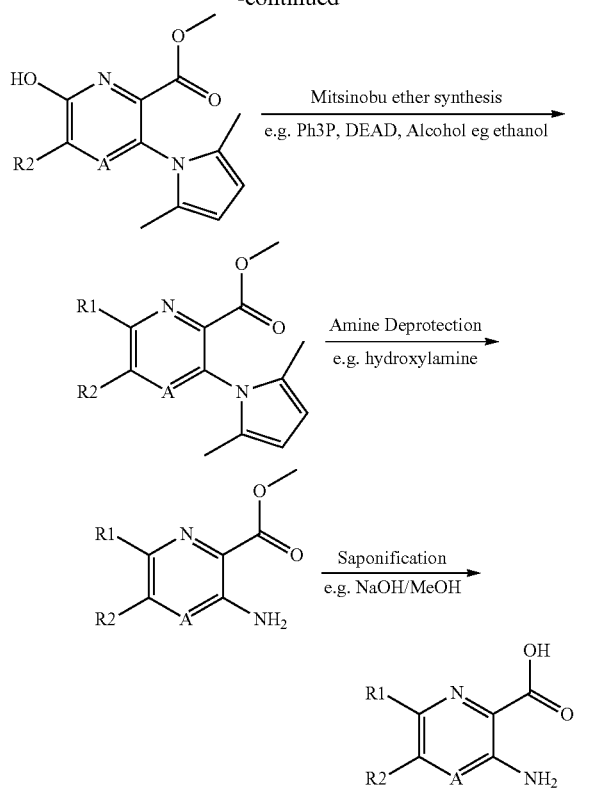

When R1 is alkoxy, A is CR4a and R4a is halogen, Intermediate II can be synthesized according to the general scheme 14.

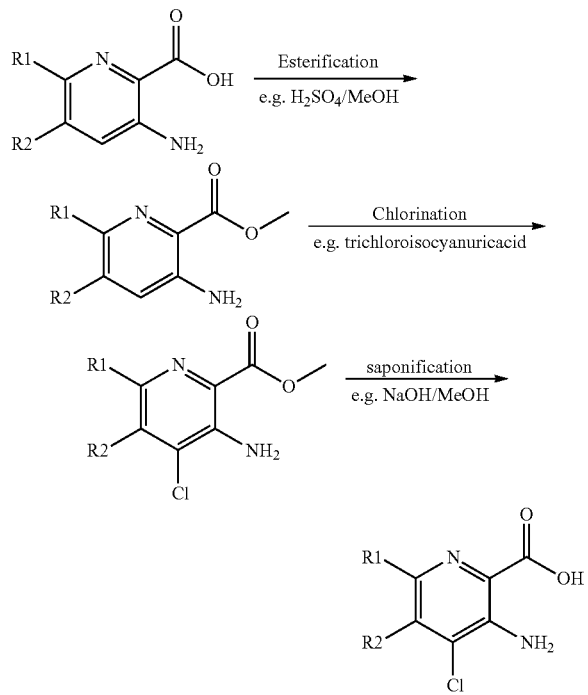

When R1 is Alkyl, aryl or heteroaryl and A is CH, Intermediate II can be synthesized according to the general scheme 15

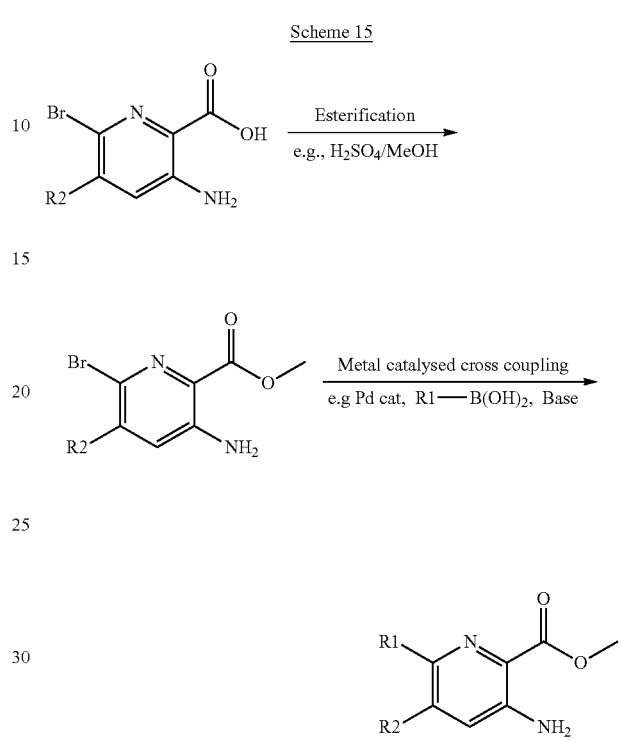

A suitable palladium catalyst to use is [1,1'-bis(di-tertbutylphospino)ferrocene]dichloropalladium(II). A person skilled in the art would understand that other palladium catalysts may also work.

When R1 is halogen and A is nitrogen, Intermediate II can be synthesized according to the general scheme 16

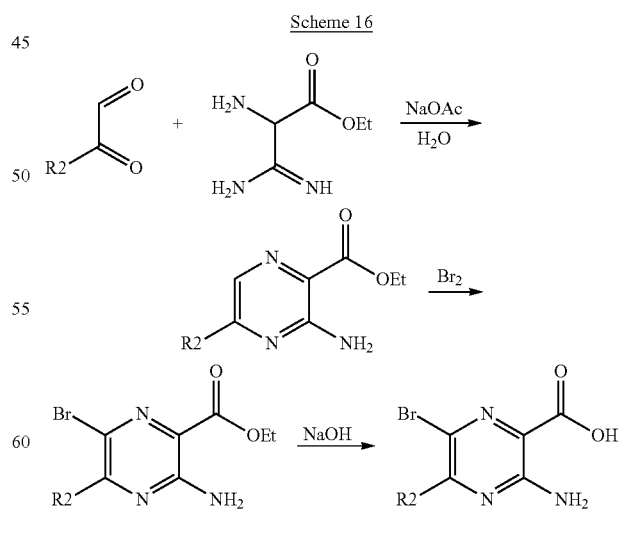

Intermediate IV can be synthesized according to the general scheme 17 or scheme 18

Scheme 17.

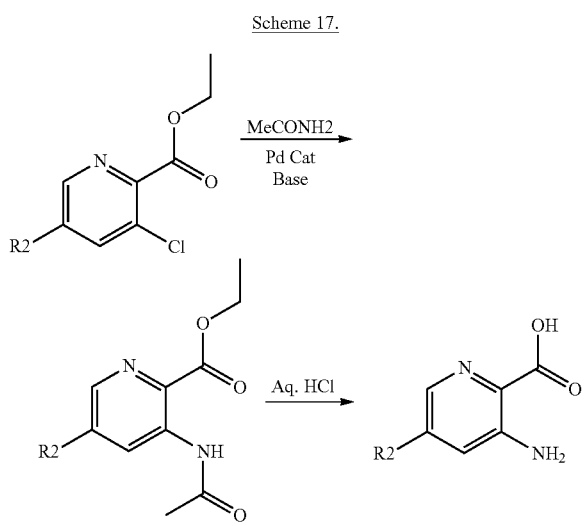

Or alternatively

Scheme 18

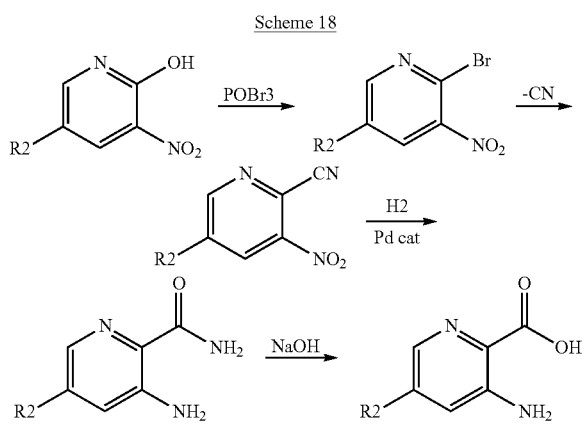

The skilled person will appreciate that the general synthetic routes detailed above show common reactions to transform the starting materials as required. The specific reaction conditions are not provided, but these are well known to those skilled in the art and appropriate conditions considered to be within the skilled person's common general knowledge.

The starting materials are either commercially available compounds or are known compounds and can be prepared from procedures described in the organic chemistry art.

Compounds of formula (I) or (II), in free form, may be converted into salt form, and vice versa, in a conventional manner understood by those skilled in the art. The compounds in free or salt form can be obtained in the form of hydrates or solvates containing a solvent used for crystallisation. Compounds of formula (I) or (II) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of formula (I) or (II) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) or (II) into another compound of formula (I) or (II). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5$^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

Pharmacological Activity

Having regard to their modulation of CFTR activity, compounds of formula (I), in free or pharmaceutically acceptable salt form, hereinafter alternately referred to as "agents of the invention", are useful in the treatment of conditions which respond to the modulation of CFTR activity, particularly conditions benefiting from mucosal hydration such as cystic fibrosis.

Diseases mediated by modulation of CFTR activity, include diseases associated with the regulation of fluid volumes across epithelial membranes. For example, the volume of airway surface liquid is a key regulator of mucociliary clearance and the maintenance of lung health. The modulation of CFTR activity will promote fluid accumulation on the mucosal side of the airway epithelium thereby promoting mucus clearance and preventing the accumulation of mucus and sputum in respiratory tissues (including lung airways).

Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by modulation of CFTR activity also include diseases other than respiratory diseases that are associated with abnormal fluid regulation across an epithelium, perhaps involving abnormal physiology of the protective surface liquids on their surface, e.g., Sjögren's Syndrome, xerostomia (dry mouth) or keratoconjunctivitis sire (dry eye). Furthermore, modulation of CFTR activity in the kidney could be used to promote diuresis and thereby induce a hypotensive effect.

Treatment in accordance with the invention may be symptomatic or prophylactic.

Asthma includes intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvements in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

Dry eye disease is characterized by a decrease in tear aqueous production and abnormal tear film lipid, protein and mucin profiles. There are many causes of dry eye, some of which include age, laser eye surgery, arthritis, medications, chemical/thermal burns, allergies and diseases, such as cystic fibrosis and Sjögren's Syndrome. Increasing anion secretion via CFTR would enhance fluid transport from the corneal endothelial cells and secretory glands surrounding the eye to increase corneal hydration. This would help to alleviate the symptoms associated with dry eye disease.

Sjögren's Syndrome is an autoimmune disease in which the immune system attacks moisture-producing glands throughout the body, including eye, mouth, skin, respiratory tissue, liver, vagina and gut. Symptoms include dry eye, dry mouth and dry vagina, as well as lung disease. The disease is also associated rheumatoid arthritis, systemic lupus, systemic sclerosis and polymypositis/dermatomyositis. Defective protein trafficking is believed to cause the disease, for which treatment options are limited. Modulators of CFTR activity may hydrate the various organs affected by the disease and help to alleviate the associated symptoms.

The suitability of CFTR activity modulators as a treatment of a disease benefiting from mucosal hydration may be tested by determining the movement of chloride ions in a suitable cell-based assay. For example single cells or confluent epithelia, endogenously expressing or engineered to overexpress CFTR can be used to assess channel function using electrophysiological techniques or ion flux studies. See methods described in: Hirsh et al., *J Pharm Exp Ther* (2004); Moody et al., *Am J Physiol Cell Physiol* (2005).

CFTR activity modulators, including the compounds of formula (I), are also useful as co-therapeutic agents for use in combination with other drug substances, such as anti-inflammatory, bronchodilatory, antihistamine or anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

The compounds of Formula (I) or (II) may be mixed with the other drug substance in a fixed pharmaceutical composition or it may be administered separately, before, simultaneously with or after the other drug substance.

Accordingly, the invention includes as a further aspect a combination of a CFTR activity modulator with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the CFTR activity modulator and the further drug substance may be in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of CFTR activity modulators with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol or pharmaceutically acceptable salts thereof, and compounds (in free or salt or solvate form) of formula (I) of WO 0075114, which document is incorporated herein by reference, preferably compounds of the Examples thereof, especially a compound of formula:

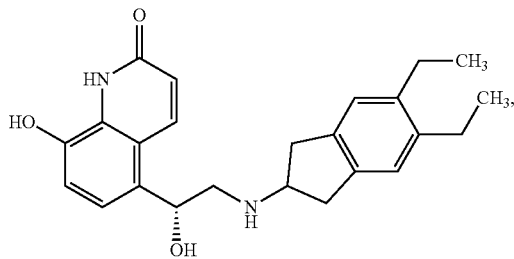 [SMILES: CCc1cc2c(cc1CC)CC(NC[C@H](O)c1ccc(O)c3[nH]c(=O)ccc13)C2]

corresponding to indacaterol or pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

The invention includes as a further aspect a combination of a CFTR activity modulator with a CFTR corrector, wherein the CFTR activity modulator and the CFTR corrector may be in the same or different pharmaceutical composition. Suitable CFTR correctors include VX-809

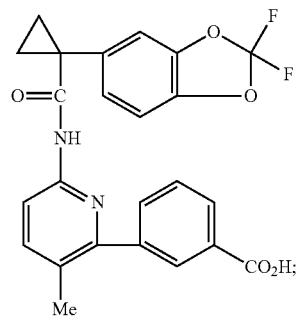

and
VX-661

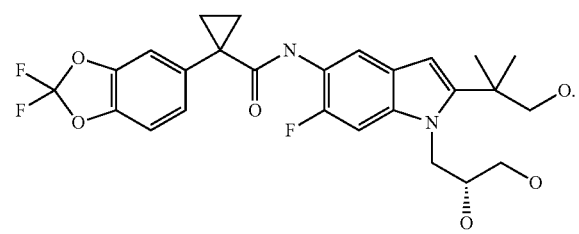

In accordance with the foregoing, the invention also provides as a further aspect a method for the treatment of a condition responsive to modulation of CFTR activity, e.g., diseases associated with the regulation of fluid volumes across epithelial membranes, particularly an obstructive airways disease, which comprises administering to a subject, particularly a human subject, in need thereof a compound of formula (I) or (II), in free form or in the form of a pharmaceutically acceptable salt.

In another aspect the invention provides a compound of formula (I) or (II), in free form or in the form of a pharmaceutically acceptable salt, for use in the manufacture of a medicament for the treatment of a condition responsive to modulation of CFTR activity, particularly an obstructive airways disease, e.g., cystic fibrosis and COPD.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula (I), in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I) or (II) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) or (II) either dissolved, or suspended, in a vehicle containing water, a co-solvent, such as ethanol or propylene glycol and a stabilizer, which may be a surfactant.

Further aspects of the invention include:
(a) a compound of formula (I) or (II) in inhalable form, e.g., in an aerosol or other atomisable composition or in inhalable particulate, e.g., micronised form;
(b) an inhalable medicament comprising a compound of formula (I) or (II) in inhalable form;
(c) a pharmaceutical product comprising a compound of formula (I) in inhalable form in association with an inhalation device; and
(d) an inhalation device containing a compound of formula I or II in inhalable form.

Dosages of compounds of formula (I) or (II) employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of formula (I) or (II) and their pharmaceutically acceptable salts, hereinafter referred to alternatively as "agents of the invention", are useful as pharmaceuticals. In particular, the compounds are suitable CFTR activity modulators and may be tested in the following assays.

Membrane Potential Assay

CFTR activity can be quantified by measuring the transmembrane potential. The means for measuring the transmembrane potential in a biological system can employ a number of methods including electrophysiological and optical fluorescence-based membrane potential assays.

The optical membrane potential assay utilises a negatively charged potentiometric dye, such as the FLIPR membrane potential dye (FMP) (see Baxter D F, Kirk M, Garcia A F, Raimondi A, Holmqvist M H, Flint K K, Bojanic D, Distefano P S, Curtis R, Xie Y. 'A novel membrane potential-sensitive fluorescent dye improves cell-based assays for ion channels.' J Biomol Screen. 2002 February; 7(1):79-85) which when extracellular is bound to a quenching agent. Upon cellular depolarisation the negatively charged dye redistributes to the intracellular compartment, unbinding from the membrane impermeant quench agent, yielding an increase in fluorescence. This change in fluorescence is proportional to the change in transmembrane potential which can result from the activity of CFTR. The changes in fluorescence can be monitored in real time by an appropriately equipped fluorescence detector such as the FLIPR (fluorometric imaging plate reader) in 96 or 384-well microtitre plates.

Cell Culture:

Chinese hamster ovary (CHO) cells stably expressing the F508-CFTR channel were used for membrane potential experiments. Cells were maintained at 37° C. in 5% v/v $CO_2$ at 100% humidity in Modified Eagles medium (MEM) supplemented with 8% v/v foetal calf serum, 100 µg/ml methotrexate and 100 U/ml penicillin/streptomycin. Cells were grown in 225 $cm^2$ tissue culture flasks. For membrane potential assays cells were seeded into 96 well plates at 40,000 cells per well, allowed to adhere and then maintained at 26° C. for 48 h to facilitate channel insertion.

Potentiator Assay:

The membrane potential screening assay utilised a low chloride ion containing extracellular solution (~5 mM) combined with a double addition protocol. The first addition was of buffer with or without test compound followed 5 minutes later by an addition of forskolin (1-20 µM)—this protocol favours maximum chloride efflux in response to F508-CFTR activation. The F508-CFTR mediated chloride ion efflux leads to a membrane depolarisation which is optically monitored by the FMP dye.

Solutions:

Low chloride extracellular (mM): 120 Na-gluconate, 1.2 $CaCl_2$, 3.3 $KH_2PO_4$, 0.8 $K_2HPO_4$, 1.2 $MgCl_2$, 10.0 D-glucose, 20.0 HEPES, pH 7.4 with NaOH FMP dye: made up as per manufacturers' instructions in low chloride extracellular solution detailed above, at 10× final concentration, and stored as 1 mL aliquots at −20° C.

IonWorks Quattro Assay:

CFTR activity can also be quantified electrophysiologically using the whole-cell configuration of the patch clamp technique (Hamill et al Pflugers Acrhive 1981). This assay directly measures the currents associated with chloride flow through CFTR channels whilst either maintaining or adjusting the transmembrane voltage. This assay can use either single glass micropipettes or parallel planar arrays to measure CFTR activity from native or recombinant cell systems. Currents measured using parallel planar arrays can be quantified using an appropriately equipped instrument such as the IonWorks Quattro (Molecular Devices) or the Qpatch (Sophion). The Quattro system can measure CFTR currents from either a single cell per recording well (HT configuration) or alternatively from a population of 64 cells per well (Population Patch Clamp PPC) (Finkel A, Wittel A, Yang N, Handran S, Hughes J, Costantin J. 'Population patch clamp improves data consistency and success rates in the measurement of ionic currents.' J Biomol Screen. 2006 August; 11(5):488-96).

Cell Culture:

Chinese hamster ovary (CHO) cells stably expressing the F508-CFTR channel were used for IonWorks Quattro experiments. Cells were maintained at 37° C. in 5% v/v $CO_2$ at 100% humidity in D-MEM supplemented with 10% (v/v) FCS, 100 U/mL Penicillin/Streptomycin, 1% (v/v) NEAA, 1 mg/ml Zeocin and 500 ug/ml Hygromycin B. For experiments cells were grown in 225 $cm^2$ tissue culture flasks until near confluence and then cultured at 26° C. for 48-72 h to facilitate channel insertion. Cells were removed from the flask and resuspended in either extracellular recording solution for immediate experimentation or alternatively in growth medium supplemented with 10% v/v DMSO and frozen to −80° C. as 1-2 mL aliquots for use at a later date.

Potentiator Assay:

Cells, at a density of 1.5-3 million per mL, were placed on the Quattro system, added to the planar patch array and seals allowed to establish for 5-10 mins. After assessing seal resistances (commonly >50 M), whole-cell access was obtained by perforation with 100 μg/mL amphotericin B. Baseline currents were measured by a pre-compound scan obtained by application of a voltage ramp from −100 to +100 mV. This was followed by addition of either buffer or test compound diluted in the extracellular solution supplemented with 20 μM forskolin, to each of the 384 wells of the planar parch array. After incubation step (5-20 minutes) the post-compound currents were measured again by application of a voltage ramp from −100 to +100 mV. The difference in currents between the pre- and post-compound scans defined the efficacy of CFTR potentiation.

Solutions:

Extracellular solution (ECS): 145 mM NaCl, 4 mM CsCl, 5 mM D-glucose, 10 mM TES, 1 mM $CaCl_2$, 1 mM $MgCl_2$, pH 7.4 NaOH Intracellular buffer (ICS): 113 mM L-Aspartic acid, 113 mM CsOH, 27 mM CsCl, 1 mM NaCl, 1 mM $MgCl_2$, 1 mM EGTA, 10 mM TES. pH 7.2 with CsOH. Filter sterilized before use.

Ion Transport Assay:

Another method to measure CFTR function is Ussings chamber short circuit current measurement. Engineered or native epithelial cells are grown to confluent monolayer on a semi-permeable filter and sandwiched between two perspex blocks. The flow of chloride ions via CFTR from one side of the epithelia to the other can be quantified by measuring the flow of current whilst maintaining the transepithelial potential at 0 mV. This is achieved using KCl filled agar-based electrodes to both clamp the cellular monolayer and measure the flow of currents.

Cell Culture:

FRT cells stably expressing ΔF508-CFTR were cultured on plastic in Coon's modified F-12 medium supplemented with 32 mM $NaHCO_3$, 10% v/v fetal bovine serum, 2 mM L-glutamine, 100 U/mL penicillin, 100 μg/mL streptomycin and 30 μg/mL hygromycin B as the growth medium. For Ussing chamber experiments, the cells were grown as polarized epithelia on Snapwell permeable support inserts (500000 cells/insert in growth medium) and cultured for 7 to 9 days. The inserts were fed with fresh Coon's modified F-12 growth medium every 48 hours, and 24 hours prior to Ussing chamber experiment. To increase the ΔF508 CFTR protein expression at the cell surface, plates were incubated at 27° C. for 48 h before performing an Ussing chamber experiment.

Potentiator Assay:

Fischer Rat Thyroid (FRT) epithelial cells, stably expressing human ΔF508-CFTR were used as monolayer cultures on permeable supports. Cl⁻ current was measured using the short circuit current technique, under an imposed basolateral to apical Cl⁻ gradient in Ussing chambers. To measure stable Cl⁻ currents, FRT cells were cultured for 48 h at 27° C. to facilitate the insertion of ΔF508 CFTR into the plasma membrane. Ussing chamber studies were likewise conducted at 27° C. Under these conditions, the effects of cumulative additions of test compounds on ΔF508 CFTR currents could be quantitated with both potency and efficacy endpoints. Compounds were added to both the apical and basloalteral sides subsequent to addition of 10 μM forskolin. Efficacy of compounds was compared to a known potentiator such as gensitein.

Solutions:

Basolateral Ringer solution (mM): 126 NaCl, 24 $NaHCO_3$, 0.38 $KH_2PO_4$, 2.13 $K_2HPO_4$, 1 $MgSO_4$, 1 $CaCl_2$ and 10 glucose.

Apical Ringer solution (mM): 140 Na-gluconate, 1 $MgSO_4$, 2 $CaCl_2$, 1 HCl, 10 glucose and 24 $NaHCO_3$.

Compounds can also be tested for their ability to stimulate insertion of ΔF508 CFTR into the cell membrane using the above assays. For these assays the protocols were identical other than cells were not cultured at low temperature (26 or 27° C.) but instead incubated with test compounds for 12-24 h prior to assay.

Compounds of the Examples, herein below, generally have $EC_{50}$ values in the data measurements described above below 10 μM. Table 1 provides a list of representative compounds with their $EC_{50}$ value.

TABLE 1

| Example No | $EC_{50}$ M | Example No | $EC_{50}$ |
|---|---|---|---|
| 1 | 0.0023829 | 10 | 0.0014 |
| 2 | 0.003408 | 10.1 | 0.013 |
| 3 | 0.00355 | 10.2 | 0.005227 |
| 4 | 0.15 | 10.3 | 0.0743833 |
| 5 | 0.0866667 | 10.4 | 0.0313 |
| 6 | 0.1845 | 10.5 | 0.127 |
| 7 | 0.0041 | 10.6 | 0.0146625 |
| 8 | 0.0021 | 11 | 0.078 |
| 9 | 0.0845 | 12 | 0.010 |

The invention is illustrated by the following Examples.

EXAMPLES

General Conditions

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H]⁺ refers to mono-isotopic molecular weights.

NMR spectra were run on open access Bruker AVANCE 400 NMR spectrometers using ICON-NMR. Spectra were measured at 298K and were referenced using the solvent peak.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

ABBREVIATIONS app apparent
BEMP 2-tert-Butylimino-2-diethylamino-1,3-dimethylperhydro-1,3,2-diazaphosphorine
boc tertiary butyl carboxy
br broad
d doublet
dd doublet of doublets
DCM dichloromethane
DIPEA diisopropylethylamine
DMF N,N-dimethylformamide
DMSO dimethylsulfoxide
EtOAc ethyl acetate
h hour(s)
HATU 2-(7-Aza-1H-benzotriazole-1-yl)-1,1,3,3-tetramethyluronium hexafluorophosphate HPLC high pressure liquid chromatography
Int. intermediate
LC-MS liquid chromatography and mass spectrometry
MeOH methanol
MS mass spectrometry
m multiplet
min minutes
ml milliliter(s)
m/z mass to charge ratio
NMR nuclear magnetic resonance
ppm parts per million
PS polymer supported
PEAX PE-anion exchange (e.g. Isolute® PE-AX columns from Biotage)
RT room temperature
Rt retention time
s singlet
SCX-2 strong cation exchange (e.g. Isolute® SCX-2 columns from Biotage)
t triplet
TEA triethylamine
TFA trifluoroacetic acid
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:

| Method 10minLC_v002 | |
|---|---|
| Column | Waters BEH C18 50 × 2.1 mm, 1.7 μm |
| Column Temperature | 50° C. |
| Eluents | A: $H_2O$, B: methanol, both containing 0.1% TFA |
| Flow Rate | 0.8 mL/min |
| Gradient | 0.20 min 5% B; 5% to 95% B in 7.80 min, 1.00 min 95% B |
| Method 10minLC_v003 | |
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 mL/min |
| Gradient | 0.20 min 5% B; 5% to 95% B in 7.80 min, 1.00 min 95% B |
| Method 2minLC_v002 | |
| Column | Waters BEH C18 50 × 2.1 mm, 1.7 μm |
| Column Temperature | 50° C. |
| Eluents | A: $H_2O$, B: methanol, both containing 0.1% TFA |
| Flow Rate | 0.8 mL/min |
| Gradient | 0.20 min 5% B; 5% to 95% B in 1.30 min, 0.25 min 95% B |
| Method 2minLC_v003 | |
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 mL/min |
| Gradient | 0.20 min 5% B; 5% to 95% B in 1.30 min, 0.25 min 95% B |
| Method HighpH_v003 | |
| Column | Waters BEH C18 50 × 2.1 mm, 1.7 m |
| Column Temperature | 50° C. |
| Eluents | A: $H_2O$, B: acetonitrile, both containing 0.1% $NH_3OH$ |
| Flow Rate | 0.8 mL/min |
| Gradient | 0.25 min 5% B; 5% to 95% B in 1.00 min, 0.25 min 95% B |

Example compounds of the present invention include:

Preparation of Final Compounds

Example 1.0

2-(5-(3-Amino-6-methoxy-5-(trifluoromethyl)pyridin-2-yl)-1,3,4-oxadiazol-2-yl)-1,1,1-trifluoropropan-2-ol

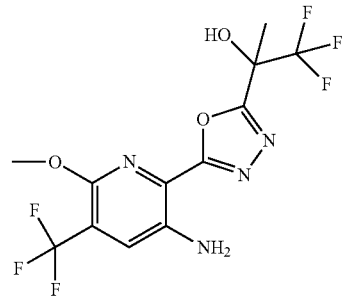 [SMILES: COc1nc(-c2nnc(C(C)(O)C(F)(F)F)o2)c(N)cc1C(F)(F)F]

Step 1: tert-butyl 2-(2-(2-(benzyloxy)-3,3,3-trifluoro-2-methylpropanoyl)hydrazine carbonyl)-6-methoxy-5-(trifluoromethyl)pyridin-3-ylcarbamate To a solution of 2-(benzyloxy)-3,3,3-trifluoro-2-methylpropanoic acid (Int. D) (0.709 g, 2.85 mmol) in DMF (15 ml) was added HATU (1.303 g, 3.43 mmol) followed by DIPEA (0.598 ml, 3.43 mmol). After 30 mins, tert-butyl 2-(hydrazinecarbonyl)-6-methoxy-5-(trifluoromethyl)pyridin-3-ylcarbamate (Int. C) (1 g, 2.85 mmol) was added and the reaction mixture was stirred at RT for 3 h. The mixture was poured into water and the product extracted with EtOAc. The organic portion was washed with 1 MHCl, brine, dried ($MgSO_4$) and concentrated in vacuo. Purification by chromatography on silica eluting with 0% to 50% EtOAc in iso-hexane afforded the title compound:

Step 2: tert-Butyl 2-(5-(2-(benzyloxy)-1,1,1-trifluoropropan-2-yl)-1,3,4-oxadiazol-2-yl)-6-methoxy-5-(trifluoromethyl)pyridin-3-ylcarbamate A stirring suspension of tert-butyl 2-(2-(2-(benzyloxy)-3,3,3-trifluoro-2-methylpropanoyl)hydrazine carbonyl)-6- methoxy-5-(trifluoromethyl)pyridin-3-ylcarbamate (step 1) (1 g, 1.723 mmol) in dry THF (20 ml) was treated with Burgess reagent (3 equiv.) and heated at reflux under $N_2$ for 1 h 45 min. The RM was reduced in vacuo to approximate volume of 5 ml and diluted with EtOAc (150 ml). The mixture was washed with 2M NaOH, 0.5M HCl, water, brine and dried ($MgSO_4$) and concentrated in vacuo. The crude product was triturated with MeOH to afford the title compound. LC-MS Rt=1.59 min [M+H]+ 563.5 Method High pH_v003.

Step 3: 2-(5-(2-(Benzyloxy)-1,1,1-trifluoropropan-2-yl)-1,3,4-oxadiazol-2-yl)-6-methoxy-5-(trifluoromethyl)pyridin-3-amine To a stirring solution of the tert-butyl 2-(5-(2-(benzyloxy)-1,1,1-trifluoropropan-2-yl)-1,3,4-oxadiazol-2-yl)-6-methoxy-5-(trifluoromethyl)pyridin-3-ylcarbamate (707 mg, 1.257 mmol) in DCM (10 ml) was added TFA (3 ml) and stirring continued for 45 min. The resulting mixture was washed with 2M NaOH and the organic phase separated using a phase separator. The solvent was removed in vacuo to afford the title product as a TFA salt; LC-MS Rt=1.42 min [M+H]+ 463.2 Method High pH_v003.

Step 4: 2-(5-(3-Amino-6-methoxy-5-(trifluoromethyl)pyridin-2-yl)-1,3,4-oxadiazol-2-yl)-1,1,1-trifluoropropan-2-ol To a stirring solution of 2-(5-(2-(benzyloxy)-1,1,1-trifluoropropan-2-yl)-1,3,4-oxadiazol-2-yl)-6-methoxy-5-(trifluoromethyl)pyridin-3-amine trifluoroacetate (Step 3) (450 mg, 0.973 mmol) in EtOH (25 ml) was added palladium hydroxide on carbon (45.1 mg, 0.321 mmol) followed by ammonium formate (614 mg, 9.73 mmol). The mixture was heated at reflux for 1 h and then filtered through Celite® washing through with EtOH followed by water. The ethanol was removed in vacuo and the resultant aqueous phase was extracted with EtOAc. The combined organic extracts were washed with water, brine, dried (MgSO4) and concentrated in vacuo to afford the title product; 1H NMR (400 MHz, DMSO-d6) δ 7.85 (1H, s), 7.74 (1H, s), 6.74 (2H, s), 3.94 (3H, s), 1.86 (3H, s). LC-MS Rt=1.17 min [M+H]+ 373.1 Method: 2minLC_v003.

Examples 2 and 3

Chiral separation of 2-(5-(3-amino-6-methoxy-5-(trifluoromethyl)pyridin-2-yl)-1,3,4-oxadiazol-2-yl)-1,1,1-trifluoropropan-2-ol (Example 1) using supercritical fluid chromatography afforded enantiomers 1 and 2:

Conditions:

Mobile Phase: 10% MeOH+0.1% DEA/90% CO2

Column: Chiralpak AD-H, 250×10 mm id, 5 μm

Detection: UV @ 220 nm

Flow rate: 10 ml/min

Sample concentration: 63 mg/ml (250 mg+4 ml EtOH).

Example 2

First Eluted Peak. Entantiomer 1: (R)-2-(5-(3-amino-6-methoxy-5-(trifluoromethyl)pyridin-2-yl)-1,3,4-oxadiazol-2-yl)-1,1,1-trifluoropropan-2-ol

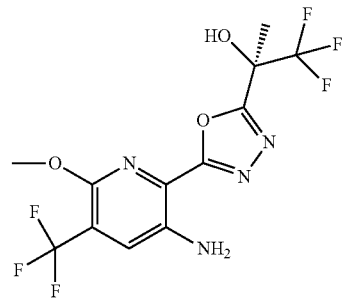 [SMILES: COc1nc(-c2nnc([C@@](C)(O)C(F)(F)F)o2)c(N)cc1C(F)(F)F]

1H NMR (400 MHz, DMSO-d6) δ 7.86 (1H, s), 7.75 (1H, s), 6.74 (2H, s), 3.94 (3H, s), 1.86 (3H, s). LC-MS Rt=4.04 min [M+H]+ 373.4 (Method 10 min_v003). The stereochemistry of this compound was confirmed by 3D X-ray crystallographic data.

Example 3

Second Eluted Peak. Enantiomer: (S)-2-(5-(3-amino-6-methoxy-5-(trifluoromethyl)pyridin-2-yl)-1,3,4-oxadiazol-2-yl)-1,1,1-trifluoropropan-2-ol

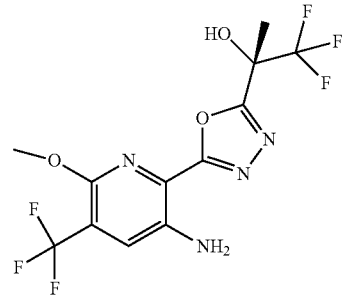 [SMILES: COc1nc(-c2nnc([C@](C)(O)C(F)(F)F)o2)c(N)cc1C(F)(F)F]

1H NMR (400 MHz, DMSO-d6) δ 7.86 (1H, s), 7.75 (1H, s), 6.74 (2H, s), 3.94 (3H, s), 1.86 (3H, s). LC-MS Rt=4.04 min [M+H]+ 373.4 Method 10 min_v003.

Example 4

3-(5-Benzyl-1,3,4-oxadiazol-2-yl)-5-bromo-6-(trifluoromethyl)pyrazin-2-amine

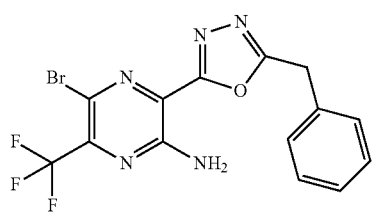 [SMILES: Nc1nc(C(F)(F)F)c(Br)nc1-c1nnc(Cc2ccccc2)o1]

Step 1: 3-Amino-6-bromo-5-(trifluoromethyl)pyrazine-2-carbohydrazide

To a solution of 3-Amino-6-bromo-5-trifluoromethyl-pyrazine-2-carboxylic acid ethyl ester (Int. F1) (1.00 g, 3.18 mmol) in dry EtOH (25 ml) was added hydrazine monohydrate (309 ul, 6.37 mmol) and the mixture was stirred at reflux (ca. 90° C.). After 3 hr 45 min the reaction mixture was cooled in an ice bath and added to water. The resulting yellow ppt was filtered under vacuum and dried in a vacuum oven overnight to give the title compound as a yellow solid $^1$H NMR (400 MHz, DMSO-d6) δ10.10 (1H, s), 8.00 (2H, s), 4.65 (2H, s).

Step 2: 3-Amino-6-bromo-N'-(2-phenylacetyl)-5-(trifluoromethyl)pyrazine-2-carbohydrazide To a stirred solution of phenyl acetic acid (95.0 mg, 0.698 mmol) in NMP (6 ml) was added a solution 3-amino-6-bromo-5-(trifluoromethyl)pyrazine-2-carbohydrazide (step 1) (250 mg, 0.837 mmol) in NMP (6 ml) followed by DIPEA (609 ul, 3.49 mmol). The resulting mixture was treated with HATU (398 mg, 1.047 mmol) portionwise and stirred at RT for 90 min. The mixture was added to EtOAc (50 ml) and washed with 0.1M NaOH (50 ml). The aqueous layer was back extracted with EtOAc (50 ml). The combined organic portions were washed with water (50 ml), brine (50 ml), dried over magnesium sulfate and concentrated in vacuo. The crude product was purified by chromatography on silica eluting with 1:1 EtOAc/iso-hexane to afford the title compound as a yellow solid. 1H NMR (400 MHz, DMSO-d6) δ 10.65 (1H, s), 10.29 (1H, s), 8.02 (2H, s), 7.30 (5H, m), 3.52 (2H, s). 19F NMR (400 MHz, DMSO-d6) δ-66 (s, CF3).

Step 3: 3-(5-Benzyl-1,3,4-oxadiazol-2-yl)-5-bromo-6-(trifluoromethyl)pyrazin-2-amine To a solution of 3-amino-6-bromo-N'-(2-phenylacetyl)-5-(trifluoromethyl)pyrazine-2-carbohydrazide (step 1) (92 mg, 0.220 mmol) in THF (2 ml) was added a solution of TsCl (50 mg, 1.200 mmol) in THF (0.5 ml). The resulting solution was then added to PS-BEMP (384 mg, 1.100 mmol) and the mixture was heated using microwave radiation at 120° C. for 10 min. The reaction mixture was loaded onto an Isolute® PE-AX/SCX-2 cartridge (10 g, Solid Phase Extraction) pre-wetted with THF. The cartridge was eluted with THF (40 ml) and the organic portion was concentrated in vacuo. The crude product was purified by chromatography on silica eluting with 20% EtOAc/iso-hexane followed by further purification by preparative HPLC to afford the title compound; $^1$H NMR (400 MHz, DMSO-d6) δ 7.35 (5H), 4.49 (2H, s). LC-MS Rt=5.76 min [M+H]+ 400.1 Method 10minLC_v002.

Example 5

(5-(3-Amino-6-bromo-5-(trifluoromethyl)pyrazin-2-yl)-1,3,4-oxadiazol-2-yl)(phenyl)methanone

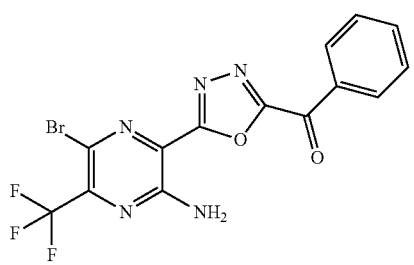 [SMILES: Nc1nc(C(F)(F)F)c(Br)nc1-c1nnc(C(=O)c2ccccc2)o1]

The title compound was prepared analogously to Example 4 by replacing phenyl acetic acid (step 2) with phenylglyoxylic acid; 1H NMR (400 MHz, DMSO-d6) δ 8.41 (2H, d), 7.82 (1H, t), 7.70 (2H, t). LC-MS Rt=5.82 min [M+H]+416.1 Method 10minLC_v002.

Example 6

2-(5-(3-Amino-5,6-bis(trifluoromethyl)pyrazin-2-yl)-1,3,4-oxadiazol-2-yl)-1,1,1-trifluoropropan-2-ol

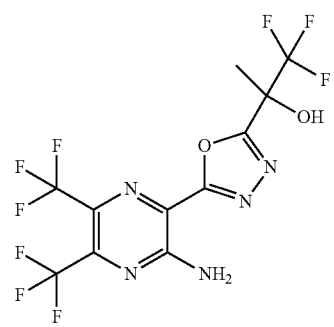 [SMILES: CC(O)(c1nnc(-c2nc(C(F)(F)F)c(C(F)(F)F)nc2N)o1)C(F)(F)F]

Step 1: 3-Amino-N'-(2-(benzyloxy)-3,3,3-trifluoro-2-methylpropanoyl)-5,6-bis(trifluoromethyl)pyrazine-2-carbohydrazide A stirred solution of 3-amino-5,6-bis(trifluoromethyl)pyrazine-2-carbohydrazide (Int. G) (431 mg, 1.491 mmol) in dry NMP (3 ml) was treated with 2-(benzyloxy)-3,3,3-trifluoro-2-methylpropanoic acid (Int. D) (370 mg, 1.491 mmol) and stirred at RT for 5 minutes. The resulting yellow solution was cooled to 0° C. and treated with HATU (567 mg, 1.491 mmol) followed by dropwise addition of triethylamine (0.208 ml, 1.491 mmol). The orange/red suspension was stirred at 0° C. for 15 minutes and then allowed to warm to RT stirring for approx. 2 hours. The mixture was partitioned between EtOAc (50 ml) and 1M NaOH (50 ml), shaken and separated. The organic portion was washed with brine (25 ml), dried (MgSO$_4$) and concentrated in vacuo to give an orange oil. The crude product was purified by mass directed LC-MS eluting with MeCN/Water/0.1% TFA. The clean fractions were poured into EtOAc (50 ml) and washed with saturated NaHCO$_3$ (50 ml), dried (MgSO$_4$) and concentrated in vacuo to afford the title compound as a pale yellow crystalline solid.

1H NMR (400 MHz, DMSO-d6) δ 10.82 (1H, br s), 10.4 (1H, br s), 8.72 (1H, broad hump), 8.4 (1H, broad hump), 7.5 (2H, d), 7.3-7.42 (3H, m), 4.79 (2H, m), 1.7 (3H, s). (Trace of EtOAc present, but clean and correlates to proposed structure).

19F NMR (400 MHz, DMSO-d6): Peak 1 at −61 ppm, peak 2 at −64.5 ppm, peak 3 at −76 ppm

Step 2: 3-(5-(2-(Benzyloxy)-1,1,1-trifluoropropan-2-yl)-1,3,4-oxadiazol-2-yl)-5,6-bis(trifluoromethyl)pyrazin-2-amine A stirred solution of 3-amino-W-(2-(benzyloxy)-3,3,3-trifluoro-2-methylpropanoyl)-5,6-bis(trifluoromethyl)pyrazine-2-carbohydrazide (step 1) (510 mg, 0.982 mmol) in DCM (20 ml) was treated with triethylamine (0.411 ml, 2.95 mmol) and stirred at RT. Tosyl chloride (562 mg, 2.95 mmol) was added and stirring continued for 30 minutes. The reaction mixture was partitioned between EtOAc (50 ml) and 1M HCl (50 ml), shaken and separated. The organic portion was washed with brine (30 ml), dried ($MgSO_4$) and concentrated in vacuo to give a yellow oil. The crude product was purified by mass directed LC-MS eluting with MeCN/Water/0.1% TFA. The clean fractions were poured into EtOAc (50 ml) and washed with saturated $NaHCO_3$ (50 ml), dried ($MgSO_4$) and concentrated in vacuo to afford the title compound as a white crystalline solid.

1H NMR (400 MHz, DMSO-d6) δ 9.28 (1H, broad hump), 8.1 (1H, broad hump), 7.46 (2H, m), 7.3-7.4 (3H, m), 4.72 (1H, d), 4.52 (1H, d), 2.1 (3H, s). LC-MS Rt=1.40 min [M+H]+ 502.2 Method 2minLC_v003.

Step 3: 2-(5-(3-Amino-5,6-bis(trifluoromethyl)pyrazin-2-yl)-1,3,4-oxadiazol-2-yl)-1,1,1-trifluoropropan-2-ol A solution of 3-(5-(2-(benzyloxy)-1,1,1-trifluoropropan-2-yl)-1,3,4-oxadiazol-2-yl)-5,6-bis(trifluoromethyl)pyrazin-2-amine (Step 2) (50 mg, 0.100 mmol) in EtOH (3 ml) under $N_2$ was charged with Pd/C (1.061 mg, 9.97 µmol) and placed under a positive pressure of H2 (0.35 bar) at RT overnight. The reaction mixture was filtered through Celite® (Filter Material) and washed through with ethanol (30 ml), followed by DCM (10 ml). The filtrate was concentrated in vacuo and the resulting crude product was purified by UV directed LC-MS eluting with MeCN/Water/0.1% TFA. The clean fractions were poured into EtOAc (50 ml) and washed with saturated $NaHCO_3$ (50 ml), dried ($MgSO_4$) and concentrated in vacuo to afford the title compound to give a pale orange solid. 1H NMR (400 MHz, DMSO-d6) δ 9.22 (1H, broad hump), 8.1 (1H, broad hump), 7.92 (1H, s), 1.4 (3H, s). 19F NMR (400 MHz, DMSO-d6) Peak 1 at −61 ppm, peak 2 at −64 ppm, peak 3 at −79.4 ppm.

Examples 7 and 8

These compounds namely, (R)-2-(5-(3-Amino-5,6-bis(trifluoromethyl)pyrazin-2-yl)-1,3,4-oxadiazol-2-yl)-1,1,1-trifluoropropan-2-ol and (S)-2-(5-(3-Amino-5,6-bis(trifluoromethyl)pyrazin-2-yl)-1,3,4-oxadiazol-2-yl)-1,1,1-trifluoropropan-2-ol were prepared by chiral separation of 2-(5-(3-amino-5,6-bis(trifluoromethyl)pyrazin-2-yl)-1,3,4-oxadiazol-2-yl)-1,1,1-trifluoropropan-2-ol (Example 6) using under the following HPLC conditions:

Column: Chiralcel OJ-H, 20×250 mm id, 10 µm
Mobile Phase: 4% EtOH/96% heptane+0.1 DEA
Flow Rate: 20 ml/min
Detection: UV @ 320 nm
Sample Injection 250 mg in EtOH (3 ml)
Injection Volume: 125 µl Examples 7 and 8 are enantiomers. Compounds identified by column separation.

Example 7

First Eluted Peak. Enantiomer 1 of 2-(5-(3-Amino-5,6-bis(trifluoromethyl)pyrazin-2-yl)-1,3,4-oxadiazol-2-yl)-1,1,1-trifluoropropan-2-ol

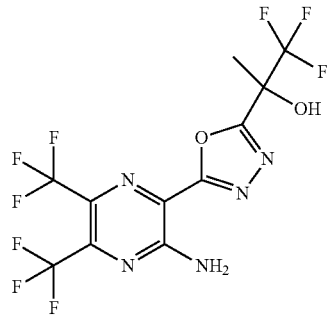 [SMILES: CC(O)(c1nnc(-c2nc(C(F)(F)F)c(C(F)(F)F)nc2N)o1)C(F)(F)F]

1H NMR (400 MHz, DMSO-d6) δ 9.18-9.3 (1H, br s), 8.02-8.18 (1H, br s), 7.92 (1H, s), 1.89 (3H, s). 19F NMR (400 MHz, DMSO-d6) Peak 1 at −61.6 ppm, peak 2 at −64.4 ppm, peak 3 at −79.4 ppm

Example 8

Second Eluted Peak: Enantiomer 2 of 2-(5-(3-Amino-5,6-bis(trifluoromethyl)pyrazin-2-yl)-1,3,4-oxadiazol-2-yl)-1,1,1-trifluoropropan-2-ol

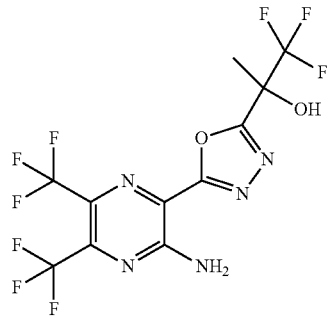 [SMILES: CC(O)(c1nnc(-c2nc(C(F)(F)F)c(C(F)(F)F)nc2N)o1)C(F)(F)F]

1H NMR (400 MHz, DMSO-d6): δ 9.18-9.3 (1H, br s), 8.02-8.16 (1H, br s), 7.92 (1H, s), 1.88 (3H, s). 19F NMR (400 MHz, DMSO-d6) Peak 1 at −61.6 ppm, peak 2 at −64.4 ppm, peak 3 at −79.4 ppm.

Example 9

2-(5-Benzyl-1,3,4-oxadiazol-2-yl)-6-bromo-5-(trifluoromethyl)pyridin-3-amine

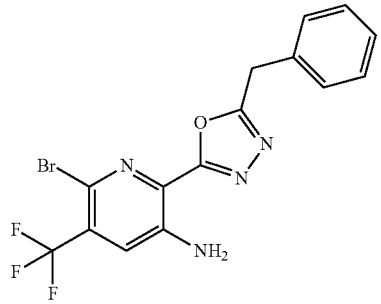 [SMILES: Nc1cc(C(F)(F)F)c(Br)nc1-c1nnc(Cc2ccccc2)o1]

Step 1: 3-Amino-6-bromo-N'-(2-phenylacetyl)-5-(trifluoromethyl)picolinohydrazide To a stirred solution of 3-amino-6-bromo-5-(trifluoromethyl)picolinohydrazide (Int. H) (150 mg, 0.502 mmol) in NMP (4 ml) was added phenylacetic acid (57 mg, 0.419 mmol) followed by DIPEA (366 ul, 2.093 mmol). To this solution was added HATU (239 mg, 0.628 mmol) portionwise and the reaction mixture was left to stir at RT for 1 h. The reaction mixture was added to EtOAc (25 ml) and the organic portion was separated and washed with 0.1M HCl (2×15 ml), water (25 ml), 0.1M NaOH (2×15 ml), water (25 ml), brine (25 ml) dried (Mg SO4) and concentrated in vacuo. The crude product was purified by chromatography on silica eluting with 1:1 EtOAc/iso-hexane to afford the title compound as a yellow solid; 1H NMR (400 MHz, DMSO-d6) δ 10.30 (1H, s), 10.20 (1H, s), 7.70 (1H, s), 7.38 (4H, m), 7.25 (3H, m), 3.55 (2H, s). LC-MS Rt=1.43 min [M+H]+ 417.1 Method 2minLC_v002.

Step 2: 2-(5-Benzyl-1,3,4-oxadiazol-2-yl)-6-bromo-5-(trifluoromethyl)pyridin-3-amine To a stirred suspension of 3-amino-6-bromo-N'-(2-phenylacetyl)-5-(trifluoromethyl) picolinohydrazide (106 mg, 0.254 mmol) in CHCl$_3$ (2 ml) was added TEA (142 ul, 1.016 mmol) followed by TsCl (145 mg, 0.762 mmol). The mixture was heated to 65° C. for 3 h. The solvent was removed in vacuo and the resulting brown residue was suspended in EtOAc (10 ml). The mixture was washed with brine (10 ml), dried (MgSO4) and concentrated in vacuo. The crude product was purified by chromatography on silica eluting with 85% iso-hexane/EtOAc to afford the title compound as a yellow solid; 1H NMR (400 MHz, DMSO-d6) δ 7.85 (1H, s), 7.39 (4H, m), 7.30 (3H, m), 4.45 (2H, s). LC-MS Rt=5.84 min [M+H]+ 401.0 Method 10minLC_v002.

The compounds of the following tabulated Examples (Table 2) were prepared by a similar method to that of Example 9 from either 3-amino-6-bromo-5-(trifluoromethyl)picolinohydrazide (Int. H) or 3-amino-5-(trifluoromethyl)picolinohydrazide (Int. I) and the appropriate acid.

TABLE 2

| Ex. | Structure | Name | NMR/[M + H]+ |
|---|---|---|---|
| 9.1 | 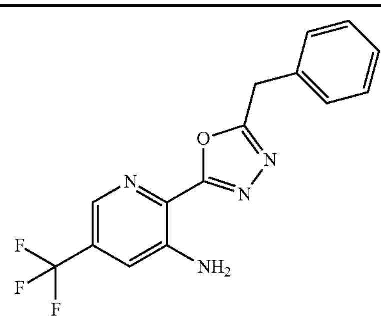 | 2-(5-Benzyl-[1,3,4]oxadiazol-2-yl)-5-trifluoromethyl-pyridin-3-ylamine | Rt 1.5 mins; [M + H]+ 321.1 Method 2 minLC_v002 1H NMR (400 MHz, DMSO-d6) δ 8.22 (1H, s), 7.69 (1H, s), 7.39 (4H, m), 7.30 (1H, m), 7.18 (2H, s), 4.42 (1H, s) |
| 9.2 | 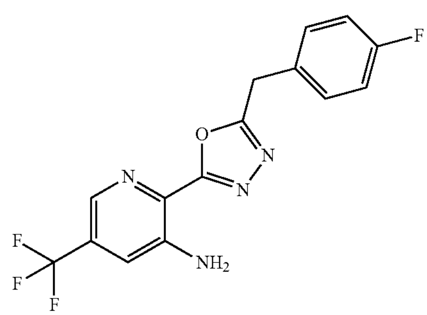 [SMILES: Nc1cc(C(F)(F)F)cnc1-c1nnc(Cc2ccc(F)cc2)o1] | 2-[5-(4-Fluoro-benzyl)-[1,3,4]oxadiazol-2-yl]-5-trifluoromethyl-pyridin-3-ylamine | Rt 5.17 min; [M + H]+ 339.1 Method 10 minLC_v002.. 1H NMR (400 MHz, DMSO-d6) δ 8.25 (1H, d), 7.70 (1H, d), 7.45 (2H, m), 7.20 (4H, m), 7.42 (2H, s). |
| 9.3 | 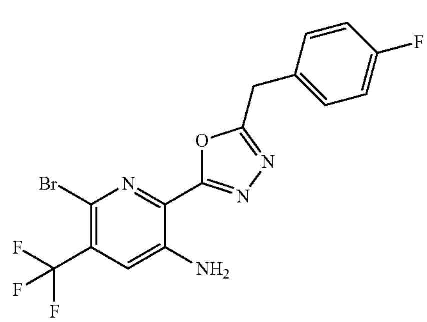 [SMILES: Nc1cc(C(F)(F)F)c(Br)nc1-c1nnc(Cc2ccc(F)cc2)o1] | 6-Bromo-2-[5-(4-fluoro-benzyl)-[1,3,4]oxadiazol-2-yl]-5-trifluoromethyl-pyridin-3-ylamine | Rt 5.86 min; [M + H]+ 417.1 Method 10 minLC_v002.. 1H NMR (400 MHz, DMSO-d6) δ 7.85 (1H, s), 7.45 (2H, m), 7.30 (2H, s), 7.21 (2H, t), 4.45 (2H, s). |

| Ex. | Structure | Name | NMR/[M + H]+ |
|---|---|---|---|
| 9.4 | 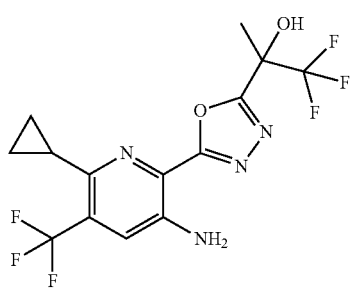 | 6-Bromo-2-[5-(2,2,2-trifluoro-ethyl)-[1,3,4]oxadiazol-2-yl]-5-trifluoromethyl-pyridin-3-ylamine | Rt 1.49 min; [M + H]+ 391.1 Method 2 minLC_v002.. 1H NMR (400 MHz, DMSO-d6) δ 7.90 (1H, s), 7.31 (2H, s), 4.51 (2H, q). |

Example 10

2-(5-(3-Amino-6-cyclopropyl-5-(trifluoromethyl)pyridin-2-yl)-1,3,4-oxadiazol-2-yl)-1,1,1-trifluoropropan-2-ol

Step 1: 3-Amino-6-bromo-N'-(3,3,3-trifluoro-2-hydroxy-2-methylpropanoyl)-5-(trifluoromethyl)picolinohydrazide A cooled (0° C.) solution of 3-amino-6-bromo-5-(trifluoromethyl)picolinohydrazide (Intermediate H) (15 g, 50.2 mmol) in dry NMP (50 ml) was treated with 3,3,3-trifluoro-2-hydroxy-2-methylpropanoic acid (8.72 g, 55.2 mmol), HATU (20.98 g, 55.2 mmol) followed by dropwise addition of TEA (15.38 ml, 110 mmol) over 10 minutes. The orange solution was stirred at 0° C. and allowed to warm to RT and stirred for 3 days. The reaction mixture was partitioned between EtOAc (200 mL) and 1M NaOH (200 mL), shaken and separated. The organic portion washed with brine (100 mL), dried (MgSO$_4$) and concentrated in vacuo to give an orange oil. The oil was taken up in methanol (50 mL) and triturated with water (300 mL) to afford the title compound as a yellow solid;

1H NMR (400 MHz, DMSO-d6) δ 10.3 (1H, br s), 10.08 (1H, br s), 7.72 (1H, s), 7.24 (2H, br s), 7.16 (1H, br s), 1.54 (3H, s). LC-MS Rt=1.04 min [M+H]+ 439.0/441.1 Method 2minLC_v003. 19F NMR (400 MHz, DMSO-d6) Peak 1 at −62.6 ppm, peak 2 at −78 ppm.

Step 2: 3-Amino-6-bromo-N'-(3,3,3-trifluoro-2-methyl-2-(triisopropylsilyloxy)propanoyl)-5-(trifluoromethyl)picolinohydrazide To a suspension of 3-amino-6-bromo-W-(3,3,3-trifluoro-2-hydroxy-2-methylpropanoyl)-5-(trifluoromethyl)picolinohydrazide (step 1) (4 g, 9.11 mmol) in DCM (60 ml), triethylamine (1.270 ml, 9.11 mmol) was added to give a yellow solution. The solution was cooled to 0° C. (ice bath) and treated with triisopropylsilyl trifluoromethanesulfonate (4.94 ml, 18.22 mmol). The reaction mixture was stirred at 0° C. for 1 hour and allowed to warm to RT and stirred for 3 days. The reaction mixture was partitioned between DCM (100 ml) and water (100 ml), phases shaken and separated. The organic portion was washed with brine (100 ml), dried (MgSO4) and concentrated in vacuo. The resulting oil was purified by chromatography on silica eluting with 0-30% DCM in iso-hexane to afford the title compound; LC-MS Rt=1.58 min [M+H]+ 595/597 Method 2minLC_v003.

Step 3: 6-Bromo-2-(5-(1,1,1-trifluoro-2-(triisopropylsilyloxy)propan-2-yl)-1,3,4-oxadiazol-2-yl)-5-(trifluoromethyl)pyridin-3-amine To a cooled (0° C.) solution of 3-amino-6-bromo-N'-(3,3,3-trifluoro-2-methyl-2-(triisopropylsilyloxy) propanoyl)-5-(trifluoromethyl)picolinohydrazide (5.42 g, 9.10 mmol) in DCM (50 ml) was added TEA (3.81 ml, 27.3 mmol). The resulting solution was stirred at 0° C. for 5 minutes and treated with Tosyl chloride (5.21 g, 27.3 mmol). The mixture was allowed to warm to RT and stirred for 48 h. The reaction mixture was partitioned between DCM (100 ml) and water (100 ml), phases shaken and separated. The organic portion was washed with 1M NaOH (100 ml), 1M HCl (100 ml), water (100 ml), brine (100 ml), dried (MgSO4) (~10 g) and concentrated in vacuo to give an orange oil. Purification of the oil by chromatography on silica eluting with 0-15% EtOAc in iso-hexane afforded the title compound; LC-MS Rt=7.41 min [M+H]+ 577/579 Method 10minLC_v003.

Step 4: 6-Cyclopropyl-2-(5-(1,1,1-trifluoro-2-(triisopropylsilyloxy)propan-2-yl)-1,3,4-oxadiazol-2-yl)-5-(trifluoromethyl)pyridin-3-amine To a stirring solution of 6-bromo-2-(5-(1,1,1-trifluoro-2-(triisopropylsilyloxy)propan-2-yl)-1,3,4-oxadiazol-2-yl)-5-(trifluoromethyl)pyridin-3-amine (step 3) (200 mg, 0.346 mmol) in dry 1,4-dioxane (10 ml) under N$_2$ at RT was added K$_2$CO$_3$ (144 mg, 1.039 mmol) followed by cyclopropylboronic acid (89 mg, 1.039 mmol) and palladiumtetrakis (40.0 mg, 0.035 mmol). The resulting suspension was stirred and heated at reflux (120° C.) overnight for 4 days. The mixture was filtered through Celite® (filter material) and washed through with water (30 ml) and EtOAc (50 ml). The filtrate was separated and the organic portion was dried (MgSO$_4$) and concentrated in vacuo to afford the title compound which was used in the next step without further purification; LC-MS Rt=7.75 min [M+H]+ 539.6 Method 10minLC_v003.

Step 5: 2-(5-(3-Amino-6-cyclopropyl-5-(trifluoromethyl)pyridin-2-yl)-1,3,4-oxadiazol-2-yl)-1,1,1-trifluoropropan-2-ol A solution of 6-cyclopropyl-2-(5-(1,1,1-trifluoro-2-(triisopropylsilyloxy)propan-2-yl)-1,3,4-oxadiazol-2-yl)-5-(trifluoromethyl)pyridin-3-amine (step 4) (200 mg, 0.371 mmol) in dry THF (10 ml) was treated with silica supported tetra-n-butylammonium fluoride (500 mg, 0.750 mmol). The resulting red suspension was stirred at RT for 5 minutes and filtered through Celite® (filter material). The mixture was washed through with THF (10 ml) and the filtrate was concentrated in vacuo to give an orange oil. Purification of the oil by chromatography on silica eluting with 0-40% EtOAc in iso-hexane afforded the title compound;

1H NMR (400 MHz, DMSO-d6) δ 7.74 (1H, s), 7.73 (1H, s), 6.92 (2H, s), 2.16 (1H, m), 1.86 (3H, s), 1.01 (2H, m), 0.98 (2H, m). 19F NMR (400 MHz, DMSO-d6) Peak 1 at −60.2 ppm, peak 2 at −79.6 ppm. LC-MS Rt=1.23 min [M+H]+ 383.2 Method 2minLC_v003.

Example 10.1

2-(5-(3-amino-6-methyl-5-(trifluoromethyl)pyridin-2-yl)-1,3,4-oxadiazol-2-yl)-1,1,1-trifluoropropan-2-ol The title compound was prepared analogously to Example 10 by replacing cyclopropylboronic acid (step 4) with 2,4,6-trimethyl-1,3,5,2,4,6-trioxatriborinane; 1H NMR of crude racemic material (400 MHz, DMSO-d6) δ 7.79 (1H, s), 7.75 (1H, s), 7.0 (2H, s), 2.53 (3H, s), 1.89 (3H, s). LC-MS Rt=3.75 min [M+H]+ 357.2 Method 10minLC_v003. 19F NMR of crude racemic material (400 MHz, DMSO-d6) Peak 1 at −61.9 ppm, peak 2 at −79.6 ppm.

Example 10.2

2-(5-(3-amino-6-bromo-5-(trifluoromethyl)pyridin-2-yl)-1,3,4-oxadiazol-2-yl)-1,1,1-trifluoropropan-2-ol The title compound was prepared analogously to Example 10 by replacing 6-cyclopropyl-2-(5-(1,1,1-trifluoro-2-(triisopropylsilyloxy)propan-2-yl)-1,3,4-oxadiazol-2-yl)-5-(trifluoromethyl)pyridin-3-amine (step 5) with 6-bromo-2-(5-(1,1,1-trifluoro-2-(triisopropylsilyloxy)propan-2-yl)-1,3,4-oxadiazol-2-yl)-5-(trifluoromethyl)pyridin-3-amine (step 3); 1H NMR (400 MHz, DMSO-d6) δ 7.90 (1H, s), 7.84 (1H, s), 7.34 (2H, s), 1.86 (3H, s). LC-MS Rt=4.42 min [M+H]+ 423 Method 10minLC_v003.

Example 10.3

2-(5-(3-Amino-5-(trifluoromethyl)pyridin-2-yl)-1,3,4-oxadiazol-2-yl)-1,1,1-trifluoropropan-2-ol

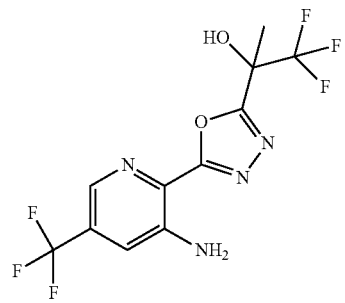 [SMILES: CC(O)(c1nnc(-c2ncc(C(F)(F)F)cc2N)o1)C(F)(F)F]

Step 1: 2-(5-(1,1,1-Trifluoro-2-(triisopropylsilyloxy)propan-2-yl)-1,3,4-oxadiazol-2-yl)-5-(trifluoromethyl)pyridin-3-amine The title compound was prepared analogously to 6-bromo-2-(5-(1,1,1-trifluoro-2-(triisopropylsilyloxy)propan-2-yl)-1,3,4-oxadiazol-2-yl)-5-(trifluoromethyl)pyridin-3-amine (Example 10, step 3) by replacing 3-amino-6-bromo-5-(trifluoromethyl)picolinohydrazide (Intermediate H) (step 1) with 3-amino-5-(trifluoromethyl)picolinohydrazide (Int. I); LCMS: Rt=1.66 min; [M+H]+ 499.3 Method 2minLC_v003.

Step 2: 2-(5-(3-Amino-5-(trifluoromethyl)pyridin-2-yl)-1,3,4-oxadiazol-2-yl)-1,1,1-trifluoropropan-2-ol The title compound was prepared from 2-(5-(1,1,1-trifluoro-2-(triisopropylsilyloxy)propan-2-yl)-1,3,4-oxadiazol-2-yl)-5-(trifluoromethyl)pyridin-3-amine (step 1) analogously to 2-(5-(3-amino-6-cyclopropyl-5-(trifluoromethyl)pyridin-2-yl)-1,3,4-oxadiazol-2-yl)-1,1,1-trifluoropropan-2-ol (Ex. 10 step 5); 1H NMR (400 MHz, DMSO-d6) δ 8.31 (1H, s), 7.78 (1H, s), 7.73 (1H, s), 7.21 (2H, s), 1.86 (3H, s). LCMS: Rt=1.07 min; [M+H]+ 343.1 Method 2minLC_v003.

Examples 10.4 and 10.5

The following compounds were prepared by chiral separation of 2-(5-(3-amino-5-(trifluoromethyl)pyridin-2-yl)-1,3,4-oxadiazol-2-yl)-1,1,1-trifluoropropan-2-ol (Example 10.3) using Supercritical Fluid Chromatography under the following conditions:

Mobile Phase: 10% isopropanol+0.1% DEA/90% $CO_2$

Column: Chiralpak AS-H, 250×10 mm, 5 μm

Detection: UV @ 220 nm

Flow rate: 10 ml/min

Sample concentration: 118 mg in 1.25 ml EtOH.

Example 10.4

First Eluted Peak. Enantiomer 1 of 2-(5-(3-amino-5-(trifluoromethyl)pyridin-2-yl)-1,3,4-oxadiazol-2-yl)-1,1,1-trifluoropropan-2-ol

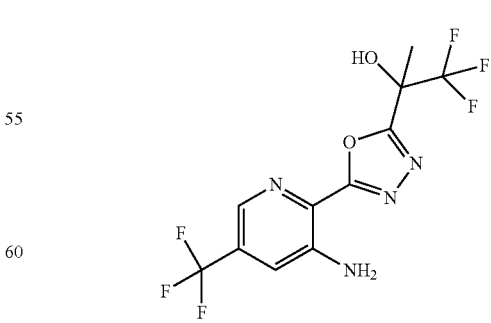

1H NMR (400 MHz, DMSO-d6) δ 8.31 (1H, s), 7.78 (1H, s), 7.73 (1H, s), 7.21 (2H, s), 1.86 (3H, s). LC-MS Rt=3.36 min [M+H]+ 343.4 Method 10minLC_v003.

Example 10.5

Second Eluted Peak. Enantiomer 2 of 2-(5-(3-amino-5-(trifluoromethyl)pyridin-2-yl)-1,3,4-oxadiazol-2-yl)-1,1,1-trifluoropropan-2-ol

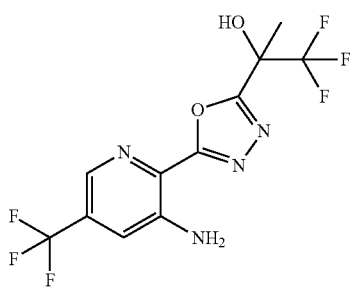 [SMILES: CC(O)(c1nnc(-c2ncc(C(F)(F)F)cc2N)o1)C(F)(F)F]

1H NMR (400 MHz, DMSO-d6) δ 8.31 (1H, s), 7.78 (1H, s), 7.73 (1H, s), 7.21 (2H, s), 1.86 (3H, s). LC-MS Rt=3.35 min [M+H]+ 343.4 Method 10minLC_v003.

Example 10.6

2-(5-(3-Amino-6-bromo-5-(trifluoromethyl)pyridin-2-yl)-1,3,4-oxadiazol-2-yl)propan-2-ol The title compound was prepared from 3-amino-6-bromo-5-(trifluoromethyl)picolinohydrazide (Intermediate H) and 2-hydroxy-2-methylpropanoic acid analogously to Example 10 (leave out step 4);

1H NMR (400 MHz, DMSO-d6) δ 7.9 (1H, s), 7.3 (2H, s), 6.0 (1H, s), 1.6 (6H, s). LC-MS Rt=1.07 min [M+H]+ 367.1 Method 2minLC_v003.

Example 11

(R)-2-(5-(amino(phenyl)methyl)-1,3,4-oxadiazol-2-yl)-6-bromo-5-(trifluoro methyl)pyridin-3-amine

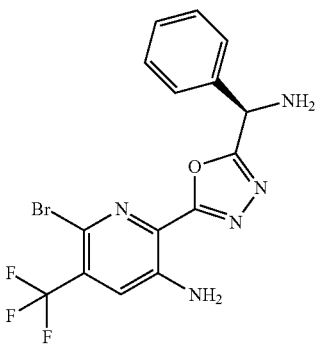 [SMILES: Nc1cc(C(F)(F)F)c(Br)nc1-c1nnc([C@H](N)c2ccccc2)o1]

Step 1: (R)-Benzyl 2-(2-(3-amino-6-bromo-5-(trifluoromethyl)picolinoyl)hydrazinyl)-2-oxo-1-phenylethylcarbamate A suspension of 3-amino-6-bromo-5-trifluoromethyl-pyridine-2-carboxylic acid (Int. A) (200 mg, 0.702 mmol) in NMP (6 ml) was treated with (R)-benzyl 2-hydrazinyl-2-oxo-1-phenylethylcarbamate (Int. JR) (231 mg, 0.772 mg) followed by portionwise addition of HATU (293 mg, 0.772 mmol). After stirring at RT for 45 minutes, the reaction mixture was added to EtOAc (50 ml) and washed with 0.1 M NaOH (50 ml). The aqueous layer was back extracted with EtOAc (25 ml). The combined organic portions were washed with water (75 ml), brine (50 ml), dried (MgSO4) and concentrated in vacuo. The crude product was loaded in MeOH onto a pre-wetted (MeOH) Isolute® PE-AX (anion exchange) cartridge. The cartridge was eluted with MeOH (70 ml) and the filtrate was concentrated in vacuo to give a yellow solid which was placed under high vacuum to give the title compound as a yellow solid;

1H NMR (400 MHz, DMSO-d6) δ 10.50 (2H, broad), 8.04 (1H, d), 7.70 (1H, s), 7.52 (2H, d), 7.35 (8H), 7.21 (2H, s), 5.45 (1H, d), 5.06 (2H). Some NMP and acetic acid present. LC-MS Rt=1.55 min [M+H]+ 568.1 Method 2minLC_v002.

Step 2: (R)-Benzyl(5-(3-amino-6-bromo-5-(trifluoromethyl)pyridin-2-yl)-1,3,4-oxadiazol-2-yl)(phenyl)methylcarbamate To a solution of (R)-benzyl 2-(2-(3-amino-6-bromo-5-(trifluoromethyl)picolinoyl) hydrazinyl)-2-oxo-1-phenylethylcarbamate (step 1) (360 mg, 0.636 mmol) in CHCl3 (6 ml) was added triethylamine (354 ul, 2.54 mmol) followed by tosyl chloride (242 mg, 1.271 mmol). The resulting mixture was stirred at 65° C. for 2 h and then concentrated in vacuo. The residue was dissolved in EtOAc (20 ml) and washed with brine (20 ml), dried (MgSO4) and evaporated under reduced. The crude product was purified by chromatography on silica eluting with 75% iso-hexane/EtOAc to afford the title compound; 1H NMR (400 MHz, DMSO-d6) δ 8.85 (1H, d), 7.85 (1H, s), 7.50 (2H, d), 7.45-7.30 (10H), 6.32 (1H, d), 5.10 (2H, s). LC-MS Rt=1.64 min [M+H]+ 550 Method 2minLC_v002.

Step 3: (R)-2-(5-(amino(phenyl)methyl)-1,3,4-oxadiazol-2-yl)-6-bromo-5-(trifluoro methyl)pyridin-3-amine To a stirred solution of (R)-benzyl(5-(3-amino-6-bromo-5-(trifluoromethyl)pyridin-2-yl)-1,3,4-oxadiazol-2-yl)(phenyl)methylcarbamate (step 2) (55 mg, 0.100 mmol) in dry DCM (6 ml) was added iodotrimethylsilane (55 ul, 0.401 mmol) under nitrogen. The reaction mixture was stirred at RT overnight. Purification was carried out using an SPE cartridge (Isolute® SCX-2) eluting with MeOH followed by 3.5M ammonia in MeOH (5 ml) to afford the title compound; 1H NMR (400 MHz, DMSO-d6) δ 7.85 (1H, s), 7.50 (2H, d), 7.49 (2H, t), 7.31 (5H), 5.49 (1H, s). LC-MS Rt=1.39 min [M+H]+ 416.1 Method 2minLC_v002.

Example 12.0

2-(5-(3-Amino-5-(trifluoromethyl)pyridin-2-yl)-1,3,4-thiadiazol-2-yl)-1,1,1-trifluoro propan-2-ol

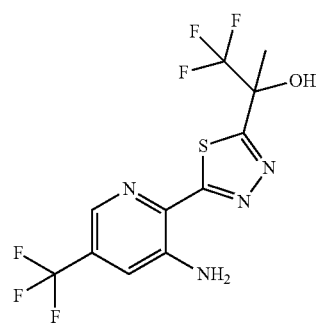 [SMILES: CC(O)(c1nnc(-c2ncc(C(F)(F)F)cc2N)s1)C(F)(F)F]

Step 1: 3-Amino-N'-(3,3,3-trifluoro-2-hydroxy-2-methylpropanoyl)-5-(trifluoromethyl) picolinohydrazide To 3,3,3-trifluoro-2-hydroxy-2-methylpropanoic acid (324 mg, 2.049 mmol) in NMP (5 ml) was added HATU (935 mg, 2.458 mmol) and DIPEA (1.073 ml, 6.15 mmol). After stirring for 5 minutes 3-amino-5-(trifluoromethyl)picolinohydrazide (Intermediate I) (451 mg, 2.049 mmol) was added and stirring continued at RT for 1 h. The reaction mixture was diluted with water and extracted with EtOAc. The combined organic extracts were washed with 1M HCl (100 ml), water (2×100 ml), brine and dried (phase separator) and concentrated in vacuo. Purification by chromatography on silica eluting with 0-30% EtOAc in iso-hexane afforded the title compound; 1H NMR 400 MHz, DMSO-d6: δ 10.3 (1H, s), 10.0 (1H, s), 8.0 (1H, s), 7.5 (1H, s), 7.1 (3H, s, overlap), 1.5 (3H, s). LC-MS Rt=0.98 min [M+H]+ 361.2 Method 2min-LC_v003.

Step 2: 2-(5-(3-Amino-5-(trifluoromethyl)pyridin-2-yl)-1,3,4-thiadiazol-2-yl)-1,1,1-trifluoropropan-2-ol A mixture comprising 3-amino-N'-(3,3,3-trifluoro-2-hydroxy-2-methylpropanoyl)-5-(trifluoromethyl) picolinohydrazide (184 mg, 0.511 mmol) in toluene (5.108 ml) was treated with Lawesson reagent (310 mg, 0.766 mmol) and heated at reflux for 1 h. The reaction mixture was diluted with water and extracted with EtOAc. The combined organic extracts were washed saturated sodium bicarbonate solution, brine, dried (phase separator) and concentrated in vacuo. Purification by chromatography on silica eluting with 0-30% EtOAc in iso-hexane afforded an orange gum. Further purification was carried out by preparative reverse phase HPLC eluting with 30-70% MeCN in water (0.1% TFA) to afford the title compound; 1H NMR (400 MHz, DMSO-d6) δ 8.2 (1H, s), 8.0 (1H, s), 7.6 (1H, s), 7.4 (2H, s), 1.9 (3H, s). LC-MS Rt=4.03 min [M+H]+ 359.4 Method 10minLC_v003.

Example 13.0

(R)-2-[5-(3-Amino-4-chloro-6-methoxy-5-trifluoromethyl-pyridin-2-yl)-[1,3,4]oxadiazol-2-yl]-1,1,1-trifluoro-propan-2-ol

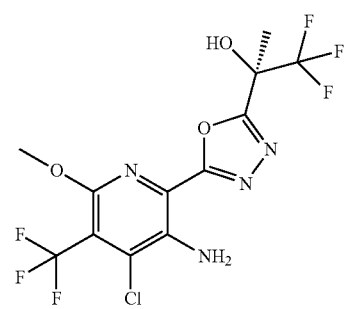 [SMILES: COc1nc(-c2nnc([C@@](C)(O)C(F)(F)F)o2)c(N)c(Cl)c1C(F)(F)F]

To (R)-2-(5-(3-amino-6-methoxy-5-(trifluoromethyl)pyridin-2-yl)-1,3,4-oxadiazol-2-yl)-1,1,1-trifluoropropan-2-ol (Example 2) (150 mg, 0.403 mmol) in acetonitrile (1 ml) was added trichloroisocyanuric acid (37.5 mg, 0.161 mmol) and the resulting mixture was heated using microwave radiation at 100° C. for 30 minutes followed by 125° C. for 10 minutes. The mixture was partitioned between EtOAc and water. The organic portion was separated and washed with sat.NaHCO3, brine, dried (MgSO4) and concentrated in vacuo. Purification of the crude product by chromatography on silica eluting with 0-30% EtOAc in iso-hexane afforded the title compound;

LC-MS Rt=4.40 min [M+H]+ 407.1 Method 10min-LC_v003.

1H NMR (400 MHz, DMSO-d6) δ 7.80 (1H, s), 6.90 (2H, s), 3.95 (3H, s), 1.87 (3H, s)

Example 13.1

(S)-2-(5-(3-Amino-4-chloro-6-methoxy-5-(trifluoromethyl)pyridin-2-yl)-1,3,4-oxadiazol-2-yl)-1,1,1-trifluoropropan-2-ol

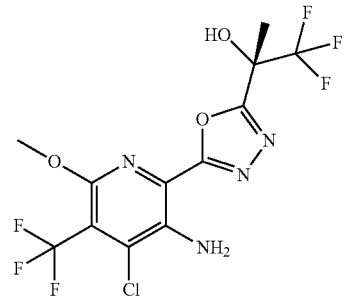 [SMILES: COc1nc(-c2nnc([C@](C)(O)C(F)(F)F)o2)c(N)c(Cl)c1C(F)(F)F]

The title compound was prepared analogously to Example 13.0 by replacing (R)-2-(5-(3-amino-6-methoxy-5-(trifluoromethyl)pyridin-2-yl)-1,3,4-oxadiazol-2-yl)-1,1,1-trifluoropropan-2-ol (Example 2) with (S)-2-(5-(3-amino-6-methoxy-5-(trifluoromethyl)pyridin-2-yl)-1,3,4-oxadiazol-2-yl)-1,1,1-trifluoropropan-2-ol (Example 3);

LC-MS Rt=1.25 min [M+H]+ 407.1 Method 2min-LC_v003.

1H NMR (400 MHz, DMSO-d6) δ 7.81 (1H, s), 6.90 (2H, s), 3.96 (3H, s), 1.88, (3H, s).

Example 14.0

(S)-2-[5-(3-Amino-4-ethyl-6-methoxy-5-trifluoromethyl-pyridin-2-yl)-[1,3,4]oxadiazol-2-yl]-1,1,1-trifluoro-propan-2-ol

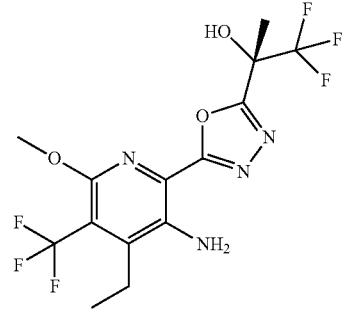 [SMILES: CCc1c(N)c(-c2nnc([C@](C)(O)C(F)(F)F)o2)nc(OC)c1C(F)(F)F]

Step 1: (S)-2-(5-(3-Amino-6-methoxy-5-(trifluoromethyl)-4-vinylpyridin-2-yl)-1,3,4-oxadiazol-2-yl)-1,1,1-trifluoropropan-2-ol To a solution of (S)-2-(5-(3-amino-4-chloro-6-methoxy-5-(trifluoromethyl)pyridin-2-yl)-1,3,4-oxadiazol-2-yl)-1,1,1-trifluoropropan-2-ol (Ex 13.1) (160 mg, 0.393 mmol) in MeCN (1 ml) was added bis(triphenyl phosphine)palladium (II) chloride (Aldrich) (83 mg, 0.118 mmol) followed by 4,4,5,5-tetramethyl-2-vinyl-1,3,2-dioxaborolane (Sigma Aldrich)(0.087 ml, 0.511 mmol). 2M Sodium carbonate (0.885 ml, 1.770 mmol) was added and the resulting mixture was heated at 130° C. for 30 minutes using microwave radiation. The mixture was filtered through Celite® and washed through with EtOAc. The filtrate was diluted further with EtOAc (50 ml) and washed with sat.NaHCO$_3$, water, brine and dried over MgSO$_4$. Isolute Si-TMT (2,4,6-trimercaptotriazine silica, palladium scavenger) was added the mixture was stirred for 30 mins and filtered. The solvent was removed in vacuo to afford the title compound which was used without further purification;
LC-MS Rt=1.25 min [M+H]+ 399.3 Method 2min-LC_v003.

Step 2: (S)-2-[5-(3-Amino-4-ethyl-6-methoxy-5-trifluoromethyl-pyridin-2-yl)-[1,3,4]oxadiazol-2-yl]-1,1,1-trifluoro-propan-2-ol To a stirring solution of (S)-2-(5-(3-amino-6-methoxy-5-(trifluoromethyl)-4-vinylpyridin-2-yl)-1,3,4-oxadiazol-2-yl)-1,1,1-trifluoropropan-2-ol (step 1)(153 mg, 0.384 mmol) in EtOH (10 ml) was added palladium hydroxide on carbon (43.2 mg, 0.307 mmol) followed by ammonium formate (969 mg, 15.37 mmol). The reaction mixture was heated at reflux for 30 minutes. The mixture was filtered through Celite® and diluted with EtOAc. The filtrate and washed with sat-.NaHCO$_3$, water, brine and dried over MgSO$_4$. Isolute Si-TMT (2,4,6-trimercaptotriazine silica, palladium scavenger) was added the mixture was stirred for 30 mins and filtered. The solvent was removed in vacuo and purification of the crude product by chromatography on silica eluting with 0-30% EtOAc in iso-hexane afforded the title compound;
LC-MS Rt=4.49 min [M+H]+ 401.2 Method 10min-LC_v003.
1H NMR (400 MHz, DMSO-d6) δ 7.76 (1H, s), 6.72 (2H, s), 3.91 (3H, s), 2.85 (2H, m), 1.87 (3H, s), 1.17 (3H, t).

Example 14.1

(S)-2-[5-(3-Amino-4-isopropenyl-6-methoxy-5-trifluoromethyl-pyridin-2-yl)-[1,3,4]oxadiazol-2-yl]-1,1,1-trifluoro-propan-2-ol

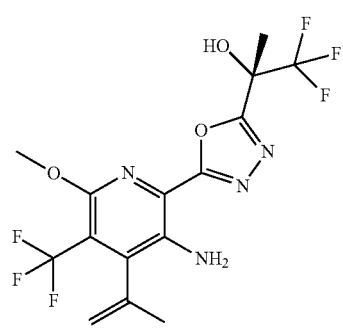 [SMILES: C=C(C)c1c(N)c(-c2nnc([C@](C)(O)C(F)(F)F)o2)nc(OC)c1C(F)(F)F]

The title compound was prepared analogously to (S)-2-(5-(3-Amino-6-methoxy-5-(trifluoromethyl)-4-vinylpyridin-2-yl)-1,3,4-oxadiazol-2-yl)-1,1,1-trifluoropropan-2-ol (Example 14.0 step 1) by replacing 4,4,5,5-tetramethyl-2-vinyl-1,3,2-dioxaborolane with 4,4,5,5-tetramethyl-2-(prop-1-en-2-yl)-1,3,2-dioxaborolane;
LC-MS Rt=4.80 min [M+H]+ 413.2 Method 10min-LC_v003.
1H NMR (400 MHz, DMSO-d6) δ 7.77 (1H, s), 6.33 (2H, s), 5.48 (1H, s), 5.00 (1H, s), 3.94 (3H, s), 2.01 (3H, s), 1.87 (3H, s).

Example 14.2

(S)-2-[5-(3-Amino-4-isopropyl-6-methoxy-5-trifluoromethyl-pyridin-2-yl)-[1,3,4]oxadiazol-2-yl]-1,1,1-trifluoro-propan-2-ol

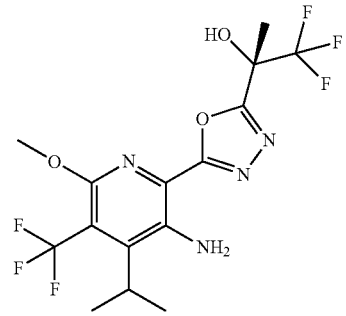 [SMILES: COc1nc(-c2nnc([C@](C)(O)C(F)(F)F)o2)c(N)c(C(C)C)c1C(F)(F)F]

The title compound was prepared from (S)-2-[5-(3-amino-4-isopropenyl-6-methoxy-5-trifluoromethyl-pyridin-2-yl)-[1,3,4]oxadiazol-2-yl]-1,1,1-trifluoro-propan-2-ol (Ex. 14.1) and prepared analogously to (S)-2-[5-(3-amino-4-ethyl-6-methoxy-5-trifluoromethyl-pyridin-2-yl)-[1,3,4]oxadiazol-2-yl]-1,1,1-trifluoro-propan-2-ol (Ex. 14.0 step 2);
LC-MS Rt=4.95 min [M+H]+ 415.2 Method 10min-LC_v003.
1H NMR (400 MHz, DMSO-d6) δ 7.76 (1H, s), 6.51 (2H, s), 3.90 (3H, s), 3.60 (1H, m), 1.87 (3H, s), 1.41 (6H, d).

Example 14.3

(S)-2-[5-(3-Amino-6-methoxy-4-phenyl-5-trifluoromethyl-pyridin-2-yl)-[1,3,4]oxadiazol-2-yl]-1,1,1-trifluoro-propan-2-ol

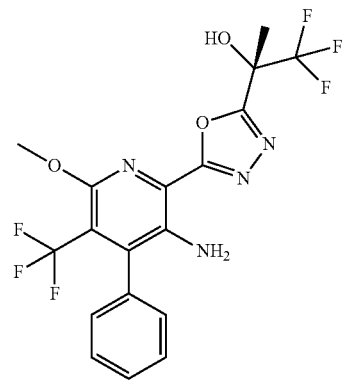 [SMILES: COc1nc(-c2nnc([C@](C)(O)C(F)(F)F)o2)c(N)c(-c2ccccc2)c1C(F)(F)F]

The title compound was prepared analogously to (S)-2-(5-(3-Amino-6-methoxy-5-(trifluoromethyl)-4-vinylpyridin-2-yl)-1,3,4-oxadiazol-2-yl)-1,1,1-trifluoropropan-2-ol (Example 14.0 step 1) by replacing 4,4,5,5-tetramethyl-2-vinyl-1,3,2-dioxaborolane with 4,4,5,5-tetramethyl-2-phenyl-1,3,2-dioxaborolane;

LC-MS Rt=4.98 min [M+H]+ 449.3 Method 10min-LC_v003.

1H NMR (400 MHz, DMSO-d6) δ 7.79 (1H, s), 7.56 (3H, m), 7.30 (2H, m), 5.80 (2H, s), 3.99 (3H, s), 1.88 (3H, s)

Preparation of Intermediates

Intermediate A

3-Amino-6-bromo-5-trifluoromethyl-pyridine-2-carboxylic acid

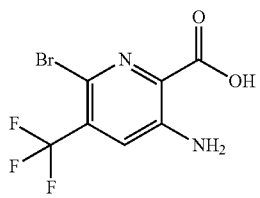 [SMILES: Nc1cc(C(F)(F)F)c(Br)nc1C(=O)O]

Intermediate A1:
2-Bromo-3-nitro-5-trifluoromethyl-pyridine

3-Nitro-5-(trifluoromethyl)pyridin-2-ol (31.00 g, 149 mmol) was dissolved in acetonitrile (250 ml) to give a dark brown solution. Phosphorus(V) oxybromide (85 g, 298 mmol) was added and the mixture was heated at reflux for 4 hours and then stirred at RT overnight. The reaction mixture was quenched by pouring into vigorously stirring water (600 ml) containing sodium hydrogencarbonate (110 g). The dark brown mixture was extracted with DCM (3×200 ml) and the organic phase was washed with water (200 ml) and brine (100 ml), dried (MgSO₄) and concentrated in vacuo to afford the title product as a brown oil. ¹H-NMR: [400 MHz, CDCl₃, δ 8.87 (1H, d, J=1.4 Hz, ArH), 8.39 (1H, d, J=1.9 Hz, ArH).

Intermediate A2:
3-Nitro-5-trifluoromethyl-pyridine-2-carbonitrile

2-Bromo-3-nitro-5-trifluoromethyl-pyridine (10.00 g, 36.87 mmol) was dissolved in toluene (250 ml) with stirring to give a pale yellow solution. Tetrabutylammonium bromide (11.90 g, 36.9 mmol) was added followed by copper(I) cyanide (9.92 g, 111 mmol) and the mixture was heated at reflux for 9 hrs. After cooling to RT, the reaction mixture was partitioned between water (750 ml) and EtOAc (750 ml). The organic fractions were combined, washed with water (2×250 ml) and brine (100 ml), dried (MgSO₄) and concentrated in vacuo to afford the title product. ¹H-NMR: [400 MHz, DMSO-d₆] δ 9.55 (1H, m, ArH), 9.24 (1H, m, ArH)

Intermediate A3:
3-Amino-5-trifluoromethyl-pyridine-2-carboxylic acid methyl ester 3-Nitro-5-trifluoromethyl-pyridine-2-carbonitrile (6.5 g, 29.9 mmol) was dissolved in EtOAc (150 ml) to give a pale yellow solution. 10% Palladium on activated carbon (3.19 g, 2.99 mmol) was added and the reaction mixture stirred under an atmosphere of hydrogen for 18 hours. The reaction mixture was filtered and concentrated in vacuo. The crude residue was dissolved in HCl conc. (45 ml) and heated to reflux for 24 hours. The reaction mixture was allowed to cool to RT and concentrated in vacuo. The solid was dissolved in MeOH (200 ml) and sulfuric acid (8 ml) was added. The resulting solution was heated at reflux for 84 hours. The reaction was allowed to cool to RT, then neutralised by addition of 10% NaHCO₃(aq) (600 ml). The product was extracted into DCM (3×200 mL) and the combined organic phases were washed with water (200 ml), brine (50 mL), (MgSO₄) and concentrated in vacuo. The resulting solid was purified by chromatography on silica: Eluant gradient: isohexane (500 ml), 10% EtOAc in isohexane (1000 mL), 20% EtOAc in isohexane (1500 mL) to afford the titled compound as a pale yellow solid ¹H-NMR: [400 MHz, DMSO-d₆] δ 8.13 (1H, d, J=1.7 Hz, ArH), 7.60 (1H, d, J=1.3 Hz, ArH), 7.01 (2H, br, NH₂), 3.85 (3H, s, ArOCH₃), m/z 221.1 [M+H]⁺

Intermediate A4: 3-Amino-6-bromo-5-trifluoromethyl-pyridine-2-carboxylic acid methyl ester 3-Amino-5-trifluoromethyl-pyridine-2-carboxylic acid methyl ester (9.49 g, 43.16 mmol) was dissolved in water (300 mL). Sulfuric acid (4.60 mL, 86 mmol) was added followed by dropwise addition over 30 minutes of a solution of bromine (2.222 mL, 43.1 mmol) in acetic acid (29.6 mL, 517 mmol). The reaction mixture was stirred at RT for 18 hours. A further 100 ml of water was added, followed by a further 0.25 equivalents of the bromine/AcOH mixture (550 µL bromine in 7.4 mL AcOH) and the reaction mixture stirred at RT for an additional 90 minutes. The reaction mixture was diluted with 500 mL water and neutralised by addition of solid NaHCO₃ (~85 g). The suspension was extracted with DCM (3×300 mL) and the combined organic phases washed with sat.NaHCO₃(aq) (250 mL), water (250 mL) and brine (100 mL), dried (MgSO₄) and concentrated in vacuo. The crude material was recrystallised from boiling MeOH (~300 mL) to give the title product as a pale orange solid m/z 301.0 [M+H]⁺ ¹H-NMR: [400 MHz, DMSO-d₆] δ 7.77 (1H, s, ArH), 7.17 (2H, s, NH₂), 3.86 (3H, s, ArCO₂CH₃).

Intermediate A: 3-Amino-6-bromo-5-trifluoromethyl-pyridine-2-carboxylic acid

3-Amino-6-bromo-5-trifluoromethyl-pyridine-2-carboxylic acid methyl ester (1.40 g, 4.68 mmol) was suspended in MeOH (15 mL); Sodium hydroxide (2.0 M aqueous solution) (14.04 mL, 28.1 mmol) was added and the suspension was stirred at RT overnight. The reaction mixture was concentrated in vacuo and the resulting residue was dissolved in water (100 mL) and then acidified by the addition of 5.0M HCl(aq). The product was extracted into ethyl acetate (2×75 mL) and the combined organic extracts were washed with water (50 mL), brine (25 mL), dried (MgSO₄) and concentrated in vacuo to afford the title product as a yellow solid.

¹H-NMR: [400 MHz, DMSO-d₆] δ 13.24 (1H, br s, CO₂H), 7.74 (1H, s, ArH), 7.17 92H, br s ArNH₂). m/z 285.1, 287.1 [M+H]⁺

Intermediate B

3-Amino-6-methoxy-5-trifluoromethyl-pyridine-2-carboxylic acid

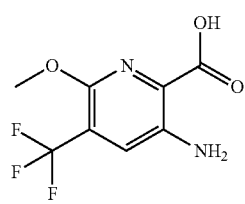

Intermediate B1: 6-Bromo-3-(2,5-dimethyl-pyrrol-1-yl)-5-trifluoromethyl-pyridine-2-carboxylic acid methyl ester

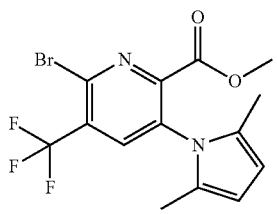 [SMILES: COC(=O)c1nc(Br)c(C(F)(F)F)cc1-n1c(C)ccc1C]

3-Amino-6-bromo-5-trifluoromethyl-pyridine-2-carboxylic acid methyl ester (Intermediate A4) (2 g, 6.69 mmol) was suspended in toluene (8 ml), then p-toluenesulfonic acid (TsOH) (0.115 g, 0.669 mmol) and acetonylacetone (0.941 ml, 8.03 mmol) was added. The reaction mixture was heated at reflux for 2 hrs and allowed to cool to RT overnight. The resulting dark red/black solution was concentrated in vacuo to remove toluene and the crude residue diluted with 200 ml EtOAc, washed with NaHCO₃ (50 ml), dried (MgSO₄) and concentrated in vacuo to give a brown solid; LC-MS Rt=5.58 min [M+H]+ 377/379 (Method 10minLC_v002).

1H NMR (400 MHz, DMSO-d6) δ 8.50 (1H, s), 7.77 (2H, s), 5.83 (3H, s), 1.90 (6H, s);
19F NMR (400 MHz, DMSO-d6) δ -62.26 (CF3, s)

Intermediate B2: 3-(2,5-Dimethyl-pyrrol-1-yl)-6-methoxy-5-trifluoromethyl-pyridine-2-carboxylic acid

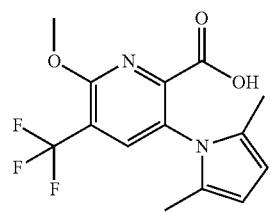 [SMILES: COc1nc(C(=O)O)c(-n2c(C)ccc2C)cc1C(F)(F)F]

6-Bromo-3-(2,5-dimethyl-pyrrol-1-yl)-5-trifluoromethyl-pyridine-2-carboxylic acid methyl ester (2 g, 5.30 mmol) was dissolved in MeOH (40 ml) and treated with 2M NaOH (20 ml) to give a suspension which was stirred at RT for 1 hr to afford a clear solution. The solvent was removed in vacuo and the residue was acidified to pH1 with 5M HCl. The mixture was extracted with EtOAc (200 ml) and the organic extract was dried (MgSO₄) and concentrated in vacuo to afford the title compound as a dark brown solid which was used in the next step without further purification; LC_MS Rt=1.50 min [M+H]+ 315.2.1/316.2 (Method 2minLC_v002); 1H NMR (400 MHz, DMSO-d6) δ14.42-12.61 (COOH, b hump), 8.25 (1H, s), 5.84 (2H, s), 4.13 (3H, s), 1.97 (6H, s); 19F NMR (400 MHz, DMSO-d6) δ -62.43 (CF3, s).

Intermediate B: 3-Amino-6-methoxy-5-trifluoromethyl-pyridine-2-carboxylic acid 3-(2,5-Dimethyl-pyrrol-1-yl)-6-methoxy-5-trifluoromethyl-pyridine-2-carboxylic acid (833 mg, 2.65 mmol) was dissolved in EtOH (45 ml) and water (23 ml). To this mixture was added TEA (1.102 ml, 7.95 mmol) followed by hydroxylamine hydrochloride (1842 mg, 26.5 mmol). The resulting mixture was heated at reflux overnight. After cooling to RT, the mixture was stirred with 20 g Isolute® PE-AX (silica-based sorbent with a chemically bonded quaternary amine functional group used for isolation of acidic compounds) for 30 mins, washed with MeOH (100 ml), 1M HCl: MeCN 2:8 (200 ml). The organic portion was removed and the mixture was filtered. The filtrate was acidified with 2M HCl (50 ml) and the EtOH was removed in vacuo. The aqueous portion was extracted with DCM (200 ml) and the organic extract was dried (MgSO4) and concentrated in vacuo to give a brown oil. Purification by chromatography on silica eluting with DCM: MeOH afforded the title product as a yellow solid: LC-MS Rt=2.90 min [M+H]+ 237 (Method 10minLC_v002)

1H NMR (400 MHz, DMSO-d6) δ 9.62-7.79 (NH2, b hump), 7.70 (1H, s), 3.89 (3H, s);
19F NMR (400 MHz, DMSO-d6) δ -62.92 (CF3, s).

Intermediate C tert-Butyl 2-(hydrazinecarbonyl)-6-methoxy-5-(trifluoromethyl)pyridin-3-yl carbamate

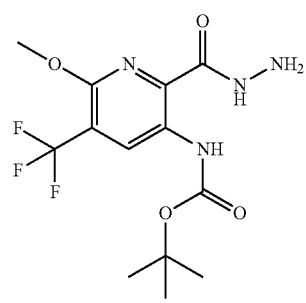 [SMILES: COc1nc(C(=O)NN)c(NC(=O)OC(C)(C)C)cc1C(F)(F)F]

Int. C1: Methyl 3-amino-6-methoxy-5-(trifluoromethyl)picolinate

3-Amino-6-methoxy-5-trifluoromethyl-pyridine-2-carboxylic acid (Int. B) 5.5 g, 23.29 mmol) was dissolved in MeOH (90 ml). H₂SO₄ (6.21 ml, 116 mmol) was added dropwise and the solution was heated to reflux for 4 hours. The reaction mixture was reduced in vacuo to approx. 15 ml and water (15 ml) was added. The pH was adjusted to pH 9 by careful addition of solid NaHCO$_3$. Water (100 ml) was added and the mixture was extracted with DCM. The combined organic extracts were concentrated in vacuo to afford the title compound.

Int. C2: Methyl 3-(tert-butoxycarbonylamino)-6-methoxy-5-(trifluoromethyl)picolinate To a stirring solution of methyl 3-amino-6-methoxy-5-(trifluoromethyl)picolinate (step 1) (4.989 g, 19.94 mmol) in DCM (100 ml) was added DIPEA (2.84 g, 21.94 mmol), boc anhydride (4.79 g, 21.94 mmol) followed by DMAP (2.436 g, 19.94 mmol). After stirring for 3 h, the reaction mixture was washed with water (3 times), dried (MgSO$_4$) and concentrated in vacuo. The crude product was purified by chromatography on silica, eluting in a 0% to 10% iso-hexane: EtOAc to afford the title compound.

Int. C: tert-Butyl 2-(hydrazinecarbonyl)-6-methoxy-5-(trifluoromethyl)pyridin-3-ylcarbamate A suspension of methyl 3-(tert-butoxycarbonylamino)-6-methoxy-5-(trifluoromethyl)picolinate (step 2) (3.1 g, 8.85 mmol) in dry MeOH (20 ml) was treated with hydrazine monohydrate (1.108 g, 22.12 mmol) and the suspension was heated at reflux overnight. The mixture was diluted with water and the resulting precipitate was collected by filtration and dried in a vacuum oven to afford the title compound as a light brown solid (3.01 g). LC-MS Rt=1.27 min [M+H]+ 251 [–minus Boc group] (Method HighpH_v003.).

Intermediate D 2-(Benzyloxy)-3,3,3-trifluoro-2-methylpropanoic acid

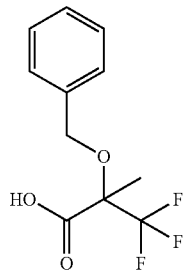 [SMILES: CC(OCc1ccccc1)(C(=O)O)C(F)(F)F]

Int. D1: Benzyl 3,3,3-trifluoro-2-hydroxy-2-methylpropanoate 3,3,3-Trifluoro-2-hydroxy-2-methylpropanoic acid (0.6 g, 3.80 mmol) was dissolved in MeCN (5 ml). DIPEA (0.663 ml, 3.80 mmol) was added and stirred for 5 min. Benzyl bromide (541 mg, 3.16 mmol) was added and the reaction mixture was stirred at RT for 16 h followed by 70° C. for 16 h. After cooling to RT, the solvent was removed in vacuo and the resulting residue was dissolved in DCM. The mixture was washed with water and the organic portion was separated by means of a phase separator. The solvent was removed in vacuo to afford the title compound.

Int. D2: Benzyl 2-(benzyloxy)-3,3,3-trifluoro-2-methylpropanoate

A cooled (0° C.) solution of benzyl 3,3,3-trifluoro-2-hydroxy-2-methylpropanoate (Int. D1) (100 mg, 0.403 mmol) in DMF (4 ml) was treated with sodium hydride (16.11 mg, 0.403 mmol) followed by benzyl bromide (0.048 ml, 0.403 mmol) and stirred at 0° C. for 2 h. The reaction mixture was allowed to warm to room temperature and stirring continued for a further 3 hrs. The reaction mixture was partitioned between EtOAc and 0.1M HCl solution. The organic phase was washed with saturated brine, dried over magnesium sulfate and concentrated in vacuo to afford the title compound as an oil.

Int D3: 2-(Benzyloxy)-3,3,3-trifluoro-2-methylpropanoic acid

Benzyl 2-(benzyloxy)-3,3,3-trifluoro-2-methylpropanoate (Int. D3)(170 mg, 0.502 mmol) in MeOH (5 ml) was treated with 2M sodium hydroxide (0.502 ml, 1.005 mmol) 2M and stirred at RT for 2 h. The methanol was removed in vacuo and the residue was dissolved in water and washed with EtOAc. The aqueous phase acidified with 5M HCl and extracted with EtOAc. The combined organic extracts were washed with saturated brine, dried over magnesium sulfate and concentrated in vacuo afford the title product as a clear; $^1$H NMR (400 MHz, DMSO-d6) δ 14.08 (1H, br s), 7.35 (5H, m), 4.62 (2H, dd), 1.64 (3H, s).

Intermediate E

3-Amino-5-trifluoromethyl-pyrazine-2-carboxylic acid ethyl ester

Int. E1: Carbamimidoyl-nitroso-acetic acid ethyl ester

To a solution of 2M ammonia in EtOH (152 ml, 0.304 mmol) at 0° C. to 5° C., ethyl ethoxycarbonylacetimidate HCl (25 g, 0.127 mmol) was added over 30 minutes. The reaction was stirred vigorously at this temperature for 3 hours, after which a solution of sodium nitrile in water (9.63 g, 0.139 mmol) was added in a single portion. The pH of the mixture was adjusted to pH6 with the addition of 5N HCl. The reaction mixture was left to stir at RT overnight. The yellow precipitate formed was filtered under vacuum, washed with water and dried to give the title compound;
$^1$H NMR (400 MHz, DMSO-d6) δ 10.1 (2H, br s), 7.6 (2H, br s), 4.3 (2H, q), 1.3 (3H, t).

Int. E2: Amino-carbamimidoyl-acetic acid ethyl ester

To a solution of carbamimidoyl-nitroso-acetic acid ethyl ester (5.5 g, 31.4 mmol) in ethanol/5M HCl (1:1 ratio, 250 ml) was added 10% Pd/C (1.3 g). The reaction mixture was hydrogenated (H$_{2(g)}$) at low pressure over 2 nights. The Pd/C was filtered through Celite® (filter material) and the filtrate reduced in vacuo to give the title compound as a white solid. This was taken through to the next step as crude.

Int. E: 3-Amino-5-trifluoromethyl-pyrazine-2-carboxylic acid ethyl ester

To a mixture of amino-carbamimidoyl-acetic acid ethyl ester (2 g, 9.22 mmol) and water (50 ml), a 20% aqueous solution of trifluoropyruvic aldehyde (2.32 g, 18.43 mmol) was added. To this mixture, sodium acetate (5.29 g, 64.52 mmol) was added (pH of the reaction mixture was pH5). The reaction mixture was left to stir at RT overnight. The resultant precipitate was filtered under vacuum purification by chromatography on silica eluting with iso-hexane:EtOAc (gradient of 0 to 10% EtOAc) afforded the title compound $^1$H NMR (400 MHz, DMSO-d6) δ 8.4 (1H, s), 7.8 (2H, br s), 4.4 (2H, q), 1.4 (3H, t).

Intermediate F

3-Amino-6-bromo-5-trifluoromethyl-pyrazine-2-carboxylic acid

Int. F1: 3-Amino-6-bromo-5-trifluoromethyl-pyrazine-2-carboxylic acid ethyl ester To a solution of 3-amino-5-trifluoromethyl-pyrazine-2-carboxylic acid ethyl ester (Int. E) (30 mg, 0.13 mmol) in acetic acid (5 ml), sodium carbonate (15 mg, 0.14 mmol) was added. To this mixture, half the contents of a solution of bromine (7 μL, 0.13 mmol) in acetic acid (5 ml) was added, followed by the addition of sodium carbonate ((15 mg, 0.14 mmol). The remaining solution of bromine in acetic acid was added and the reaction mixture was left to stir at RT for 2 hours. The mixture was diluted with water and the resulting yellow precipitate was filtered under vacuum to afford the title compound.

Int. F: 3-Amino-6-bromo-5-trifluoromethyl-pyrazine-2-carboxylic acid

To a stirring solution of 3-amino-5-trifluoromethyl-pyrazine-2-carboxylic acid ethyl ester (10 g, 31.8 mmol) in ethanol (20 ml), 2M NaOH (20 ml, 31.8 mmol) was added.

The resulting solution was stirred at RT for 5 minutes and poured into water (50 ml). The pH was adjusted to pH6 with the addition of 1M HCl. The resulting suspension was filtered under vacuum, washed with water (20 ml) and dried to afford the title compound;

$^1$H NMR (400 MHz, DMSO-d6) δ 7.98 (2H, s).

Intermediate G

3-Amino-5,6-bis(trifluoromethyl)pyrazine-2-carbohydrazide

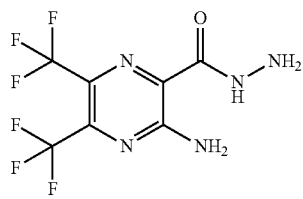 [SMILES: NNC(=O)c1nc(C(F)(F)F)c(C(F)(F)F)nc1N]

Int. G1: Ethyl 3-amino-5,6-bis(trifluoromethyl)pyrazine-2-carboxylate

To a solution of amino-carbamimidoyl-acetic acid ethyl ester (Int E2)(1.25 g, 8.61 mmol) in DMF (5 ml) was added 1,1,1,4,4,4-hexafluorobutane-2,3-dione (5 g, 25.8 mmol) and the mixture was stirred at RT for 25 days. The yellow suspension was partitioned between EtOAc (50 ml) and water (50 ml) and the organic portion was washed with brine (30 ml), dried (MgSO$_4$) and concentrated in vacuo. The crude product was purified by mass directed LC-MS eluting with MeCN/Water/0.1% TFA. The clean fractions were poured into EtOAc (50 ml) and washed with saturated NaHCO$_3$ (50 ml), dried (MgSO$_4$) and concentrated in vacuo to afford the title compound; 19F NMR (400 MHz, DMSO-d6): Peak 1 at −62 ppm, peak 2 at −64.6 ppm Int. G: 3-Amino-5,6-bis(trifluoromethyl)pyrazine-2-carbohydrazide A suspension of ethyl 3-amino-5,6-bis(trifluoromethyl) pyrazine-2-carboxylate (Int. G1)(455 mg, 1.501 mmol) in MeOH (10 ml) was treated with hydrazine monohydrate (0.147 ml, 3.00 mmol) and stirred at RT overnight. The reaction mixture was diluted with water (50 ml) and the pH was adjusted to pH4-5 using 1M HCl. A yellow precipitate formed which was filtered under vacuum, washed with water and air dried to afford the title compound which was used without further purification;

LC-MS Rt=0.9 min [M+H]+ 290.1 Method 2min-LC_v003.

1H NMR (400 MHz, DMSO-d6): δ 10 (1H, s), 8.54 (2H, br hump), 4.69 (2H, s).

Intermediate H

3-Amino-6-bromo-5-(trifluoromethyl)picolinohydrazide

A suspension of 3-amino-6-bromo-5-trifluoromethyl-pyridine-2-carboxylic acid methyl ester (Intermediate A4) (1.00 g, 3.34 mmol) in dry MeOH (20 ml) was stirred at reflux (85° C.) for 30 min and then treated with hydrazine monohydrate (324 ul, 6.69 mmol). The mixture was returned to heat at reflux for 5 h 30 min and allowed to cool to RT. Water was added and the resulting precipitate was collected by filtration and dried in a vacuum oven to afford the title compound as a biege solid;

1H NMR (400 MHz, DMSO-d6) δ 9.50 (1H, s), 7.69 (1H, s), 7.19 (2H, s), 4.55 (2H).

LCMS: Rt=1.15 min; [M+H]+ 299 Method 2min-LC_v002.

Intermediate I

3-Amino-5-(trifluoromethyl)picolinohydrazide

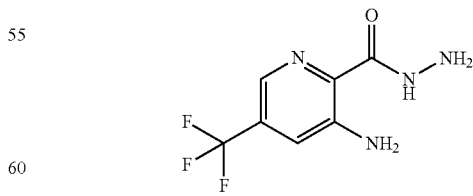

The title compound was prepared analogously to Intermediate H by replacing 3-amino-6-bromo-5-trifluoromethyl-pyridine-2-carboxylic acid methyl ester (Intermediate A4) with 3-Amino-5-trifluoromethyl-pyridine-2-carboxylic acid methyl ester (Intermediate A3);

LC-MS Rt=0.93 min [M+H]+ 221.1 (Method 2min-LC_v002).

1H NMR (400 MHz, DMSO-d6) δ 9.80 (1H, s), 8.05 (1H, s), 7.51 (1H, s), 7.10 (2H, s), 4.50 (2H, s).

Intermediate JR and JS

R)-Benzyl 2-hydrazinyl-2-oxo-1-phenylethylcarbamate (Int JR) and (S)-benzyl 2-hydrazinyl-2-oxo-1-phenylethylcarbamate (Int JS A solution of (R)-ethyl 2-(benzyloxycarbonylamino)-2-phenylacetate (2.5 g, 7.98 mmol) in EtOH (20 ml) was treated with hydrazine monohydrate (1.956 ml, 39.9 mmol) and stirred at RT for 6 days. The resulting suspension was concentrated in vacuo to afford a white solid. Purification was carried out using chiral separation under the following conditions to yield the title compounds:

Instrumentation: Gilson

Injection Volume: 12 ml

Mobile Phase: n-heptane:EtOH 60:40 (v/v)

Flow Rate: 60 ml/min

Column: Chiralpak AS 200×500 mm, 20 μm

Detection UV: 220 nm

Intermediate JR: (R)-benzyl 2-hydrazinyl-2-oxo-1-phenylethylcarbamate

1H NMR (400 MHz, DMSO-d6) d 9.42 (NH, s), 7.94 (NH, d), 7.43 (2H, d), 7.35-7.25 (8H, m), 5.21 (1H, d), 5.03 (2H, t), 4.28 (NH2, b s)

Intermediate JS: (S)-benzyl 2-hydrazinyl-2-oxo-1-phenylethylcarbamate

1H NMR (400 MHz, DMSO-d6) d 9.42 (NH, s), 7.94 (NH, d), 7.43 (2H, d), 7.35-7.25 (8H, m), 5.21 (1H, d), 5.07 (2H, q), 4.28 (NH2, b s)

From the foregoing it will be appreciated that, although specific embodiments of the invention have been described herein for purposes of illustration, various modifications may be made without deviating from the spirit and scope of the invention. Accordingly, the invention is not limited except as by the appended claims.

EMBODIMENTS

Embodiment 1

A compound of Formula I

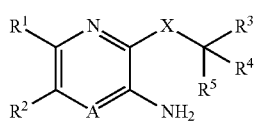

wherein:

A is N or $CR^{4a}$;

X is

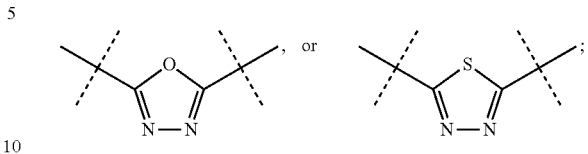

$R^1$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; halogen; $SO_2NR^8R^9$; $SO_2R^{19}$; S—$C_1$-$C_8$alkyl optionally substituted by one or more halogen atoms; S—$C_6$-$C_{14}$ aryl; —($C_0$-$C_4$ alkyl)-$C_6$-$C_{14}$ aryl; and —($C_0$-$C_4$ alkyl)-3 to 14 membered heterocyclyl; wherein the heterocyclyl contains at least one heteroatom selected from N, O and S; CN; $NR^{11}R^{12}$; $CONR^{13}R^{14}$; $NR^{13}SO_2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;

$R^2$ is 1-$C_4$ haloalkyl;

$R^3$ is H or 1-$C_8$ alkyl optionally substituted by one or more halogen atoms;

$R^4$ is H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —($C_1$-$C_4$ alkyl-$C_3$-$C_8$ cycloalkyl; $C_1$-$C_8$ alkoxy optionally substituted by one or more halogen atoms; $C_1$-$C_4$ alkoxy 1-$C_4$ alkyl; $C_1$-$C_8$ hydroxyalkyl; OH; CN; fluorine; —$(CH_2)_m$—$NR^{17}R^{18}$; —($C_0$-$C_4$ alkyl)-$C_6$-$C_{14}$ aryl; —($C_0$-$C_4$ alkyl)-3 to 14 membered heterocyclyl, wherein the heterocyclyl contains at least one heteroatom selected from N, O and S; or —($C_0$-$C_4$ alkyl)-$CO_2R^{15}$, wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents;

$R^{4a}$ is selected from H; $C_1$-$C_4$ alkyl optionally substituted by one or more halogen atoms; $C_2$-$C_8$ alkenyl; —($C_0$-$C_4$ alkyl)-$C_6$-$C_{14}$ aryl; —($C_0$-$C_4$ alkyl)-3 to 14 membered heterocyclyl; 1-$C_8$ hydroxyalkyl; halogen; —$(CH_2)_m$—$NR^{17}R^{18}$; —($C_0$-$C_4$ alkyl)-$CO_2R^{15}$ and —($C_0$-$C_4$ alkyl)-C(O)$NR^{17}R^{18}$; wherein the —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents;

$R^5$ is 1-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; alkyl-$C_3$-$C_8$ cycloalkyl; $C_1$-$C_8$ alkoxy optionally substituted by one or more halogen atoms; fluorine; —$(CH_2)_m$—$NR^{17}R^{18}$; —$(CH_2)_m$—$OR^4$; —($C_0$-$C_4$ alkyl)-$C_6$-$C_{14}$ aryl; —($C_0$-$C_4$ alkyl)-3 to 14 membered heterocyclyl, wherein the heterocyclyl contains at least one heteroatom selected from N, O and S; or —($C_0$-$C_4$ alkyl)-$CO_2R^{15}$, wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents; or $R^3$ and $R^4$ together form an oxo group (C═O); or $R^3$ and $R^5$ together with the carbon atoms to which they are bound form a 3 to 8 membered cycloalkyl; or $R^4$ and $R^5$ together with the carbon atoms to which they are bound form a 5 to 8 membered cycloalkyl or a 5 to 8 membered heterocyclyl containing one or more heteroatoms selected from N, O and S, wherein the ring system is optionally substituted by one or more Z substituents;
m is 0, 1, 2 or 3;
$R^8$, $R^{11}$, $R^{13}$ and $R^{17}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;
$R^9$, $R^{10}$, $R^{12}$, $R^{14}$, $R^{15}$, $R^{16}$ and $R^{18}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclyl, wherein the heterocyclyl contains at least one heteroatom selected from N, O and S, wherein the cycloalkyl, cycloalkenyl, aryl and heterocyclyl groups are each optionally substituted by one or more Z substituents; or
$R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclyl optionally substituted by one or more Z substituents;
Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{30}(SO_2)R^{32}$, $(SO_2)NR^{31}R^{32}$, $(SO_2)R^{32}$, $NR^{30}C(O)R^{32}$, $C(O)NR^{31}R^{32}$, $NR^{30}C(O)NR^{31}R^{32}$, $NR^{30}C(O)OR^{19}$, $NR^{31}R^{32}$, $C(O)OR^{31}$, $C(O)R^{31}$, $SR^{31}$, $OR^{31}$, oxo, CN, $NO_2$, halogen or a 3 to 14 membered heterocyclyl, wherein the heterocyclyl contains at least one heteroatom selected from N, O and S;
$R^{30}$ is H or $C_1$-$C_6$ alkyl;
$R^{31}$ and $R^{32}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl)$_2$; or
$R^{31}$ and $R^{32}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy;
or a pharmaceutically acceptable salt thereof.

Embodiment 1.1

The compound according to embodiment 1, wherein A is $CR^{4a}$ and $R^{4a}$ is selected from halogen, $C_1$-$C_4$ alkyl optionally substituted by one or more halogen atoms; $C_2$-$C_8$ alkenyl and —($C_0$-$C_4$ alkyl)-$C_6$-$C_{14}$ aryl; wherein the —($C_0$-$C_4$ alkyl)-$C_6$-$C_{14}$ aryl may be optionally substituted by one or more Z substituents.

Embodiment 1.2

The compound according to embodiment 1 or 1.1, wherein A is $CR^{4a}$ and $R^{4a}$ is selected from halogen, $C_1$-$C_4$ alkyl optionally substituted by one or more halogen atoms; $C_2$-$C_8$ alkenyl and —($C_0$-$C_4$ alkyl)-$C_6$-$C_{14}$ aryl.

Embodiment 1.3

The compound according to embodiment 1, 1.1 or 1.2, wherein A is $CR^{4a}$ and $R^{4a}$ is selected from chlorine, ethyl, isopropyl, isopropenyl and phenyl; wherein the phenyl may be optionally substituted by one or more Z substituents.

Embodiment 2

The compound according to embodiment 1, 1.1, 1.2 or 1.3, wherein X is

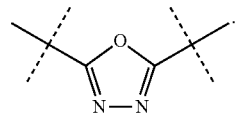

Embodiment 3

The compound according to any one of embodiments 1 to embodiment 2, wherein
$R^1$ is selected from H; $C_1$-$C_8$ alkyl optionally substituted by one or more halogen atoms; $C_3$-$C_{10}$ cycloalkyl; $C_1$-$C_8$ alkoxy optionally substituted by one or more halogen atoms; halogen; $C_6$-$C_{14}$ aryl; —($C_0$-$C_4$ alkyl)-3 to 14 membered heterocyclyl wherein the heterocyclyl contains at least one heteroatom selected from N, O and S; and $NR^{11}R^{12}$, wherein the aryl and heterocyclyl are each optionally substituted by one or more Z substituents.

Embodiment 4

The compound according to any one of embodiments 1 to 3, wherein $R^1$ is selected from H, $C_1$-$C_4$ alkyl optionally substituted by one or more halogen atoms; $C_3$-$C_{10}$ cycloalkyl; $C_1$-$C_4$ alkoxy optionally substituted by one or more halogen atoms and halogen.

Embodiment 5

The compound according to any one of embodiments 1 to 4, wherein $R^1$ is selected from $C_1$-$C_4$ alkyl optionally substituted by one or more halogen atoms; $C_3$-$C_{10}$ cycloalkyl; $C_1$-$C_4$ alkoxy optionally substituted by one or more halogen atoms and halogen.

Embodiment 6

The compound according to any one of embodiments 1 to 4, wherein $R^1$ is selected from H, methoxy, trifluoromethyl, bromine, cyclopropyl, and methyl.

Embodiment 7

The compound according to any one of embodiments 1 to 3, wherein $R^1$ is aryl, wherein aryl is phenyl optionally substituted by one or more Z substituents.

Embodiment 8

The compound according to any one of embodiments 1 to 7, wherein $R^2$ is $CF_3$.

Embodiment 9

The compound according to any one of embodiments 1 to 8, wherein $R^3$ is selected from H or $C_1$-$C_4$ alkyl optionally substituted by one and more halogen atoms.

Embodiment 10

The compound according to any one of embodiments 1 to 9, wherein $R^4$ is selected from H; $C_1$-$C_4$ alkyl optionally substituted by one or more halogen atoms; $C_1$-$C_4$ alkoxy optionally substituted by one or more halogen atoms; —$(CH_2)_m$—$NR^{17}R^{18}$ and OH; $R^{17}$ and $R^{18}$ are each independently H; $C_1$-$C_8$ alkyl optionally substituted by one or more halogen atoms.

Embodiment 11

The compound according to any one of embodiments 1 to 10, wherein $R^5$ is selected from H; $C_1$-$C_4$ alkyl optionally substituted by one or more halogen atoms; $C_1$-$C_4$ alkoxy optionally substituted by one or more halogen atoms; OH; CN; halogen; —$(C_0$-$C_4$ alkyl)-$C_6$-$C_{14}$ aryl; and —$(C_0$-$C_4$ alkyl)-3 to 14 membered heterocyclyl; wherein the heterocyclyl contains at least one heteroatom selected from N, O and S, wherein the aryl and heterocyclyl groups are each optionally substituted by one or more Z substituents.

Embodiment 12

The compound according to any one of embodiments 1 to 11, wherein $R^3$ and $R^5$ together with the carbon atoms to which they are bound form a 3 to 6 membered cycloalkyl.

Embodiment 13

The compound according to any one of embodiments 1 to 12, wherein $R^4$ and $R^5$ together with the carbon atoms to which they are bound form a 5 to 6 membered cycloalkyl or a 5 to 6 membered heterocyclyl containing one or more heteroatoms selected from N, O and S, wherein the heterocyclyl is optionally substituted by one or more Z substituents.

Embodiment 14

The compound according to any one of embodiments 1 to 8, wherein
$R^3$ is selected from H or $C_1$-$C_4$ alkyl optionally substituted by one and more halogen atoms;
$R^4$ is selected from H; $C_1$-$C_4$ alkyl optionally substituted by one or more halogen atoms; $C_1$-$C_4$ alkoxy optionally substituted by one or more halogen atoms; —$(CH_2)_m$—$NR^{17}R^{18}$ and OH;
$R^5$ is selected from H; $C_1$-$C_4$ alkyl optionally substituted by one or more halogen atoms; $C_1$-$C_4$ alkoxy optionally substituted by one or more halogen atoms; OH; CN; halogen; —$(C_0$-$C_4$ alkyl)-$C_6$-$C_{14}$ aryl; and —$(C_0$-$C_4$ alkyl)-3 to 14 membered heterocyclyl; wherein the heterocyclyl contains at least one heteroatom selected from N, O and S, wherein the aryl and heterocyclyl groups are each optionally substituted by one or more Z substituents; or
$R^3$ and $R^5$ together with the carbon atoms to which they are bound form a 3 to 6 membered cycloalkyl; or
$R^4$ and $R^5$ together with the carbon atoms to which they are bound form a 5 to 6 membered cycloalkyl or a 5 to 6 membered heterocyclyl containing one or more heteroatoms selected from N, O and S, wherein the heterocyclyl is optionally substituted by one or more Z substituents;
$R^{17}$ and $R^{18}$ are each independently H; $C_1$-$C_8$ alkyl optionally substituted by one or more halogen atoms.

Embodiment 15

The compound according to any one of embodiments 1 to 14, wherein
A is $CR^{4a}$;
X is

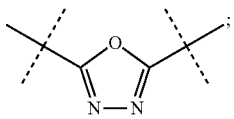

$R^1$ is selected from H; $C_1$-$C_4$ alkoxy optionally substituted by one or more halogen atoms; and $C_1$-$C_4$ alkoxy optionally substituted by one or more halogen atoms;
$R^2$ is $CF_3$,
$R^3$ is H, $CH_3$ or $CF_3$;
$R^4$ is H or Me;
$R^5$ is phenyl, —$NR^{17}R^{18}$ or OH; and
$R^{17}$ and $R^{18}$ are each independently H; $C_1$-$C_8$ alkyl optionally substituted by one or more halogen atoms.

Embodiment 16

The compound according to any one of embodiments 1 to 15, wherein
A is $CR^{4a}$;
X is

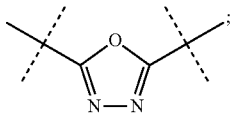

$R^1$ is selected from $C_1$-$C_4$ alkoxy optionally substituted by one or more halogen atoms; and $C_1$-$C_4$ alkoxy optionally substituted by one or more halogen atoms;
$R^2$ is $CF_3$,
$R^3$ is H, $CH_3$ or $CF_3$;
$R^4$ is H or Me;
$R^5$ is —$NR^{17}R^{18}$ or OH; and
$R^{17}$ and $R^{18}$ are each independently H; $C_1$-$C_8$ alkyl optionally substituted by one or more halogen atoms.

Embodiment 17

The compound according to any one of embodiments 1 to 16, the compounds of Formula I include compounds of Formula II:

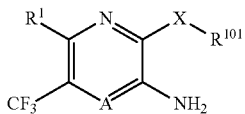

or a pharmaceutically acceptable salt thereof, wherein A, R¹, R², R³ and R⁴ᵃ are as defined in embodiments 1-16; and R¹⁰¹ is selected from the following:

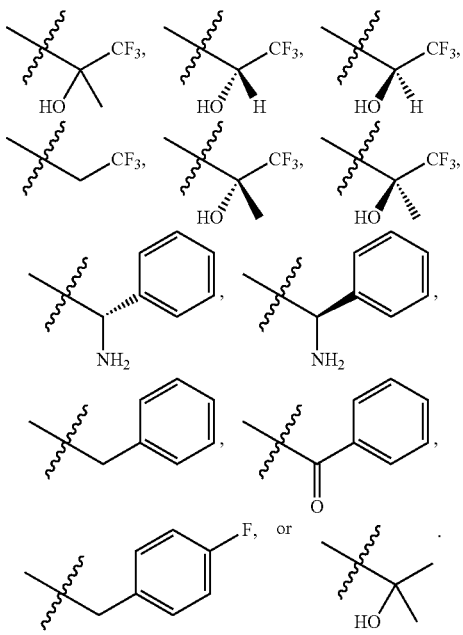

Embodiment 18

The compound according to embodiment 17, wherein A is CR⁴ᵃ, wherein R⁴ᵃ is H.

Embodiment 19

The compound according to embodiment 17 or 18, wherein A is CR⁴ᵃ;

R¹ is C₁-C₄ alkyl optionally substituted by one or more halogen atoms;

R¹⁰¹ is

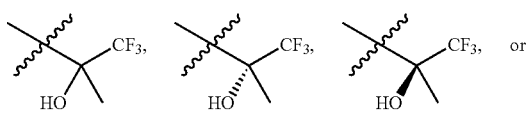

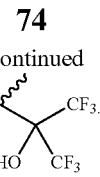

Embodiment 20

The compound according to embodiment 17, wherein R¹⁰¹ is

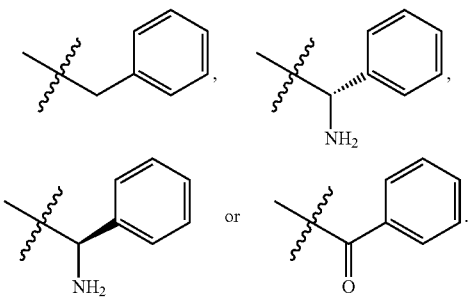

Embodiment 21

The compound according to embodiment 1, or pharmaceutically acceptable salts thereof, selected from:

2-(5-(3-Amino-6-methoxy-5-(trifluoromethyl)pyridin-2-yl)-1,3,4-oxadiazol-2-yl)-1,1,1-trifluoropropan-2-ol (racemic);

(R)-2-(5-(3-amino-6-methoxy-5-(trifluoromethyl)pyridin-2-yl)-1,3,4-oxadiazol-2-yl)-1,1,1-trifluoropropan-2-ol;

(S)-2-(5-(3-amino-6-methoxy-5-(trifluoromethyl)pyridin-2-yl)-1,3,4-oxadiazol-2-yl)-1,1,1-trifluoropropan-2-ol;

3-(5-Benzyl-1,3,4-oxadiazol-2-yl)-5-bromo-6-(trifluoromethyl)pyrazin-2-amine;

(5-(3-Amino-6-bromo-5-(trifluoromethyl)pyrazin-2-yl)-1,3,4-oxadiazol-2-yl)(phenyl)methanone;

2-(5-(3-Amino-5,6-bis(trifluoromethyl)pyrazin-2-yl)-1,3,4-oxadiazol-2-yl)-1,1,1-trifluoropropan-2-ol;

2-(5-(3-Amino-5,6-bis(trifluoromethyl)pyrazin-2-yl)-1,3,4-oxadiazol-2-yl)-1,1,1-trifluoropropan-2-ol (racemic);

(R)-2-(5-(3-Amino-5,6-bis(trifluoromethyl)pyrazin-2-yl)-1,3,4-oxadiazol-2-yl)-1,1,1-trifluoropropan-2-ol;

(S)-2-(5-(3-Amino-5,6-bis(trifluoromethyl)pyrazin-2-yl)-1,3,4-oxadiazol-2-yl)-1,1,1-trifluoropropan-2-ol;

2-(5-Benzyl-1,3,4-oxadiazol-2-yl)-6-bromo-5-(trifluoromethyl)pyridin-3-amine;

2-(5-Benzyl-[1,3,4]oxadiazol-2-yl)-5-trifluoromethyl-pyridin-3-yl-amine;

2-[5-(4-Fluoro-benzyl)-[1,3,4]oxadiazol-2-yl]-5-trifluoromethyl-pyridin-3-yl-amine;

6-Bromo-2-[5-(4-fluoro-benzyl)-[1,3,4]oxadiazol-2-yl]-5-trifluoromethyl-pyridin-3-ylamine;

6-Bromo-2-[5-(2,2,2-trifluoro-ethyl)-[1,3,4]oxadiazol-2-yl]-5-trifluoromethyl-pyridin-3-ylamine;

2-(5-(3-Amino-6-cyclopropyl-5-(trifluoromethyl)pyridin-2-yl)-1,3,4-oxadiazol-2-yl)-1,1,1-trifluoropropan-2-ol;

2-(5-(3-amino-6-methyl-5-(trifluoromethyl)pyridin-2-yl)-1,3,4-oxadiazol-2-yl)-1,1,1-trifluoropropan-2-ol;

2-(5-(3-amino-6-bromo-5-(trifluoromethyl)pyridin-2-yl)-1,3,4-oxadiazol-2-yl)-1,1,1-trifluoropropan-2-ol;

2-(5-(3-Amino-5-(trifluoromethyl)pyridin-2-yl)-1,3,4-oxadiazol-2-yl)-1,1,1-trifluoropropan-2-ol;
(2-(5-(3-amino-5-(trifluoromethyl)pyridin-2-yl)-1,3,4-oxadiazol-2-yl)-1,1,1-trifluoropropan-2-ol (racemic).
(R)-2-(5-(3-amino-5-(trifluoromethyl)pyridin-2-yl)-1,3,4-oxadiazol-2-yl)-1,1,1-trifluoropropan-2-ol;
(S)-2-(5-(3-amino-5-(trifluoromethyl)pyridin-2-yl)-1,3,4-oxadiazol-2-yl)-1,1,1-trifluoropropan-2-ol;
2-(5-(3-Amino-6-bromo-5-(trifluoromethyl)pyridin-2-yl)-1,3,4-oxadiazol-2-yl)propan-2-ol;
(R)-2-(5-(amino(phenyl)methyl)-1,3,4-oxadiazol-2-yl)-6-bromo-5-(trifluoro methyl)pyridin-3-amine; and
2-(5-(3-Amino-5-(trifluoromethyl)pyridin-2-yl)-1,3,4-thiadiazol-2-yl)-1,1,1-trifluoro propan-2-ol.
(R)-2-[5-(3-Amino-4-chloro-6-methoxy-5-trifluoromethyl-pyridin-2-yl)-[1,3,4]oxadiazol-2-yl]-1,1,1-trifluoro-propan-2-ol;
(S)-2-(5-(3-Amino-4-chloro-6-methoxy-5-(trifluoromethyl)pyridin-2-yl)-1,3,4-oxadiazol-2-yl)-1,1,1-trifluoropropan-2-ol;
(S)-2-[5-(3-Amino-4-ethyl-6-methoxy-5-trifluoromethyl-pyridin-2-yl)-[1,3,4]oxadiazol-2-yl]-1,1,1-trifluoro-propan-2-ol;
(S)-2-[5-(3-Amino-4-isopropenyl-6-methoxy-5-trifluoromethyl-pyridin-2-yl)-[1,3,4]oxadiazol-2-yl]-1,1,1-trifluoro-propan-2-ol;
(S)-2-[5-(3-Amino-4-isopropyl-6-methoxy-5-trifluoromethyl-pyridin-2-yl)-[1,3,4]oxadiazol-2-yl]-1,1,1-trifluoro-propan-2-ol; and
(S)-2-[5-(3-Amino-6-methoxy-4-phenyl-5-trifluoromethyl-pyridin-2-yl)-[1,3,4]oxadiazol-2-yl]-1,1,1-trifluoro-propan-2-ol.

Embodiment 22

A compound according to any one of embodiments 1 to 17 for use as a pharmaceutical.

Embodiment 23

A compound according to any one of embodiments 1 to 17 for use in the treatment of an inflammatory or obstructive airways disease or mucosal hydration.

Embodiment 24

Use of a compound according to any one of embodiments 1 to 17 in the manufacture of a medicament for use in the treatment of an inflammatory or obstructive airways disease or mucosal hydration.

Embodiment 25

A pharmaceutical composition, comprising:
the compound according to any one of embodiments 1 to 17 and
one or more pharmaceutically acceptable excipients.

Embodiment 26

A pharmaceutical combination, comprising:
a first active comprising the compound according to any one of embodiments 1 to 17, and a second active selected from osmotic agents, ENaC blockers, anti-inflammatory agents, bronchodilatory agents, antihistamine agents, anti-tussive agents, antibiotic agents and DNase drug substances, wherein the first and second actives may be in the same or different pharmaceutical composition.

Embodiment 27

A method for the prevention or treatment of a CFTR mediated condition or disease, comprising:
administering an effective amount of at least one compound according to any one of embodiments 1 to 17 to a subject in need of such treatment.

The invention claimed is:
1. A compound of Formula I

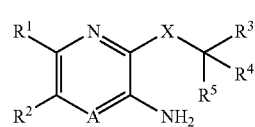

wherein:
A is N or $CR^{4a}$;
X is

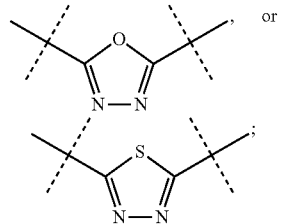

$R^1$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; halogen; $SO_2NR^8R^9$; $SO_2R^{10}$; S—$C_1$-$C_8$alkyl optionally substituted by one or more halogen atoms; S—$C_6$-$C_{14}$ aryl; —($C_0$-$C_4$ alkyl)-$C_6$-$C_{14}$ aryl; and —($C_0$-$C_4$ alkyl)-3 to 14 membered heterocyclyl; wherein the heterocyclyl contains at least one heteroatom selected from N, O and S; CN; $NR^{11}R^{12}$; $CONR^{13}R^{14}$; $NR^{13}SO_2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;
$R^2$ is $C_1$-$C_4$ haloalkyl;
$R^3$ is H or $C_1$-$C_8$ alkyl optionally substituted by one or more halogen atoms;
$R^4$ is H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; $C_1$-$C_4$ alkoxy $C_1$-$C_4$ alkyl; $C_1$-$C_8$ hydroxyalkyl; OH; CN; fluorine; —$(CH_2)_m$—$NR^{17}R^{18}$; —($C_0$-$C_4$ alkyl)-$C_6$-$C_{14}$ aryl; —($C_0$-$C_4$ alkyl)-3 to 14 membered heterocyclyl, wherein the heterocyclyl contains at least one heteroatom selected from N, O and S; or —($C_0$-$C_4$ alkyl)-$CO_2R^{15}$, wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents;

$R^{4a}$ is selected from H; $C_1$-$C_4$ alkyl optionally substituted by one or more halogen atoms; $C_2$-$C_8$ alkenyl; —($C_0$-$C_4$ alkyl)-$C_6$-$C_{14}$ aryl; —($C_0$-$C_4$ alkyl)-3 to 14 membered heterocyclyl; $C_1$-$C_8$ hydroxyalkyl; halogen; —$(CH_2)_m$—$NR^{17}R^{18}$; —($C_0$-$C_4$ alkyl)-$CO_2R^{15}$ and —($C_0$-$C_4$ alkyl)-C(O)$NR^{17}R^{18}$; wherein the —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents;

$R^5$ is $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; fluorine; —$(CH_2)_m$—$NR^{17}R^{18}$; —$(CH_2)_m$—$OR^4$; —($C_0$-$C_4$ alkyl)-$C_6$-$C_{14}$ aryl; —($C_0$-$C_4$ alkyl)-3 to 14 membered heterocyclyl, wherein the heterocyclyl contains at least one heteroatom selected from N, O and S; or —($C_0$-$C_4$ alkyl)-$CO_2R^{15}$, wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclyl groups are each optionally substituted by one or more Z substituents; or $R^3$ and $R^4$ together form an oxo group (C=O); or $R^3$ and $R^5$ together with the carbon atoms to which they are bound form a 3 to 8 membered cycloalkyl; or $R^4$ and $R^5$ together with the carbon atoms to which they are bound form a 5 to 8 membered cycloalkyl or a 5 to 8 membered heterocyclyl containing one or more heteroatoms selected from N, O and S, wherein the ring system is optionally substituted by one or more Z substituents;

m is 0, 1, 2 or 3;

$R^8$, $R^{11}$, $R^{13}$ and $R^{17}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;

$R^9$, $R^{10}$, $R^{12}$, $R^{14}$, $R^{15}$, $R^{16}$ and $R^{18}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclyl, wherein the heterocyclyl contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclyl optionally substituted by one or more Z substituents;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{30}(SO_2)R^{32}$, $(SO_2)NR^{31}R^{32}$, $(SO_2)R^{32}$, $NR^{30}C(O)R^{32}$, $C(O)NR^{31}R^{32}$, $NR^{30}C(O)NR^{31}R^{32}$, $NR^{30}C(O)OR^{19}$, $NR^{31}R^{32}$, $C(O)OR^{31}$, $C(O)R^{31}$, $SR^{31}$, $OR^{31}$, oxo, CN, $NO_2$, halogen or a 3 to 14 membered heterocyclyl, wherein the heterocyclyl contains at least one heteroatom selected from N, O and S;

$R^{30}$ is H or $C_1$-$C_6$ alkyl;

$R^{31}$ and $R^{32}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{31}$ and $R^{32}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or a pharmaceutically acceptable salt thereof.

2. The compound according to claim 1, wherein X is

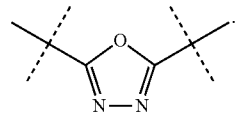

3. The compound according to claim 1, wherein
$R^1$ is selected from H; $C_1$-$C_8$ alkyl optionally substituted by one or more halogen atoms; $C_3$-$C_{10}$ cycloalkyl; $C_1$-$C_8$ alkoxy optionally substituted by one or more halogen atoms; halogen; $C_6$-$C_{14}$ aryl and —($C_0$-$C_4$ alkyl)-3 to 14 membered heterocyclyl wherein the heterocyclyl contains at least one heteroatom selected from N, O and S; and $NR^{11}R^{12}$, wherein the aryl and heterocyclyl are each optionally substituted by one or more Z substituents.

4. The compound according to claim 1, wherein
$R^1$ is selected from H, $C_1$-$C_4$ alkyl optionally substituted by one or more halogen atoms; $C_3$-$C_{10}$ cycloalkyl; $C_1$-$C_4$ alkoxy optionally substituted by one or more halogen atoms and halogen.

5. The compound according to claim 1, wherein $R^1$ is selected from $C_1$-$C_4$ alkyl optionally substituted by one or more halogen atoms; $C_1$-$C_4$ alkoxy optionally substituted by one or more halogen atoms and halogen.

6. The compound according to claim 1, wherein
$R^1$ is aryl, wherein aryl is phenyl optionally substituted by one or more Z substituents.

7. The compound according to claim 1, wherein
$R^2$ is $CF_3$.

8. The compound according to claim 1, wherein
$R^3$ is H or $C_1$-$C_4$ alkyl optionally substituted by one or more halogen atoms;
$R^4$ is H; $C_1$-$C_4$ alkyl optionally substituted by one or more halogen atoms; $C_1$-$C_4$ alkoxy optionally substituted by one or more halogen atoms; —$(CH_2)_m$—$NR^{17}R^{18}$; or OH;

R⁵ is H; $C_1$-$C_4$ alkyl optionally substituted by one or more halogen atoms; $C_1$-$C_4$ alkoxy optionally substituted by one or more halogen atoms; OH; CN; halogen; —($C_0$-$C_4$ alkyl)-$C_6$-$C_{14}$ aryl; or —($C_0$-$C_4$ alkyl)-3 to 14 membered heterocyclyl, wherein the heterocyclyl contains at least one heteroatom selected from N, O and S, wherein the aryl and heterocyclyl groups are each optionally substituted by one or more Z substituents; or R³ and R⁵ together with the carbon atoms to which they are bound form a 3 to 6 membered cycloalkyl; or R⁴ and R⁵ together with the carbon atoms to which they are bound form a 5 to 6 membered cycloalkyl or a 5 to 6 membered heterocyclic ring system containing one or more heteroatoms selected from N, O and S, wherein the ring system is optionally substituted by one or more Z substituents;

R¹⁷ and R¹⁸ are each independently H; $C_1$-$C_8$ alkyl optionally substituted by one or more halogen atoms.

9. The compound according to claim 1, wherein
A is $CR^{4a}$;
X is

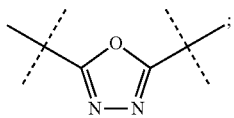

R¹ is selected from H; $C_1$-$C_4$ alkoxy optionally substituted by one or more halogen atoms; and $C_1$-$C_4$ alkoxy optionally substituted by one or more halogen atoms;
R² is $CF_3$,
R³ is H, $CH_3$ or $CF_3$;
R⁴ is H or Me;
R⁵ is phenyl, —$NR^{17}R^{18}$ or OH; and
R¹⁷ and R¹⁸ are each independently H; $C_1$-$C_8$ alkyl optionally substituted by one or more halogen atoms.

10. The compound according to claim 1, wherein
A is $CR^{4a}$;
X is

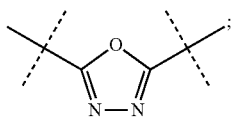

R¹ is selected from $C_1$-$C_4$ alkoxy optionally substituted by one or more halogen atoms; and $C_1$-$C_4$ alkoxy optionally substituted by one or more halogen atoms;
R² is $CF_3$,
R³ is H, $CH_3$ or $CF_3$;
R⁴ is H or Me;
R⁵ is —$NR^{17}R^{18}$ or OH; and
R¹⁷ and R¹⁸ are each independently H; $C_1$-$C_8$ alkyl optionally substituted by one or more halogen atoms.

11. The compound according to claim 1, or pharmaceutically acceptable salts thereof, selected from:
2-(5-(3-Amino-6-methoxy-5-(trifluoromethyl)pyridin-2-yl)-1,3,4-oxadiazol-2-yl)-1,1,1-trifluoropropan-2-ol (racemic);
(R)-2-(5-(3-amino-6-methoxy-5-(trifluoromethyl)pyridin-2-yl)-1,3,4-oxadiazol-2-yl)-1,1,1-trifluoropropan-2-ol;
(S)-2-(5-(3-amino-6-methoxy-5-(trifluoromethyl)pyridin-2-yl)-1,3,4-oxadiazol-2-yl)-1,1,1-trifluoropropan-2-ol;
3-(5-Benzyl-1,3,4-oxadiazol-2-yl)-5-bromo-6-(trifluoromethyl)pyrazin-2-amine;
(5-(3-Amino-6-bromo-5-(trifluoromethyl)pyrazin-2-yl)-1,3,4-oxadiazol-2-yl)(phenyl)methanone;
2-(5-(3-Amino-5,6-bis(trifluoromethyl)pyrazin-2-yl)-1,3,4-oxadiazol-2-yl)-1,1,1-trifluoropropan-2-ol;
2-(5-(3-Amino-5,6-bis(trifluoromethyl)pyrazin-2-yl)-1,3,4-oxadiazol-2-yl)-1,1,1-trifluoropropan-2-ol (racemic);
(R)-2-(5-(3-Amino-5,6-bis(trifluoromethyl)pyrazin-2-yl)-1,3,4-oxadiazol-2-yl)-1,1,1-trifluoropropan-2-ol;
(S)-2-(5-(3-Amino-5,6-bis(trifluoromethyl)pyrazin-2-yl)-1,3,4-oxadiazol-2-yl)-1,1,1-trifluoropropan-2-ol;
2-(5-Benzyl-1,3,4-oxadiazol-2-yl)-6-bromo-5-(trifluoromethyl)pyridin-3-amine;
2-(5-Benzyl-[1,3,4]oxadiazol-2-yl)-5-trifluoromethyl-pyridin-3-yl-amine;
2-[5-(4-Fluoro-benzyl)-[1,3,4]oxadiazol-2-yl]-5-trifluoromethyl-pyridin-3-yl-amine;
6-Bromo-2-[5-(4-fluoro-benzyl)-[1,3,4]oxadiazol-2-yl]-5-trifluoromethyl-pyridin-3-ylamine;
6-Bromo-2-[5-(2,2,2-trifluoro-ethyl)-[1,3,4]oxadiazol-2-yl]-5-trifluoromethyl-pyridin-3-ylamine;
2-(5-(3-Amino-6-cyclopropyl-5-(trifluoromethyl)pyridin-2-yl)-1,3,4-oxadiazol-2-yl)-1,1,1-trifluoropropan-2-ol;
2-(5-(3-amino-6-methyl-5-(trifluoromethyl)pyridin-2-yl)-1,3,4-oxadiazol-2-yl)-1,1,1-trifluoropropan-2-ol;
2-(5-(3-amino-6-bromo-5-(trifluoromethyl)pyridin-2-yl)-1,3,4-oxadiazol-2-yl)-1,1,1-trifluoropropan-2-ol;
2-(5-(3-Amino-5-(trifluoromethyl)pyridin-2-yl)-1,3,4-oxadiazol-2-yl)-1,1,1-trifluoropropan-2-ol;
(2-(5-(3-amino-5-(trifluoromethyl)pyridin-2-yl)-1,3,4-oxadiazol-2-yl)-1,1,1-trifluoropropan-2-ol (racemic);
(R)-2-(5-(3-amino-5-(trifluoromethyl)pyridin-2-yl)-1,3,4-oxadiazol-2-yl)-1,1,1-trifluoropropan-2-ol;
(S)-2-(5-(3-amino-5-(trifluoromethyl)pyridin-2-yl)-1,3,4-oxadiazol-2-yl)-1,1,1-trifluoropropan-2-ol;
2-(5-(3-Amino-6-bromo-5-(trifluoromethyl)pyridin-2-yl)-1,3,4-oxadiazol-2-yl)propan-2-ol;
(R)-2-(5-(amino(phenyl)methyl)-1,3,4-oxadiazol-2-yl)-6-bromo-5-(trifluoro methyl)pyridin-3-amine; and
2-(5-(3-Amino-5-(trifluoromethyl)pyridin-2-yl)-1,3,4-thiadiazol-2-yl)-1,1,1-trifluoro propan-2-ol;
(R)-2-[5-(3-Amino-4-chloro-6-methoxy-5-trifluoromethyl-pyridin-2-yl)-[1,3,4]oxadiazol-2-yl]-1,1,1-trifluoro-propan-2-ol;
(S)-2-(5-(3-Amino-4-chloro-6-methoxy-5-(trifluoromethyl)pyridin-2-yl)-1,3,4-oxadiazol-2-yl)-1,1,1-trifluoropropan-2-ol;
(S)-2-[5-(3-Amino-4-ethyl-6-methoxy-5-trifluoromethyl-pyridin-2-yl)-[1,3,4]oxadiazol-2-yl]-1,1,1-trifluoro-propan-2-ol;
(S)-2-[5-(3-Amino-4-isopropenyl-6-methoxy-5-trifluoromethyl-pyridin-2-yl)-[1,3,4]oxadiazol-2-yl]-1,1,1-trifluoro-propan-2-ol;
(S)-2-[5-(3-Amino-4-isopropyl-6-methoxy-5-trifluoromethyl-pyridin-2-yl)-[1,3,4]oxadiazol-2-yl]-1,1,1-trifluoro-propan-2-ol; and
(S)-2-[5-(3-Amino-6-methoxy-4-phenyl-5-trifluoromethyl-pyridin-2-yl)-[1,3,4]oxadiazol-2-yl]-1,1,1-trifluoro-propan-2-ol.

12. A pharmaceutical composition, comprising:
the compound according to claim 1 and
one or more pharmaceutically acceptable excipients.

13. A pharmaceutical combination, comprising:
a first active comprising the compound according to claim 1, and a second active selected from osmotic agents, ENaC blockers, anti-inflammatory agents, bronchodilatory agents, antihistamine agents, anti-tussive agents, antibiotic agents and DNase drug substances, wherein the first and second actives may be in the same or different pharmaceutical composition.

14. A method for the treatment of cystic fibrosis, comprising:
administering an effective amount of at least one compound according to claim 1 to a subject in need of such treatment.

* * * * *